(12) United States Patent
Tang et al.

(10) Patent No.: US 8,129,111 B2
(45) Date of Patent: *Mar. 6, 2012

(54) FLUORESCENT WATER-SOLUABLE CONJUGATED POLYENE COMPOUNDS THAT EXHIBIT AGGREGATION INDUCED EMISSION AND METHODS OF MAKING AND USING SAME

(75) Inventors: Benzhong Tang, Hong Kong (CN); Yuning Hong, Hong Kong (CN); Matthias Haeussler, Bad Lauchstaedt (DE); Hui Tong, Uppsala (SE); Yongqiang Dong, Beijing (CN); Zhen Li, Wuhan (CN); Changmin Xing, Beijing (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 137 days.

This patent is subject to a terminal disclaimer.

(21) Appl. No.: 12/453,892

(22) Filed: May 26, 2009

(65) Prior Publication Data

US 2010/0009362 A1 Jan. 14, 2010

Related U.S. Application Data

(63) Continuation-in-part of application No. 12/000,130, filed on Dec. 10, 2007, now Pat. No. 7,939,613, which is a continuation-in-part of application No. 11/408,846, filed on Apr. 21, 2006.

(60) Provisional application No. 61/071,928, filed on May 27, 2008, provisional application No. 60/929,364, filed on Jun. 25, 2007, provisional application No. 60/873,431, filed on Dec. 8, 2006, provisional application No. 60/673,562, filed on Apr. 22, 2005.

(51) Int. Cl.
*C12Q 1/68* (2006.01)
*C12Q 1/70* (2006.01)
*G01N 33/53* (2006.01)

(52) U.S. Cl. .................. 435/6; 435/5; 435/7.1; 435/7.2; 436/9.1; 436/9.6

(58) Field of Classification Search .................. 435/5, 6, 435/7.1, 7.2; 436/9.1, 9.6
See application file for complete search history.

(56) References Cited

OTHER PUBLICATIONS

Chang, Cheng-Chung et al., "A Fluorescent Carbazole Derivative: High Sensitivity for Quadruplex DNA", Anal. Chem., 2003, pp. 6177-6183, vol. 75, No. 22, American Chemical Society.
Dixon, Isabelle M. et al., "A G-Quadruplex Ligand with 10000-Fold Selectivity over Duplex DNA", J. Am. Chem. Soc., 2007, pp. 1502-1503, vol. 129, American Chemical Society.
Moyzis, Robert K. et al., "A highly conserved repetitive DNA sequence, (TTAGGG)n, present at the telomeres of human chromosomes", Proc. Natl. Acad. Sci. USA, 1988, pp. 6622-6626, vol. 85.

(Continued)

*Primary Examiner* — Jezia Riley
(74) *Attorney, Agent, or Firm* — The Nath Law Group; Tanya E. Harkins; Mih Suhn Koh

(57) ABSTRACT

The presently described subject matter is directed to water-soluble conjugated polyene compounds that exhibit aggregation induced emission, as well as to water dispersible, fluorescent, polymeric microparticles and/or nanoparticles comprising the water-soluble conjugated polyene compounds. Also provided are methods of making and using the compounds and particles. The described conjugated polyene compounds are useful as bioprobes for the detection biomacromolecules, as well as in the manufacture of sensors.

13 Claims, 67 Drawing Sheets

OTHER PUBLICATIONS

Walmsley, Judith A. et al., "A New Model for the K+-Induced Macromolecular Structure of Guanosine 5'-Monophosphate in Solution", Biochemistry, 1999, pp. 14063-14068, vol. 38, American Chemical Society.

Xie, Zengqi Xie et al., "A Class of Nonplanar Conjugated Compounds with Aggregation-Induced Emission: Structural and Optical Properties of 2,5-Dephenyl-1,4-distyrylbenzene Derivatives with All Cis Double Bonds", J. Phys. Chem. B, 2006, pp. 20993-21000, vol. 110, American Chemical Society.

Dong, Yongqiang et al., "Aggregation-induced and crystallization-enhanced emissions of 1,2-diphenyl-3,4-bis (diphenylmethylene)-1-cyclobutene", Chem. Commun., 2007, pp. 3255-3257, The Royal Society of Chemistry.

Luo, Jingdong et al., "Aggregation-induced emission of 1-methyl-1,2,3,4,5-pentaphenylsilole", Chem. Commun., 2001, pp. 1740-1741, The Royal Society of Chemistry.

Dong, Yongqiang et al., "Aggregation-induced emissions of tetraphenylethene derivatives and their utilities as chemical vapor sensors and in organic light-emitting diodes", Applied Physics Letters, 2007, vol. 91, American Institute of Physics.

Zhao, Qiang et al., "Aggregation-induced phosphorescent emission (AIPE) of iridium(III) complexes", Chem. Commun., 2008, pp. 685-687, The Royal Society of Chemistry.

Phan, Anh Tuan et al., "An interlocked dimeric parallel-stranded DNA quadruplex: A potent inhibitor of HIV-1 integrase", PNAS, 2005, pp. 634-639, vol. 102, No. 3, The National Academy of Sciences of the USA.

Ueyama, Hiroyuki et al., "A Novel Potassium Sensing in Aqueous Media with a Synthetic Oligonucleotide Derivative. Fluorescence Resonance Energy Transfer Associated with Guanine Quartet—Potassium Ion Complex Formation", J. Am. Chem. Soc., 2002, pp. 14286-14287, vol. 124, The American Chemical Society.

McMurry, John E., "Carbonyl-Coupling Reactions Using Low-Valent Titanium", Chem. Rev., 1989, pp. 1513-1524, vol. 89, American Chemical Society.

Wheelhouse, Richard T. et al., "Cationic Porphyrins as Telomerase Inhibitors: the Interaction of Tetra-(N-methyl-4-pyridyl)porphine with Quadruplex DNA", J. Am. Chem. Soc., 1998, pp. 3261-3262, vol. 120, American Chemical Society.

Parkinson, Gary N. et al., "Crystal structure of parallel quadruplexes from human telomeric DNA", Nature, 2002, pp. 876-880, vol. 417, Nature Publishing Group.

Zhao, Yong et al., "Determining the Folding and Unfolding Rate Constants of Nucleic Acids by Biosensor. Application to Telomere G-Quadruplex", J. Am. Chem. Soc., 2004, pp. 13255-13264, vol. 126, American Chemical Society.

Simonsson, Tomas, "DNA Tetraplex Formation Studied with Fluorescence Resonance Energy Transfer", The Journal of Biological Chemistry, 1999, pp. 17379-17383, vol. 274, No. 24, The American Society for Biochemistry and Molecular Biology, Inc.

Jayanty, S. et al., "Enhanced Fluorescence of Remote Functionalized Diaminodicyanoquinodimethanes in the Solid State and Fluorescence Switching in a Doped Polymer by Solvent Vapors", Chem. Eur. J., 2004, pp. 791-797, vol. 10, Wiley-VCH Verlag GmbH & Co. KGaA, Weinheim, Germany.

An, Byeong-Kwan et al., "Enhanced Emission and Its Switching in Fluorescent Organic Nanoparticles", J. Am. Chem. Soc., 2002, pp. 14410-14415, vol. 124, American Chemical Society.

Mergny, Jean-Louis, "Fluorescence Energy Transfer as a Probe for Tetraplex Formation: The i-Motif", Biochemistry, 1999, pp. 1573-1581, vol. 38, American Chemical Society.

Han, Mina R. et al., "Fluorescence Enhancement from Self-Assembled Aggregates: Substituent Effects on Self-Assembly of Azobenzenes", Chem. Mater., 2006, pp. 2784-2786, vol. 18, American Chemical Society.

Zeng, Qi et al., "Fluorescence enhancements of benzene-cored luminophors by restricted intramolecular rotations: AIE and AIEE effects", Chem. Commun., 2007, pp. 70-72, The Royal Society of Chemistry.

Mergny, Jean-Louis et al., "Fluorescence Resonance Energy Transfer as a Probe for G-Quartet Formation by a Telomeric Repeat", CHEMBIOCHEM, 2001, pp. 124-132, vol. 2, Wiley-VCH-Verlag GmbH, Weinheim, Germany.

He, Fang et al., "Fluorescent Amplifying Recognition for DNA G-Quadruplex Folding with a Cationic Conjugated Polymer: A Platform for Homogeneous Potassium Detection", J. Am. Chem. Soc., 2005, pp. 12343-12346, vol. 127, American Chemical Society.

Tong, Hui et al., "Fluorescent 'light-up' bioprobes based on tetraphenylethylene derivatives with aggregation-induced emission characteristics", Chem. Commun., 2006, pp. 3705-3707, The Royal Society of Chemistry.

Ambrus, Attila et al., "Human telomeric sequence forms a hybrid-type intramolecular G-quadruplex structure with mixed parallel/antiparallel strands in potassium solution", Nucleic Acids Research, 2006, pp. 2723-2735, vol. 34, No. 9, Oxford University Press.

Haq, Ihtshamul et al., "Intercalative G-Tetraplex Stabilization of Telomeric DNA by a Cationic Porphyrin", J. Am. Chem. Soc., 1999, pp. 1768-1779, vol. 121, American Chemical Society.

Chang, Cheng-Chung et al., "Investigation of spectral conversion of d(TTAGGG)4 and d(TTAGGG)13 upon potassium titration by a G-quadruplex recognizer BMVC molecule", Nucleic Acids Research, 2007, pp. 2846-2860, vol. 35, No. 9.

Merkina, Elena E. et al., "Kinetic Stability of Intermolecular DNA Quadruplexes", Biophysical Journal, 2005, pp. 365-373, vol. 89, Biophysical Society.

Green, Jeremy J. et al., "Kinetics of Unfolding the Human Telomeric DNA Quadruplex Using a PNA Trap", J. Am. Chem. Soc., 2003, pp. 3763-3767, vol. 125, American Chemical Society.

Toal, Sarah J. et al., "Luminescent Silole Nanoparticles as Chemoselective Sensors for Cr(VI)", J. Am. Chem. Soc., 2005, pp. 11661-11665, vol. 127, American Chemical Society.

Collins, Kathleen, "Mammalian telomeres and telomerase", Current Opinion in Cell Biology, 2000, pp. 378-383, vol. 12, Elsevier Science Ltd.

Gilbert, Dara E. et al., "Multistranded DNA structures", Current Opinion in Structural Biology, 1999, pp. 305-314, vol. 9, Elsevier Science Ltd.

Mergny, Jean-Louis et al., "Natural and pharmacological regulation of telomerase", Nucleic Acids Research, 2002, pp. 839-865, vol. 30, No. 4, Oxford University Press.

Ho, Hoang-Anh et al., "Optical Sensors Based on Hybrid Aptamer/Conjugated Polymer Complexes", J. Am. Chem. Soc., 2004, pp. 1384-1387, vol. 126, American Chemical Society.

Venczel, Eduard A. et al., "Parallel and Antiparallel G-DNA Structures from a Complex Telomeric Sequence", Biochemistry, 1993, pp. 6220-6228, vol. 32, American Chemical Society.

Tong, Hui et al., "Protein Detection and Quantitation by Tetraphenylethene-Based Fluorescent Probes with Aggregation-Induced Emission Characteristics", J. Phys. Chem. B, 2007, pp. 11817-11823, vol. 111, American Chemical Society.

Bourdoncle, A. et al., "Quadruplex-Based Molecular Beacons as Tunable DNA Probes", J. Am. Chem. Soc., 2006, pp. 11094-11105, vol. 128, American Chemical Society.

He, Fang et al., "Quadruplex-to-Duplex Transition of G-Rich Oligonucleotides Probed by Cationic Water-Soluble Conjugated Polyelectrolytes", J. Am. Chem. Soc., 2006, pp. 6764-6765, vol. 128, American Chemical Society.

Yeh, Hsiu-Chih et al., "Readily synthesized arylamino fumaronitrile for non-doped red organic light-emitting diodes", Chem. Commun., 2003, pp. 2632-2633, The Royal Society of Chemistry.

Xu, Qiuwei et al., "Selective Localization and Rotational Immobilization of Univalent Cations on Quadruplex DNA", Biochemistry, 1993, pp. 13130-13137, vol. 32, American Chemical Society.

Lv, Wei et al., "Shape-Specific Detection Based on Fluorescence Resonance Energy Transfer Using a Flexible Water-Soluble Conjugated Polymer", J. Am. Chem. Soc., 2006, pp. 10281-10287, vol. 128, American Chemical Society.

Dai, Jixun et al., "Structure of the intramolecular human telomeric G-quadruplex in potassium solution: a novel adenine triple formation", Nucleic Acids Research, 2007, pp. 2440-2450, vol. 35, No. 7.

Furstenberg, Alexandre et al., "Structure-Fluorescence Contrast Relationship in Cyanine DNA Intercalators: Toward Rational Dye Design", Chem. Eur. J., 2007, pp. 8600-8609, vol. 13, Wiley-VCH Verlag GmbH & Co. KGaA, Weinheim, Germany.

Yu, Gui et al., "Structures, Electronic States, Photoluminescence, and Carrier Transport Properties of 1,1-Disubstituted 2,3,4,5-Tetraphenylsiloles", J. Am. Chem. Soc., 2005, pp. 6335-6346, vol. 127, American Chemical Society.

Dong, Yongqiang et al., "Switching the light emission of (4-biphenylyl)phenyldibenzofulvene by morphological modulation: crystallization-induced emission enhancement", Chem. Commun., 2007, pp. 40-42, The Royal Society of Chemistry.

Chen, Junwu et al., "Synthesis, Light Emission, Nanoaggregation, and Restricted Intramolecular Rotation of 1,1-Substituted 2,3,4,5-Tetraphenylsiloles", Chem. Mater., 2003, pp. 1535-1546, vol. 15, American Chemical Society.

Yuan, Chun-Xue et al., "Synthesis, Structure, and Aggregation-Induced Emission of a Novel Lambda-Shaped Pyridinium Salt Based on Troger's Base", J. Phys. Chem. C, 2007, pp. 12811-12816, vol. 111, American Chemical Society.

Peng, Qian et al., "Toward Quantitative Prediction of Molecular Fluorescence Quantum Efficiency: Role of Duschinsky Rotation", J. Am. Chem. Soc., 2007, pp. 9333-9339, vol. 129, American Chemical Society.

Tong, Hui et al., "Tunable aggregation-induced emission of diphenyldibenzofulvenes", Chem. Commun., 2006, pp. 1133-1135, The Royal Society of Chemistry.

Hardin, Charles C. et al., "Monovalent Cation Induced Structural Transitions in Telomeric DNAs: G-DNA Folding Intermediates", Biochemistry, 1991, pp. 4460-4472, vol. 30, American Chemical Society.

White, Elizabeth W., "Structure-specific recognition of quadruplex DNA by organic cations: Influence of shape, substituents and charge", Biophysical Chemistry, 2007, pp. 140-153, vol. 126, Elsevier B.V.

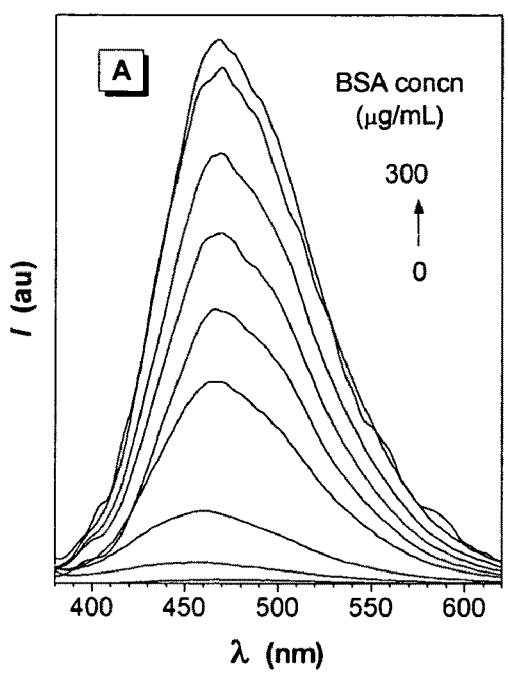
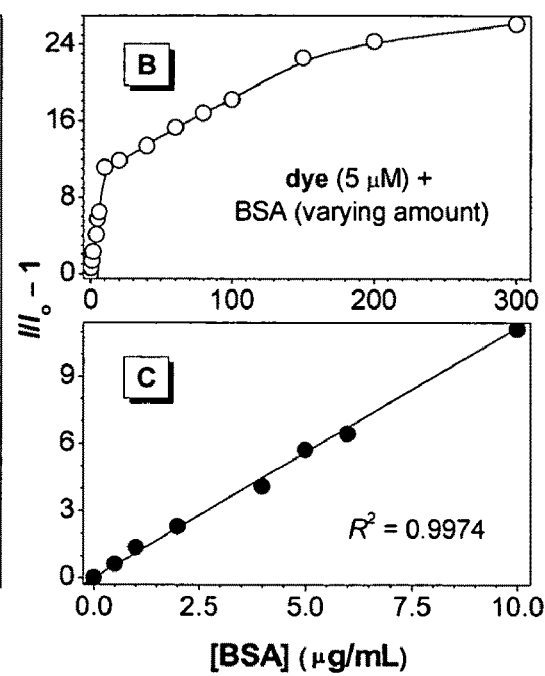
FIG. 2B
FIG. 2A
FIG. 2C

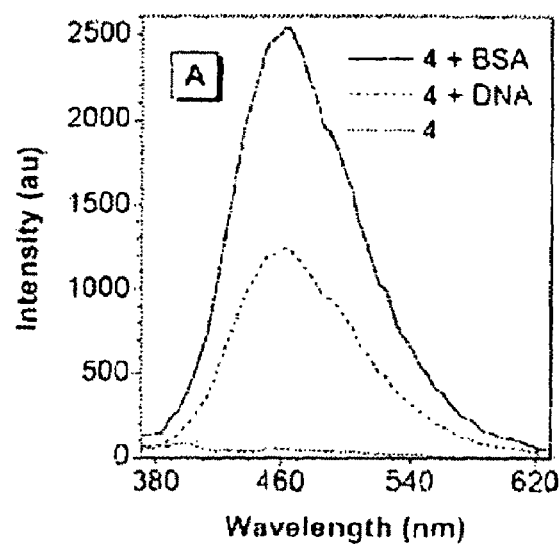 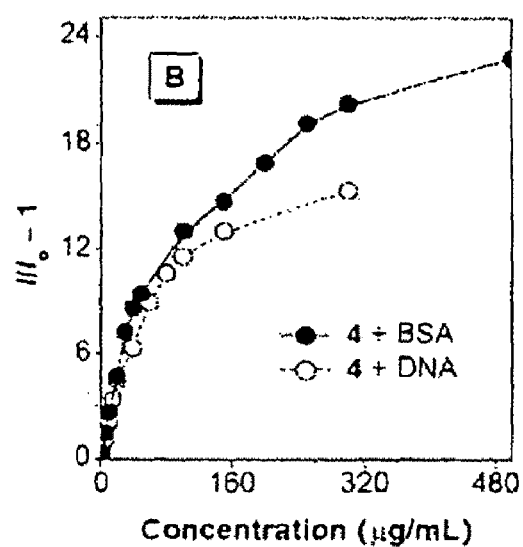
FIG. 12A　　　　FIG. 12B

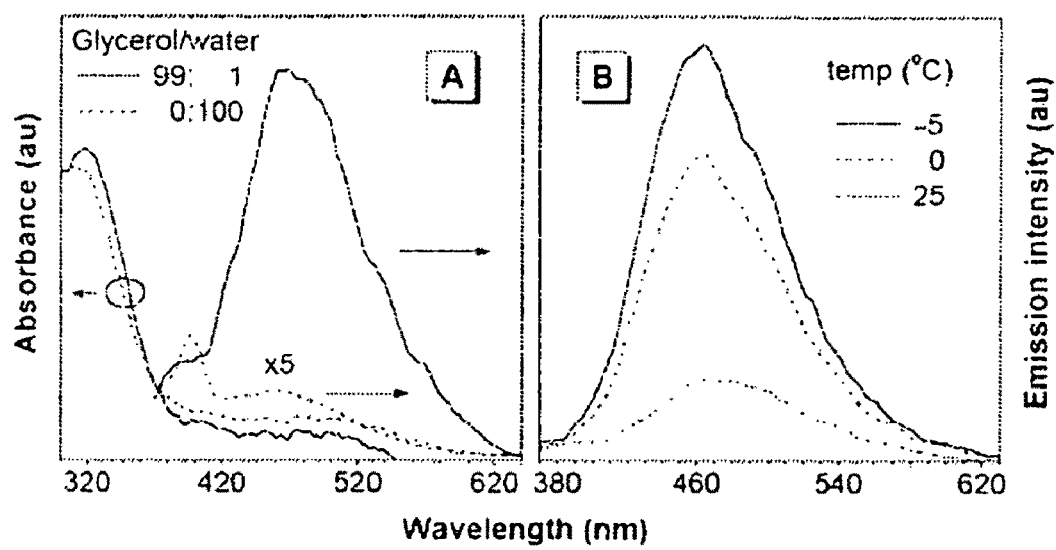
FIG. 13A  FIG. 13B

FIG. 16A and B (inset)

FIG. 19A
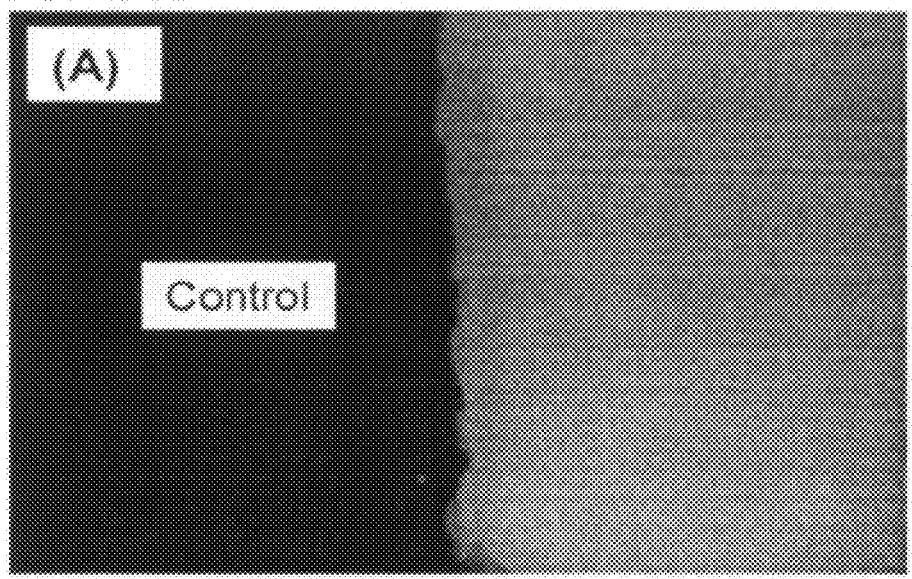
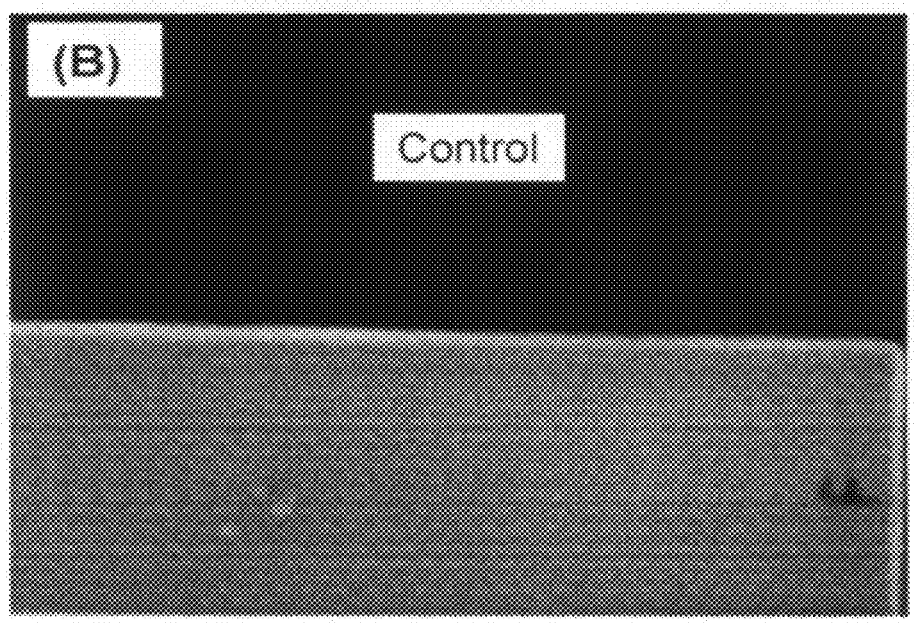
FIG. 19B

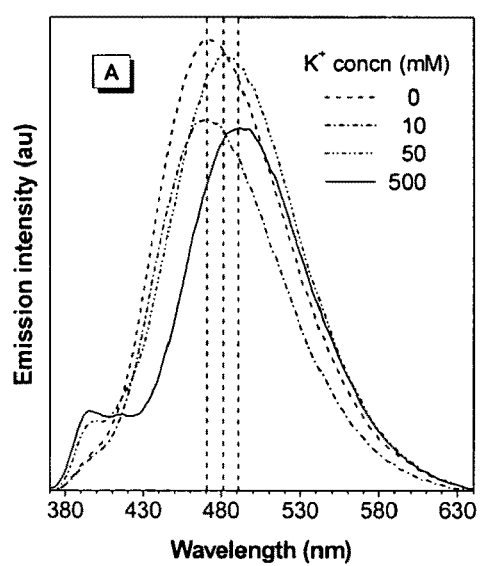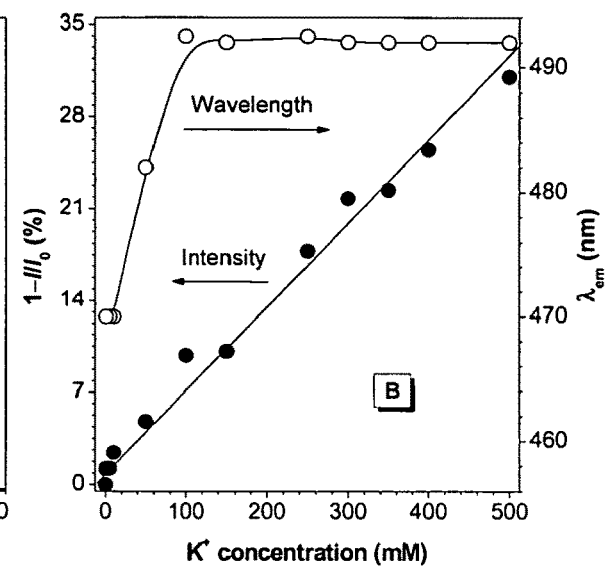
FIG. 32A  FIG. 32B

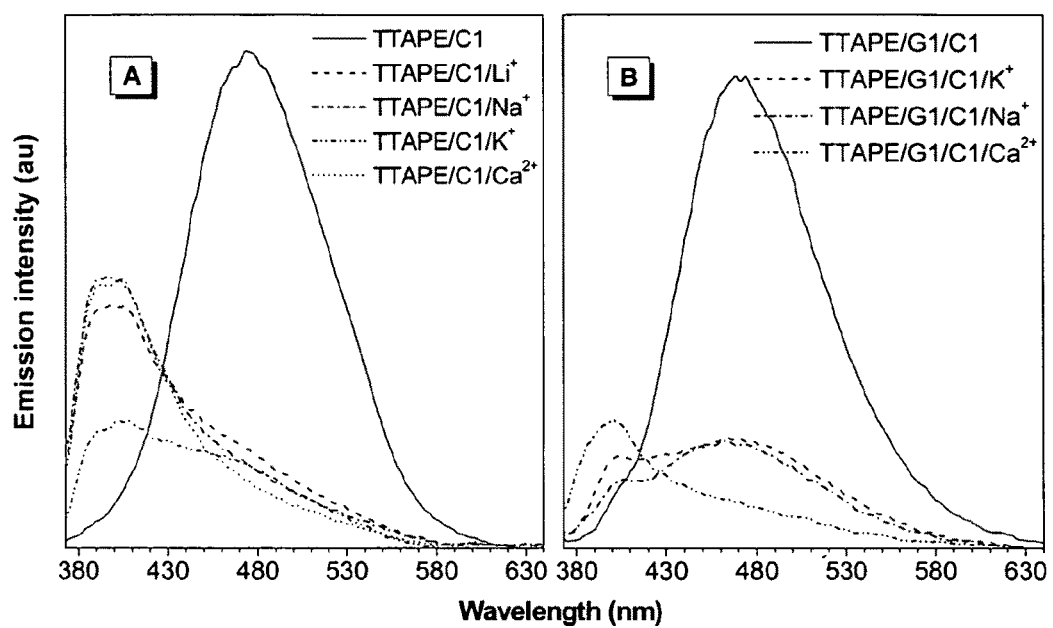
FIG. 38A                    FIG. 38B

FLUORESCENT WATER-SOLUABLE CONJUGATED POLYENE COMPOUNDS THAT EXHIBIT AGGREGATION INDUCED EMISSION AND METHODS OF MAKING AND USING SAME

CROSS REFERENCE TO RELATED APPLICATION

Pursuant to 35 U.S.C. §119(e), this application claims the benefit of Provisional Application No. 60/873,431 filed on Dec. 8, 2006, and to Provisional Application No. 60/929,364 filed on Jun. 25, 2007, and to Provisional Application No. 61/071,928 filed on May 27, 2008, and is also a Continuation-in-Part Application of U.S. Published Patent Application No. 2008/0220407, published on Sep. 11, 2008, which was filed on Dec. 10, 2007, which is a Continuation-in-Part Application of U.S. Published Patent Application No. 2006/0240565, published on Oct. 26, 2006, which was filed on Apr. 21, 2006 and claims priority to U.S. Provisional Application No. 60/673,562 filed on Apr. 22, 2005. All of the foregoing applications are hereby incorporated by reference in their entirety.

FIELD OF THE INVENTION

The presently described subject matter relates generally to compounds that exhibit aggregation induced emission, and more particularly to water-soluble conjugated polyene compounds that exhibit aggregation induced emission. The conjugated polyene compounds can be used as bioprobes for DNA detection, G-quadruplex identification, and potassium-ion sensing. The polyenes also can be utilized as an external fluorescent marker to study conformational structures, to monitor folding processes of label-free oligonucleotides with G-rich strand sequences, and to visualize DNA bands in PAGE assay. The assays incorporating the polyenes have applications in high-throughput anticancer drug screening.

BACKGROUND OF THE INVENTION

Fluorescence (FL) techniques have emerged as a mainstream research and development area in science and engineering, particularly in the field of biochemical and biological science. Currently, fluorescent molecules are used as probes for DNA sequencing, fluorescence-activated cell sorting, high throughput screening, and clinical diagnostics.

Fluorescence-based techniques offer high sensitivity, low background noises and broad dynamic ranges. A great number of fluorescent probes have been investigated and are already widely used in biotechnology. Many of them show favorable spectral properties of visible absorption and emission wavelength, high extinction coefficients, and reasonable quantum yields. Upon complexation with proteins and DNA, the fluorescence of the bioprobes can be enhanced/quenched and/or red/blue-shifted, thus enabling visual observation of the biomacromolecular species. Among these, the most useful probes are those that act as "turn-on" sensors, whose fluorescence is activated by the analytes.

Several probes for DNA detection based on fluorescent enhancement have been developed such as phenanthridine and acridine derivatives. Middendorf et al. have reported on ethidium bromide (EB), a well-known phenanthridine derivative, which has already been widely used for DNA-sequencing (U.S. Pat. No. 4,729,947, U.S. Pat. No. 5,346,603, U.S. Pat. No. 6,143,151, U.S. Pat. No. 6,143,153). FL enhancement induced by proteins can be attributed to the interaction with hydrophobic regions of proteins, such as NanoOrange (Molecular Probes, Inc., U.S. Pat. No. 6,818,642) and Nile red (U.S. Pat. No. 6,897,297, U.S. Pat. No. 6,465,208), or reaction with amine groups of proteins in the presence of cyanide or thiols, such as fluorescamine (U.S. Pat. No. 4,203,967) and o-phthaldialdehyde (U.S. Pat. No. 6,969,615, U.S. Pat. No. 6,607,918). The FL of cyanine dyes has been found to increase dramatically upon complexation with DNA and proteins. (U.S. Pat. No. 5,627,027, U.S. Pat. No. 5,410,030). Haugland et al. have reported unsymmetrical cyanine dyes, which possess superior fluorescent characteristics when complexed with nucleic acids (U.S. Pat. No. 5,436,134). The SYPRO® dyes are merocyanine dyes that are essentially non-fluorescent when free in solution but become intensely fluorescent in hydrophobic environments (e.g. SYPRO®Red and SYPRO®Orange dyes of Molecular Probes, Inc., U.S. Pat. No. 6,914,250, U.S. Pat. No. 6,316,267). Water-soluble cyanine dyes, such as Cy3 and Cy5, are commonly used in labeling of DNA or RNA for micorarray (V. R. Iyer et al., Science, 1999, 283, 83). Cy3 and Cy5 have merits of high fluorescence intensity and emission even in solid state, whereas, they are quite unstable and show insufficient detection sensitivity (U.S. Pat. No. 7,015,002).

As described in U.S. Pat. No. 7,109,314, a good fluorescent dye should possess a high fluorescent quantum yield and molecular absorption coefficient, as well as good solubility in aqueous media and stability under ambient conditions. However, most of the dyes discussed above are lipophilic, which are at best, only dispersible in aqueous media. For example, Nile Red, a dye used to stain proteins, should be first dissolved in acetone and then mixed rapidly with water immediately prior to use (J. R. Daban et al, Anal. Biochem, 1991, 199, 169).

Additionally, substantially all of the above-described fluorescent dyes suffer from the problem of aggregation-caused quenching (ACQ). Due to their lipophilic character, these fluorescent dyes are prone to aggregate when dispersed in aqueous media or when bound to biological macromolecules. The close proximity of the chromophores often induces a non-radiative energy transfer mechanism that results in self-quenching of the luminescence. This self-quenching drastically reduces the dyes' fluorescent signal thereby prohibiting their use as efficient bioprobes or biosensors.

Substantial effort has been made to mitigate aggregate formation of these dyes (J. R. Lakowicz, et al. Anal Biochem, 2003, 320, 13). However, only a small number of researchers have focused on the design and synthesis of novel organic molecules or polymers that do not suffer from fluorescent quenching, and moreover, even display enhanced light emission upon aggregation.

Recently, aggregation-induced emission (AIE) has been observed. This phenomena is exactly opposite of ACQ. Some non-emissive dyes can be induced to emit efficiently by the aggregate formation. AIE molecules with high quantum yields $\Phi_F$ (up to 0.85) and various emission colors (blue, green, yellow and red) have been reported. While the AIE dyes have been used for the construction of efficient optical and photonic devices, the possibility of employing them as bioprobes for detecting biopolymers have been virtually unexplored. Accordingly, there remains a great need for water-soluble "light-up" compounds and probes, for example, for the detection of biomacromolecules such as DNA and proteins.

There is a growing demand for new sensors useful for detecting/sensing biomacromolecules. Sensors based on detecting fluorescence of an analyte such as a biomacromolecule are highly sensitive, thereby lowering detection limits.

Many known fluorescent materials accomplish the detection of saccharides by the competing intramolecular interaction of an amine functionality with a boronic acid pendant. Less effort has been spent on the detection of other biological compounds. Furthermore, vapor-sensing compounds and devices are often manufactured from the expensive platinum salts and complexes and/or in combination with palladium. They are based mainly on a color shift from dark-red to light-red, making it difficult to visually sense the color shift. Sensors exhibiting an on-off change in their luminescent color rather than a color shift will be thus not only advantageous but also more sensitive. To applicants' knowledge, the only known "on-off" example was shown by Kato (U.S. Pat. No. 6,822,096), who utilized the luminescence change from the invisible near-infrared to the visible red of binuclear platinum (II) complexes. However, these complexes only shift the emitted wavelength out of the visible spectrum.

Fluorescent materials, including inorganic semiconductor quantum dots, organic and metallorganic dyes, dye-doped silica or polymer particles, have currently attracted great attention in a wide variety of high-technology applications such as high-throughput screening, ultra-sensitive assays, optoelectronics, and living cell imaging. Colloidal quantum dots (hundreds to thousands of atoms) are traditionally made from crystals of IIA-VIA or IIIB-VB elements (PbS, CdSe, etc.) or other semiconductors. The heavy metals therein are intrinsically toxic to the researchers and the experimental systems (e.g., living cells), as well as generating a toxic waste stream into the environment. Organic and metallorganic dyes generally consist of π-conjugated ring structures such as xanthenes, pyrenes or cyanines, with emissions across the spectrum from UV to the near infrared (~300-900 nm) and may be fine tuned to particular wavelengths or applications by changing the chemistry of their substituent groups. The size of individual dye molecules is very small (~1 nm), which causes non-specific labeling and high background signals as dyes diffuse away from their intended targets. Spectrally, organic dyes tend to have fairly wide absorption and emission spectra (FWHM ~50 nm), which can lead to spectral overlap and re-absorption when using multiple dye species simultaneously. In normal use, dye molecules are exposed to a variety of harsh environments and often suffer from photobleaching and quenching due to the interactions with solvent molecules and reactive species such as oxygen or ions dissolved in solution.

In order to create more robust emitters with enhanced brightness and stability, researchers have developed composite nano- and micro-particles consisting of dye molecules and silica or polymer matrix. Thus the encapsulated dye molecules can be protected from external perturbations, with reducing stochastic blinking, photobleaching, and quenching. Dye-loaded polymer particles are superior to their silica counterpart in terms of the versatile chemical compositions, tunable surface chemistry suited for biocompatibility and bioconjugation, facile preparation, and easy control of the particle size and size distribution.

Gao et al. have incorporated pyrene dyes into polystyrene particles using a normal microemulsion approach, leading to a 40-fold increase in emission intensity with respect to the pure dye at the identical concentration (H. Gao et al., Colloid Polym. Sci. 2002, 280, 653). Dinsmore et al. swelled poly (methyl methacrylate) particles and absorbed a rhodamine dye into them for usage in a confocal microscopic study of colloidal dispersions (A. D. Dinsmore et al., Appl. Opt. 2001, 40, 4152). U.S. Pat. No. 5,716,855 disclosed fluorescent particles containing anthracene- or naphthacene-derivatived dyes aiming to the application as biological markers.

Up to now, most of the organic dyes commercially available, including the above mentioned dyes as well as ethidium bromide (U.S. Pat. No. 4,729,947, U.S. Pat. No. 5,346,603, U.S. Pat. No. 6,143,151, and U.S. Pat. No. 6,143,153), Nile red (U.S. Pat. No. 6,897,297 and U.S. Pat. No. 6,465,208), fluorescamine (U.S. Pat. No. 4,203,967), o-phthaldialdehyde (U.S. Pat. No. 6,969,615 and U.S. Pat. No. 6,607,918), Cyanine dyes (U.S. Pat. No. 5,627,027 and U.S. Pat. No. 5,410,030), etc. are emissive only in their solution state, whereas emission is quenched in aggregation states (e.g., high dye concentration state, film state, solid state, etc.). This is attributed to the mechanism of nonradiative energy transfer between the closely packed chromophores, thus resulting in self-quenching of the fluorescence. Thus, the loading concentration of dyes in the polymer particles cannot be sufficiently high and accordingly the intensity of fluorescence is considerably limited.

With respect to the polymers for dye encapsulation, the currently available species are mainly hydrophobic polystyrene and less hydrophobic poly(methyl methacrylate), as mentioned hereinabove. The hydrophobic nature of these particles commonly leads to clustering and non-specific binding of biological materials, which considerably limits their application in aqueous environment of biology and other fields. Additionally, these particles are prepared and dispersed in organic solvent. For example, Hu et al. prepared poly(methyl methacrylate) fluorescent particles through dispersion polymerization in the mixture of hexane and ethanol (H. Hu et al., Langmuir 2004, 20, 7436). The solvent-dispersible polymer particles are difficult to disperse stably in aqueous media.

The presently described series of linear and cyclic π-conjugated organic compounds (hereinafter polyenes) have been designed and synthesized with different chromophores including tetraphenylethylene, siloles, fulvene, butadienes, and 4H-pyrans. The emission color of these new polyenes ranges from blue to red arising from the different chromophoric structures. Their fluorescent behavior features the aggregation-induced emission (AIE) phenomenon, which turns the dyes from faint-emitters when molecularly dissolved into strong luminophors when aggregated or in the solid state. All these features make the presently described AIE-active molecules excellent candidates for use as bioprobes for DNA detection, G-quadruplex identification and potassium-ion sensing as well as in polymeric particles, sensors and detection devices. In addition, the AIE-active-molecules can be used to study conformational structures, folding processes and as fluorescent markers to visualize DNA bands in assays.

SUMMARY OF THE INVENTION

The presently described subject matter is directed to water-soluble conjugated polyenes which exhibit aggregation induced emission and are useful as bioprobes and for manufacturing sensors. The emission color of these water-soluble conjugated polyenes ranges from blue to red arising from the different chromophoric structures. They exhibit aggregation-induced emission (AIE) (i.e., increased fluorescence) upon addition of a non-aqueous solvent. Their luminescent behavior features the aggregation-induced emission (AIE) phenomenon, which turns the dyes (water-soluble conjugated polyenes) from faint-emitters when molecularly dissolved in an aqueous solvent, i.e., water, into strong luminophors when aggregated or in the solid state. Stated differently, when the compounds are dissolved in aqueous solvents, they are substantially nonemissive ("off") while when a non-aqueous solvent is added, they aggregate and emit intensely ("on"). The quantum efficiency increases when the amount of non-aqueous solvent is increased. The presently described water-soluble conjugated polyene compounds are useful as "turn-on" fluorescence sensors. In addition, the presently described subject matter is directed to water-dispersible fluorescent polymer particles, i.e., micro-particles and/or nano-particles, comprising the described water-soluble conjugated polyenes, for example, a tetraphenylethylene ("TPE").

In an embodiment, the present subject matter relates to a water-soluble conjugated polyene compound comprising a backbone structure of a formula selected from the group consisting of:

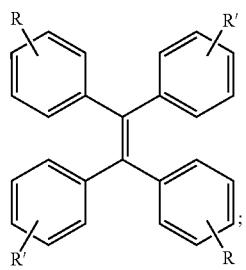

I

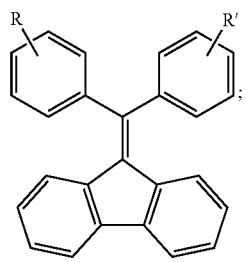

II

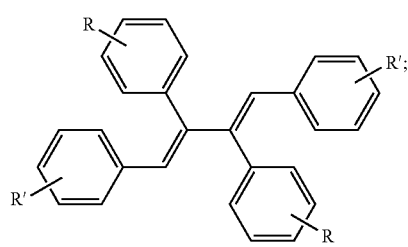

III

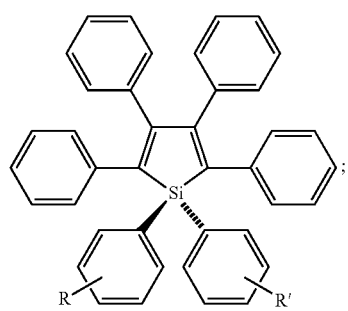

IV

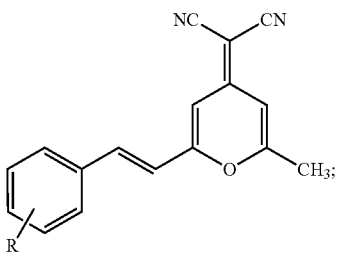

V

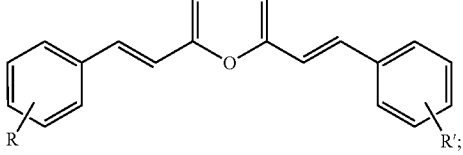

VI

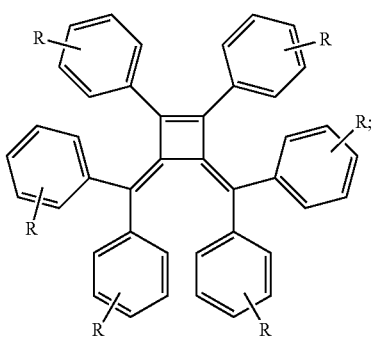

VII

Cyclobutene

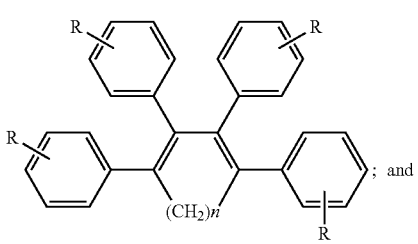

VIII

; and

Cyclobutadiene

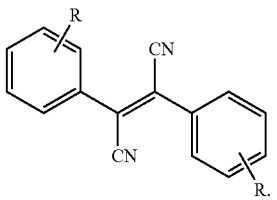

IX 2,3-diphenylfumaronitrile wherein

R and R' are independently selected from H, X, $B(OH)_2$, $(X)_nCOOR''$, $(X)_nCOOH$, $(X)_nNH_2$, $(X)_nNHR''$, $(X)_nNR''_2$, $(X)_nN{+}R''_3Br^-$, $(X)_nOH$, $(X)_nSH$, $(X)_nSO_3{^-}Na^+$,

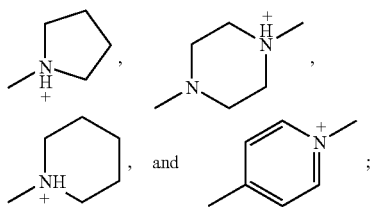

X is selected from $(CH_2)_n$, $O(CH_2)_n$, $NH(CH_2)_n$, $N[(CH_2)_n]_2$, and $(OCH_2CH_2)_n$; and R" is selected from R, R', $(CH_2)_nCH_3$, CONH—X—, COO—X—, $C_6H_5$—R, —$CH_2$—$C_6H_5$, and $C_6H_5$;

and wherein n=0 to 20, and the compound is water-soluble and exhibits aggregation induced emission.

In an embodiment, the present subject matter relates to a water-soluble conjugated polyene compound, wherein the compound does not exhibit aggregation induced quenching.

In an additional embodiment, the present subject matter relates to a method for detecting the presence or absence of a target biomacromolecule in a biological sample, comprising contacting the biological sample with the water-soluble conjugated polyene compound, and detecting luminescence.

In a further embodiment, the present subject matter relates to a method for detecting the presence or absence of a target biomacromolecule in a biological sample, wherein the biological sample is selected from the group consisting of a tissue sample, a cell sample, blood, saliva, spinal fluid, lymph fluid, vaginal fluid, seminal fluid, and urine.

In an embodiment, the present subject matter relates to a sensor device for detecting the presence or absence of a target biomacromolecule, comprising a holder and a detecting molecule comprising the water-soluble conjugated polyene compound, the detecting molecule being held in place by the holder and being accessible to the target molecule or substance.

In a further embodiment, the present subject matter relates to a sensor device, wherein the luminance of the detecting molecule increases upon contact with the target biomacromolecule.

In another embodiment, the present subject matter relates to a sensor device, wherein the holder is a container and the detecting molecule is disposed inside the container; the container having one or more openings or orifices to allow access to the detecting molecule by the target molecule.

In yet another embodiment, the present subject matter relates to a sensor device, wherein the holder is a surface on which the detecting molecule is coated in a thin film.

In an embodiment, the present subject matter relates to water-dispersible, fluorescent, polymeric particles, comprising or consisting of a water-soluble conjugated polyene compound of formula VII; and a polymer comprising one or more ethylenically unsaturated monomers.

In another embodiment, the present subject matter relates to a method of detecting G-quadruplex formation, DNA, or protein and protein levels in a biological sample comprising contacting the biological sample with the water-soluble conjugated polyene compound and detecting luminescence.

In another embodiment, the present subject matter relates to a method of detecting G-quadruplex formation, DNA, or protein and protein levels wherein the conjugated polyene compound forms a complex with G-rich strand sequences of the biological sample which activates the fluorescence of the polyene.

In a further embodiment, the present subject matter relates to a method of detecting G-quadruplex formation, DNA, or protein and protein levels wherein a cation is added to the biological sample and polyene mixture.

In another embodiment, the present subject matter relates to a method of detecting G-quadruplex formation fluorescence emission intensity is monitored for any spectral shifts signaling the presence of a G-quadruplex conformation in the folded oligonucleotide.

In a further embodiment, the present subject matter relates to a method of detecting G-quadruplex formation, DNA, or protein and protein levels in a biological sample wherein the biological sample is selected from the group consisting of a tissue sample, cell sample, blood, saliva, spinal fluid, lymph fluid, vaginal fluid, seminal fluid, and urine.

In another embodiment, the present subject matter relates to a method of detecting G-quadruplex formation, DNA, or protein and protein levels in a biological sample wherein the biological sample is urine.

In another embodiment, the present subject matter relates to a method of detecting G-quadruplex formation, DNA, or protein and protein levels in a biological sample wherein the protein being detected in the biological sample is human serum albumin.

In an embodiment, the present subject matter relates to a method of diagnosing a kidney disorder comprising contacting a biological sample with a water-soluble conjugated polyene compound and detecting luminescence.

In another embodiment, the present subject matter relates to a method of diagnosing a kidney disorder wherein the conjugated polyene compound forms a complex with proteins in the biological sample thereby causing the conjugated polyene compound to fluoresce wherein the luminescence levels indicate the levels of protein present in the biological sample.

In yet another embodiment, the present subject matter relates to a method of diagnosing a kidney disorder wherein the protein being detected in the biological sample is human serum albumin.

In a further embodiment, the present subject matter relates to a method of detecting guanine (G)-rich repeat sequences in a biological sample comprising running the biological sample through a poly(acrylamide) gel electrophoresis (PAGE) assay, staining the PAGE assay with a water-soluble conjugated polyene compound, and detecting luminescence.

BRIEF DESCRIPTION OF DRAWINGS

FIG. 1A-C shows that the three TPE derivatives are practically nonemissive when dissolved but highly emissive when aggregated.

FIG. 2A illustrates the change of fluorescence spectrum of TPE-OH.Na2 (5 μM) with addition of BSA in aqueous phosphate buffer (pH=7.0).

FIG. 2B illustrates a plot of fluorescence intensity at 476 nm versus BSA concentration.

FIG. 2C illustrates the linear region of the binding isotherm of TPE-OH to BSA. The FL of TPE-OH is turned on in the presence of BSA (FIG. 2). Its intensity increased with increasing BSA concentration, and in the BSA concentration range of 0-10 μg/ml exhibited a linear relationship with a $R^2$ value of 0.9974.

FIGS. 5 and 6 illustrate that the FL of cationic TPE derivatives in aqueous solution can is turned on in the presence of BSA or DNA. TPE-C2N$^+$ exhibits better affinity to ctDNA than BSA while TPE-C4N$^+$ gives the opposite result.

FIG. 9 illustrates that N+C2-TPE-C2N+ has larger affinity to DNA than to RNA and proteins.

FIG. 12A illustrates the emission spectra of derivative 4 (2.5 μM) in an aqueous phosphate buffer (pH=7) and in the buffers containing 300 μg ml$^{-1}$ ct DNA and 500 μg ml$^{-1}$ BSA.

FIG. 12B illustrates plots of fluorescence intensities of buffer solutions of derivative 4 at 463 nm vs. concentrations of ct DNA and BSA.

FIG. 13A illustrates the absorption and emission spectra of derivative 4 (2.5 μM) in water and a glycerol-water mixture at 25° C.

FIG. 13B illustrates the emission spectra of derivative 4 (2.5 μM)

FIG. 19A is a photograph of the coating film of Example 25 formed by the polymer nanoparticle dispersion with and without (controls) TPE-COOH fluorophores. The photos were taken under 365 nm irradiation from a UV lamp.

FIG. 19B is a photograph of the flexible thin sheets of Example 26 formed by the polymer nanoparticle dispersion with and without (controls) TPE-COOH fluorophores. The photos were taken under 365 nm irradiation from a UV lamp.

FIG. 32A shows the emission spectra of TTAPE in a Tris-HCl buffer in the presence of G1 and $K^+$.

FIG. 32B shows the effects of [$K^+$] on emission intensity at 470 nm and peak wavelength ($\lambda_{em}$) of the TTAPE/G1 solution. [TTAPE]=4.5 μM, [G1]=9 μM; $\lambda_{ex}$=350 nm.

FIG. 38A shows the emission spectra of buffer solutions (pH=7.50) of TTAPE/C1 in the absence and presence of metal ions. [TTAPE]=4.5 μM, [ion]=0.5 M; $\lambda_{ex}$=350 nm; [C1]=9 μM.

FIG. 38B shows the emission spectra of buffer solutions (pH=7.50) of (A) TTAPE/C1 and (B) TTAPE/G1/C1 in the absence and presence of metal ions. [TTAPE]=4.5 μM, [ion]= 0.5 M; $\lambda_{ex}$=350 nm; [G1]=[C1]=4.5 μM.

DETAILED DESCRIPTION OF PARTICULAR EMBODIMENTS

Definitions

Figures 1A, 1B, 1C:
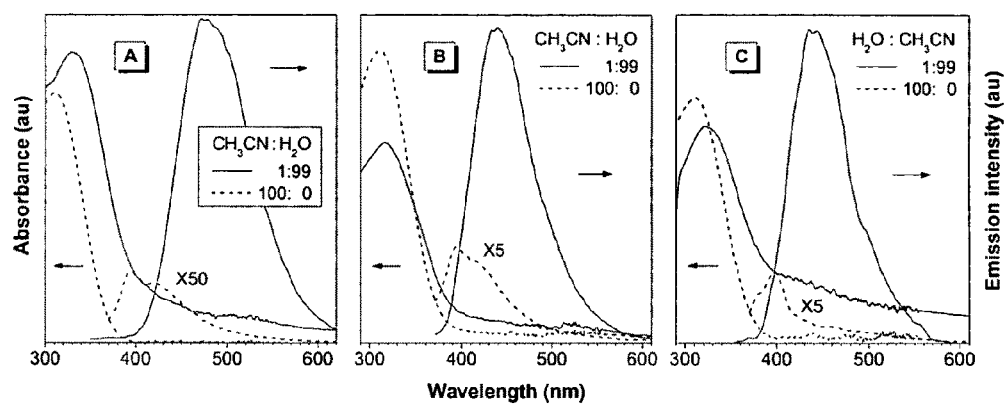
FIGS. 1A, 1B, and 1C illustrate absorption and emission spectra of (A) TPE-OMe (10 μM), (B) TPE-OH (10 μM), and (C) TPE-SO3 (5 μM) in pure acetonitrile, pure water, and mixtures of acetonitrile and water.
Figures 3A, 3B, 3C:
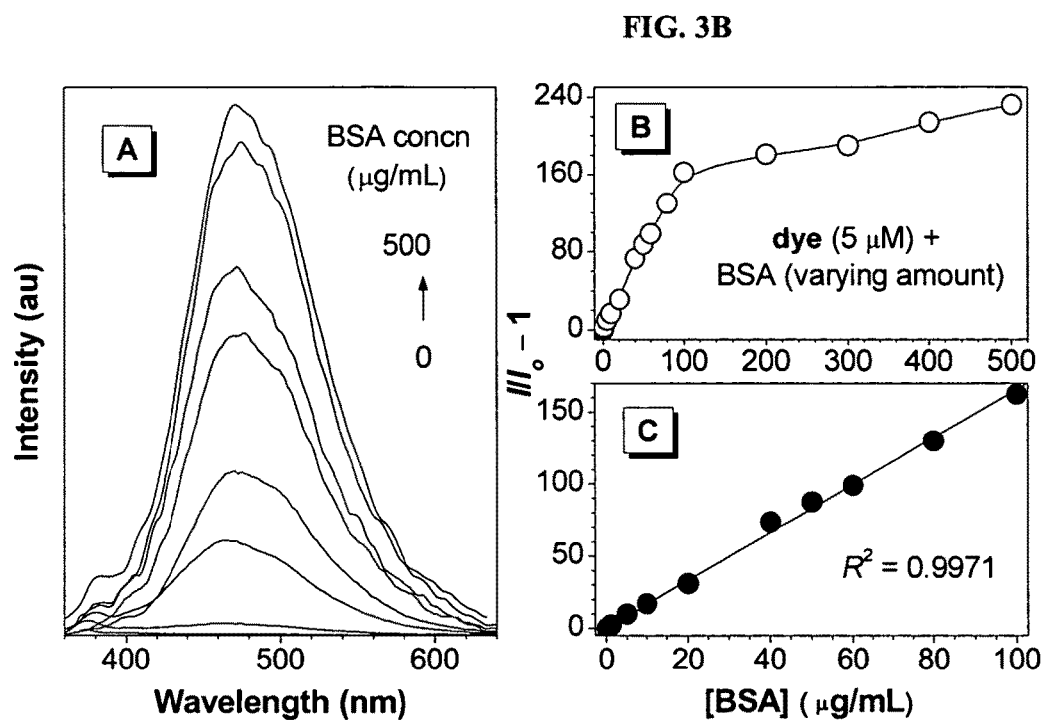
FIG. 3A illustrates the change of FL spectrum of TPE-SO3 with addition of BSA in an aqueous phosphate buffer.
FIG. 3B illustrates the plot of FL intensity at 472 nm versus BSA concentration.
FIG. 3C illustrates the linear region of the $(I/I_0-1)$-[BSA] plot in FIG. 3B. TPE-SO3 shows similar behavior as TPE-OH but better performance. The FL intensity increase up to 240 times upon binding with BSA. Linear range in the BSA concentration from 0 to 100 μg/ml is given with a $R^2$ value of 0.9971.
Figures 4A, 4B:
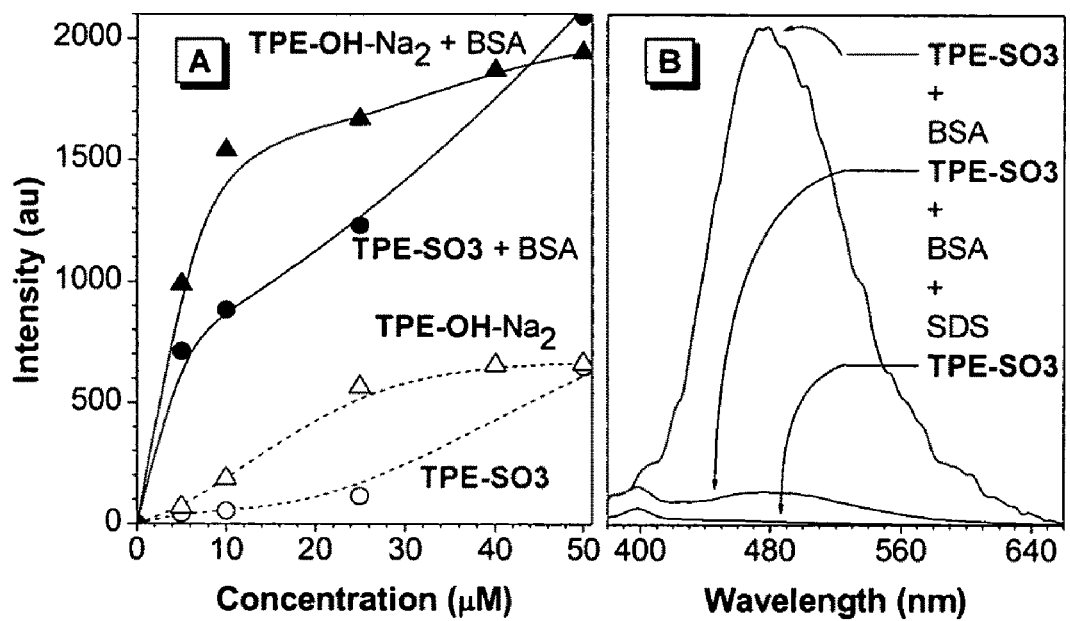
FIG. 4A illustrates the effect of dye concentration on the FL intensity of buffer solution of TPE-OH.Na2 at 467 nm or TPE-SO3 at 472 nm in the absence or presence of BSA (10 μg/ml).
FIG. 4B illustrates the effect of BSA (100 μg/ml) and/or SDS (1 mg/ml) on the FL spectrum of a buffer solution of TPE-SO3 (5 μM). Conventional fluorescent dyes suffer from self-quenching at high dye concentrations, whereas the FL of the AIE-active dyes is intensified with increasing dye concentration as illustrated in FIG. 4A. The FL of TPE-SO3 solution in the presence of BSA is diminished by adding surfactants such as sodium dodecyl sulphate (SDS) in high concentration (1 mg/ml) as illustrated in FIG. 4 B.
Figure 5A:
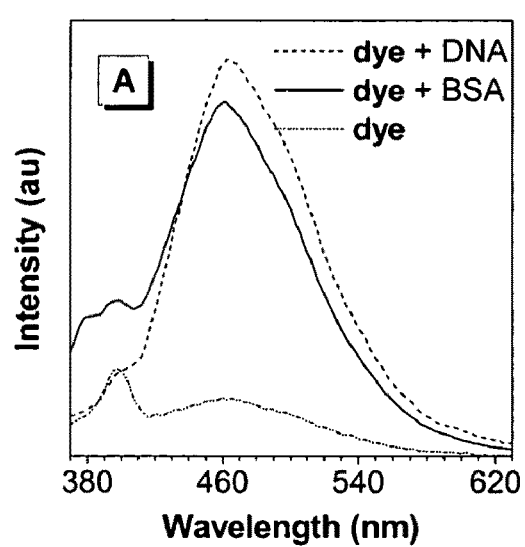
FIG. 5A illustrates the emission spectra of TPE-C2N$^+$ (2.5 μM) in an aqueous phosphate buffer (pH=7) and in the buffers containing 300 μg/ml BSA.
Figure 5B:
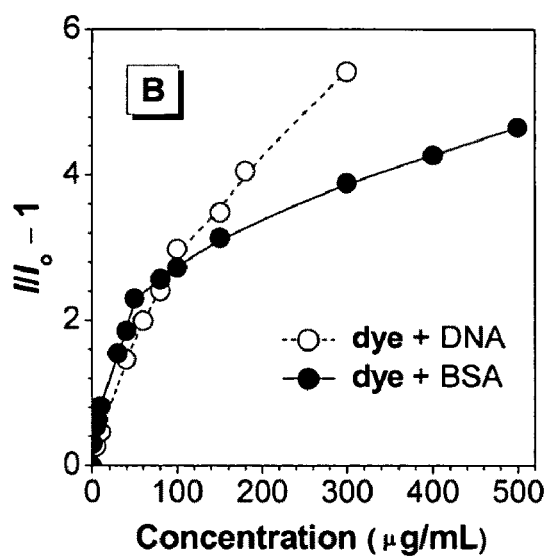
FIG. 5B illustrates a plot of fluorescence intensities of buffer solutions of TPE-C2N$^+$ at 462 nm versus concentrations of DNA and BSA.
Figure 6A:
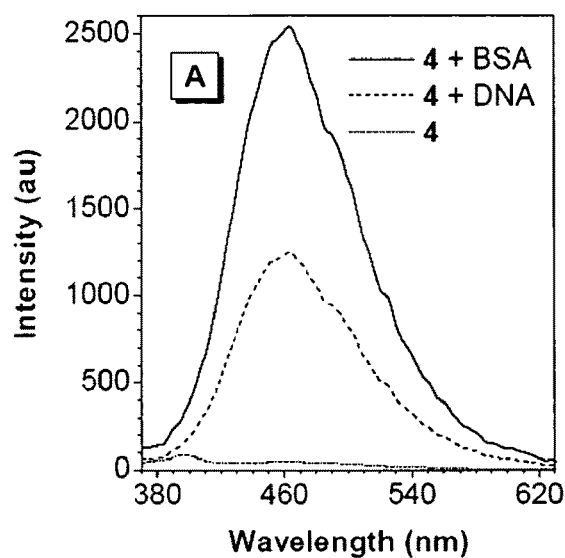
FIG. 6A illustrates the emission spectra of TPE-C4N$^+$ (4) (2.5 μM) in an aqueous phosphate buffer (pH=7) and in the buffers containing 300 μg/ml calf thymus DNA ("ctDNA") and 500 μg/ml BSA.
Figure 6B:
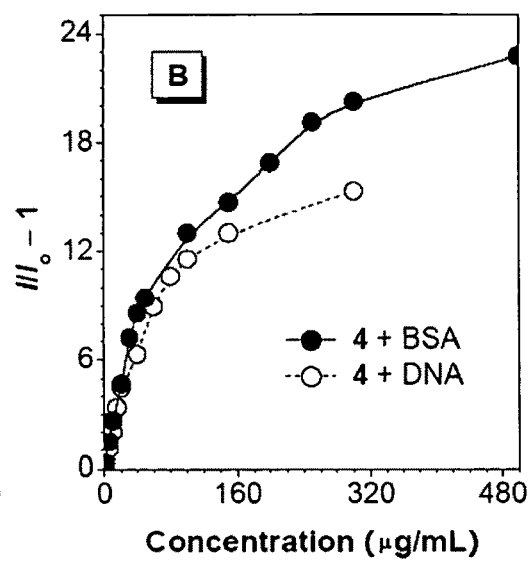
FIG. 6B illustrates plots of fluorescence intensities of buffer solutions of TPE-C4N$^+$ (4) at 463 nm versus concentrations of ct DNA and BSA.
Figure 7A:
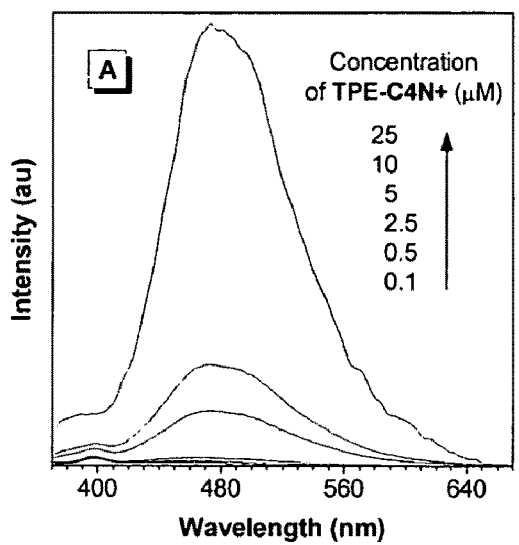
FIG. 7A illustrates the emission spectra of TPE-C4N+ (2.5 μM) in an aqueous phosphate buffer (pH=7) and in buffers containing 300 μg/ml ctDNA and 500 μg/ml BSA.
Figure 7B:
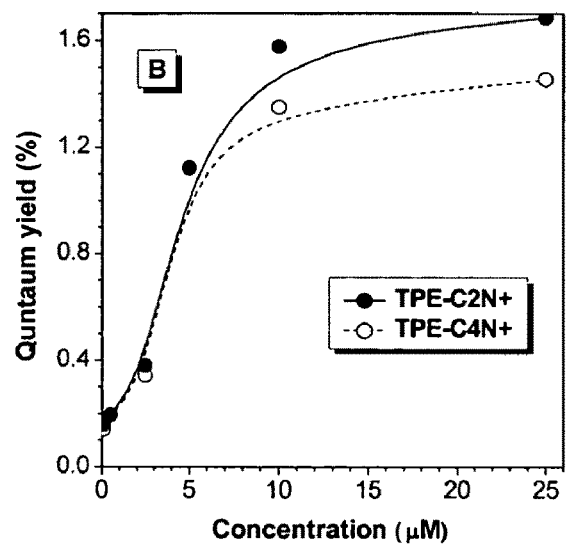
FIG. 7B illustrates plots of fluorescence intensities of buffer solutions of TPE-C4N+ at 463 nm versus concentrations of ctDNA and BSA. The FL of TPE-C4N+ and TPE-C2N+ is intensified with increased dye concentration.
Figure 8:
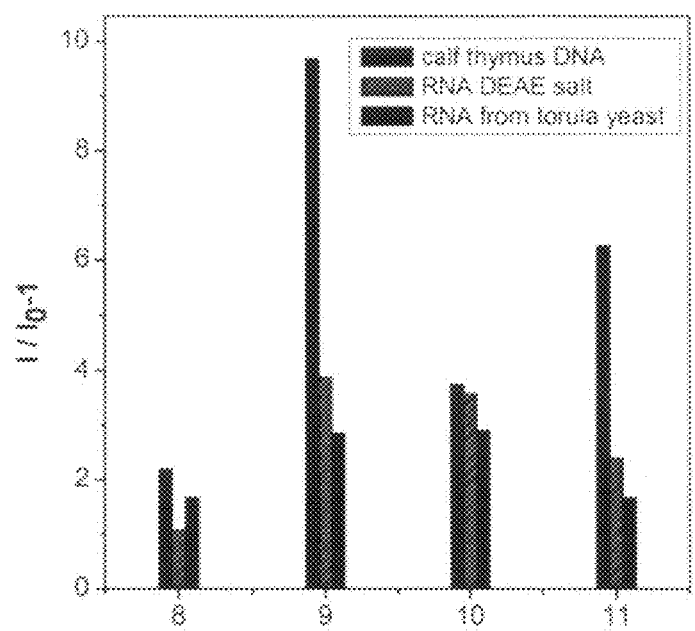
FIG. 8 illustrates increments of fluorescence of TPE-C2N+ (8), N+C2-TPE-C2N+ (9), TPE-C4N+ (10), N+C4-TPE-C4N+ (11) when binding with 10 μg/ml ctDNA/10 μg/ml RNA diethylaminoethanol (DEAE) salt from torula yeast/10 μg/ml RNA from torula yeast in buffer solution pH=7. Concentration of dyes: 5 μM; excitation wavelength: 350 nm. The four cationic TPE derivatives display larger FL enhancement in the presence of DNA than that of RNA. Meanwhile N+C2-TPE-C2N+ and N+C4-TPE-C4N+ show much larger variety of FL than that of TPE-C2N+ and TPE-C4N+ in the presence of DNA and RNA.
Figure 9:
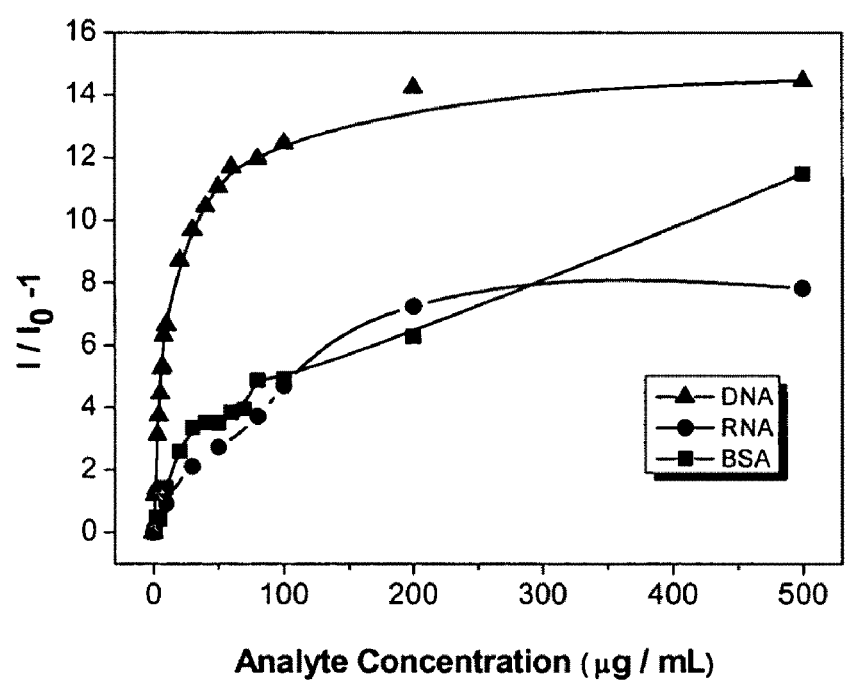
FIG. 9 illustrates the binding isotherm of N+C2-TPE-C2N+ (5 μM) to ctDNA/RNA from torula yeast/BSA (plot of the fluorescence intensity at 470 nm for ctDNA/RNA, and at 467 nm for BSA) in aqueous phosphate buffer (pH=7.0).
Figure 10:
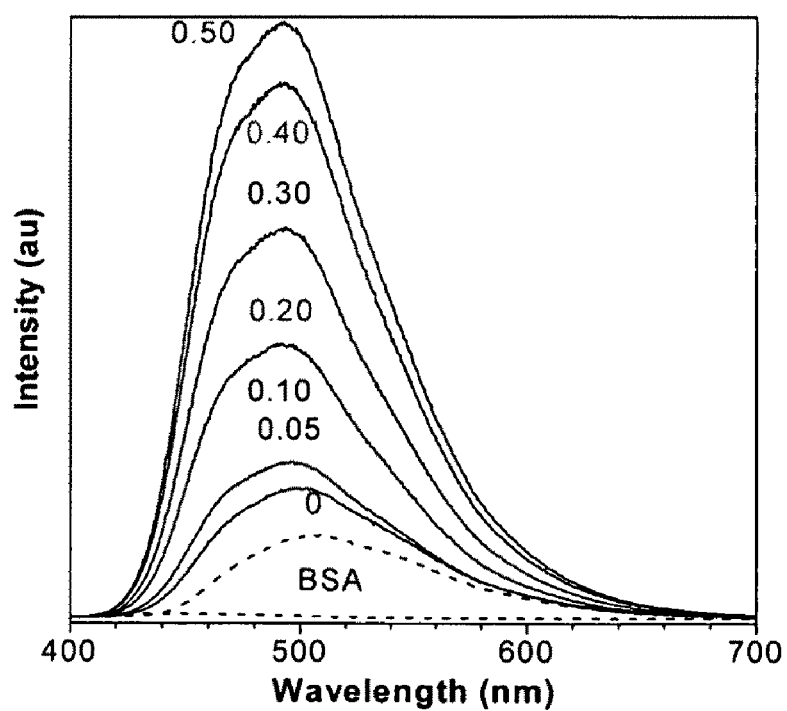
FIG. 10 illustrates the photoluminescence spectra of the water/methanol (6:4) solutions of a PPS-OH ($5.7\times10^{-5}$ M) in the presence of KOH ($8.4\times10^4$ M) and BSA. The spectrum of a "pure" BSA solution (0.50 wt %) is shown for comparison. Excitation wavelength: 378 nm. Water-soluble silole derivatives also show this "turn-on" property when binding to BSA in aqueous solutions.

The following definitions are provided for the purpose of understanding the present subject matter and for constructing the appended patent claims.

It is noted that, as used in this specification and the appended claims, the singular forms "a," "an" and "the" include plural references unless the context clearly dictates otherwise.

"A chemically conjugated system" means a system of atoms covalently bonded with alternating single and double bonds in a molecule of an organic compound.

"A polyene" means a molecule of an organic compound containing more than one alkene. For example, a diene has two C=C; a triene has three C=C; etc.

"Target molecule" means the molecule whose changes in concentration in an environment are intended to be detected by a sensor. A target molecule can comprise or consist of a biomacromolecule. "Detecting molecule" means a molecule which, upon contacting with a target molecule in the environment, can provide a signal perceivable to human.

"Alkyl" means, unless otherwise specified, an aliphatic hydrocarbon group which may be straight or branched chain having about 1 to about 15 carbon atoms in the chain, optionally substituted by one or more halogen atoms. A particularly suitable alkyl group has from 1 to about 6 carbon atoms. The term "unsaturated" refers to the presence of one or more double and triple bonds between atoms of a radical group, for example.

"Heteroatom" means an atom selected from the group consisting nitrogen, oxygen, sulfur, phosphorus, boron and silicon.

"Heteroaryl" as a group or part of a group denotes an optionally substituted aromatic monocyclic or multicyclic organic moiety of about 5 to about 10 ring members in which at least one ring member is a heteroatom.

"Cycloalkyl" means an optionally substituted non-aromatic monocyclic or multicyclic ring system of about 3 to about 10 carbon atoms.

"Heterocycloalkyl" means a cycloalkyl group of about 3 to 7 ring members in which at least one ring member is a heteroatom.

"Aryl" as a group or part of a group denotes an optionally substituted monocyclic or multicyclic aromatic carbocyclic moiety of about 6 to about 14 carbon atoms, such as phenyl or naphthyl.

"Heteroalkyl" refer to alkyl in which at least one carbon atom is replaced by a heteroatom.

"Biomacromolecule" means a high molecular biological weight substance comprising or consisting of one or more of nucleic acids, proteins and/or complex carbohydrates.

"Microparticle" means any microscopic particle or particle population having a mean diameter of less than about 10 microns (μm); less than about 5 μm; less than about 1 μm; or having a mean diameter in the range of from greater than or equal to 10 nm to less than 5 μm; of from greater than or equal to 40 nm to less than 3 μm; of from greater than or equal to 50 nm to less than 1 μm; of from greater than or equal to 60 nm to less than 750 nm; of from greater than or equal to 60 nm to less than 500 nm; of from greater than or equal to 60 nm to less than 300 nm; of from greater than or equal to 80 nm to less than or equal to 250 nm; of from greater than or equal to 1 μm to less than 10 μm; of from greater than or equal to 2.5 μm to less than 10 μm; of from greater than or equal to 5 μm to less than 10 μm; of from greater than or equal to 7.5 μm to less than 10 μm; of from greater than or equal to 2.5 μm to 7.5 μm; or having a mean diameter in the range of from greater than or equal to 5 μm to 7.5 μm. In an embodiment, greater than 99% of the microparticles of a microparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 20% of the microparticles have a mean diameter falling within a described range; or greater than about 10% of the microparticles have a mean diameter falling within a described range.

"Nanoparticle" means any microscopic particle or particle population having a mean diameter of less than about 100 nanometers (nm); less than about 90 nm; less than about 80 nm; less than about 70 nm; less than about 60 nm; less than about 50 nm in diameter; or having a mean diameter of from 1 nm to less than 100 nm; from 10 nm to less than 100 nm; from 20 nm to less than 100 nm; from 30 nm to less than 100 nm; from 40 nm to less than 100 nm; from 50 nm to less than 100 nm; from 10 nm to 90 nm; from 20 to 80 nm; or having a mean diameter of from 30 to 70 nm. In an embodiment, greater than 99% of the nanoparticles of a nanoparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 20% of the microparticles have a mean diameter falling within a described range; or greater than about 10% of the microparticles have a mean diameter falling within a described range.

"Aggregation-induced emission" means the fluorescence/phosphorescence is turned on upon aggregation formation or in the solid state. When molecularly dissolved, the material is nonemissive. However, the emission is turned on when the intramolecular rotation is restricted.

"Bathochromic shift" means a change of spectral band position in the absorption, reflectance, transmittance, or emission spectrum of a molecule to a longer wavelength (lower frequency) due to the influence of substitution or a change in environment. It is informally referred to as a red shift and is opposite to hypsochromic shift.

"Emission intensity" means the magnitude of fluorescence/phosphorescence normally obtained from fluorescence spectrometer, fluorescence microscopy measurement.

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Water-Soluble Conjugated Polyenes
Examples of water-soluble conjugated polyene functional AIE-active compounds
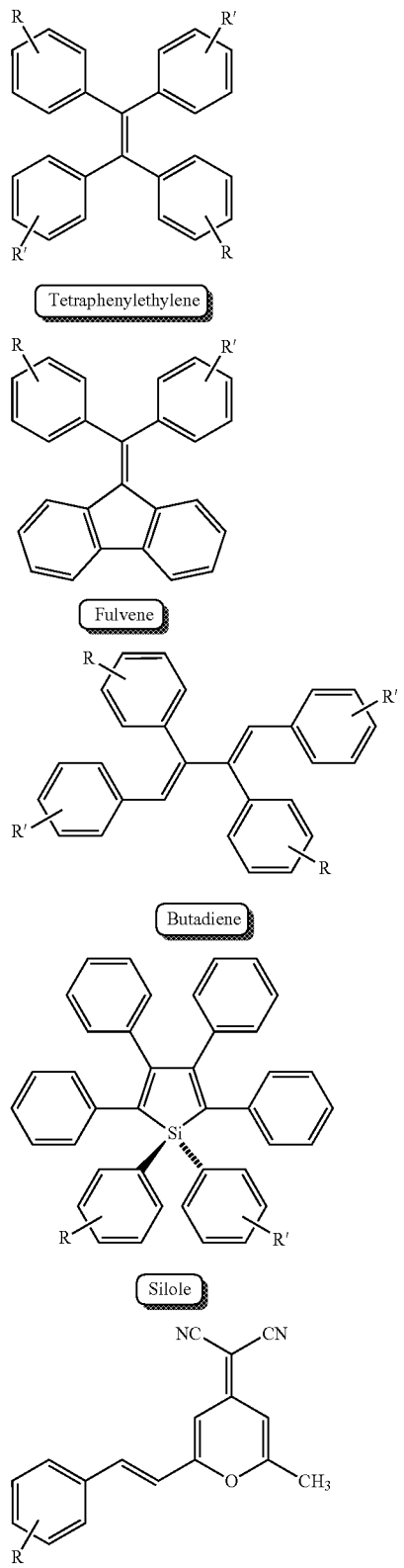
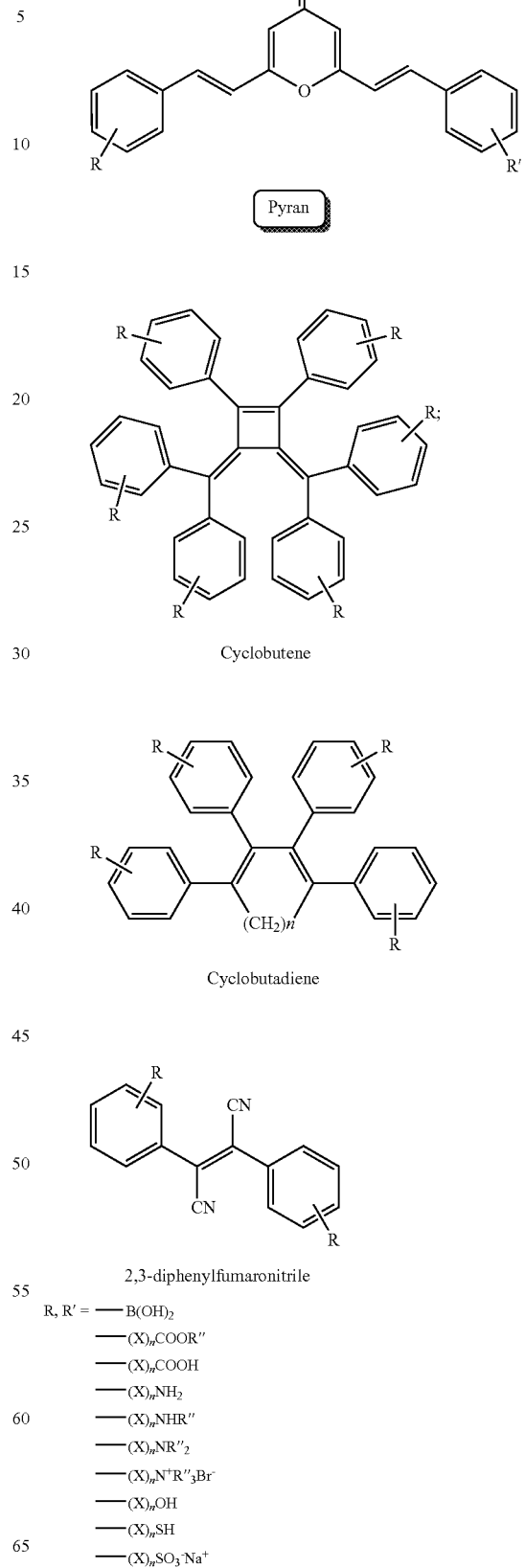

-continued
X = 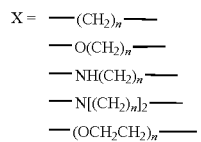
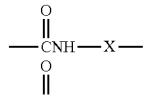
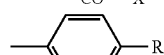
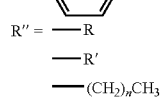
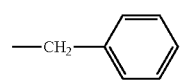
R'' = 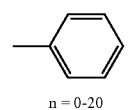
n = 0-20
R, R' can also =
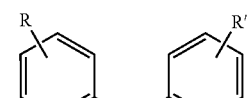
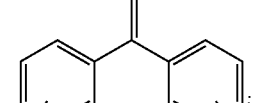
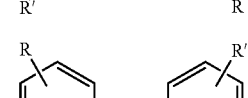
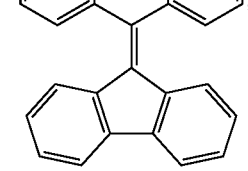
In an embodiment, the present subject matter relates to a water-soluble conjugated polyene compound comprising a backbone structure of a formula selected from the group consisting of:
I
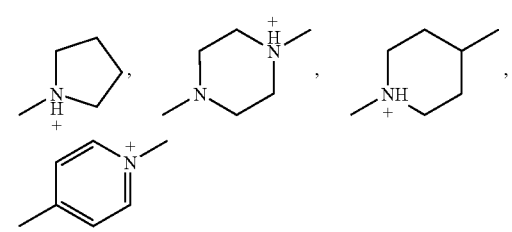
II
III
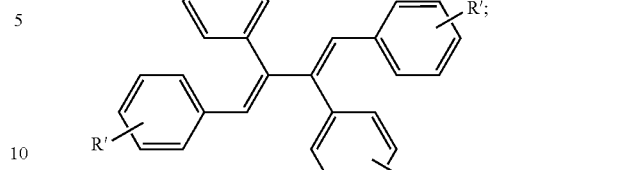
IV
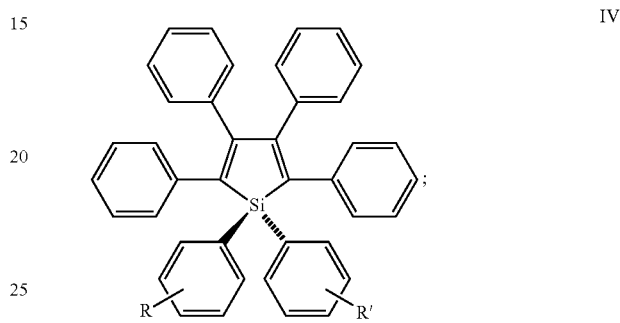
V
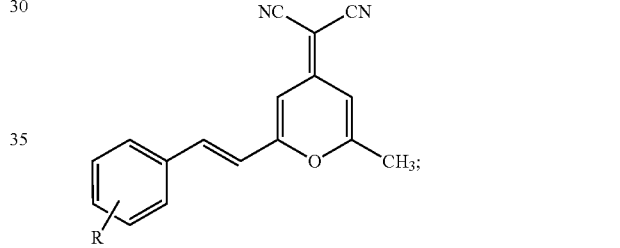
VI
VII
Cyclobutene -continued

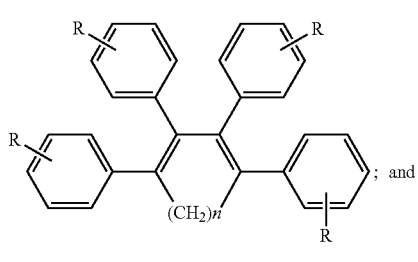

Cyclobutadiene

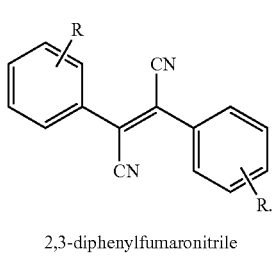

2,3-diphenylfumaronitrile wherein
R and R' are independently selected from H, X, $B(OH)_2$, $(X)_nCOOR''$, $(X)_nCOOH$, $(X)_nNH_2$, $(X)_nNHR''$, $(X)_nNR''_2$, $(X)_nN+R''_3Br^-$, $(X)_nOH$, $(X)_nSH$, $(X)_nSO_3^-Na^+$,

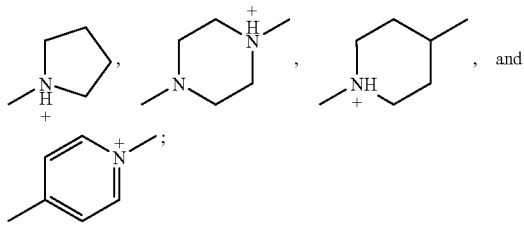

X is selected from $(CH_2)_n$, $O(CH_2)_n$, $NH(CH_2)_n$, $N[(CH_2)_n]_2$, and $(OCH_2CH_2)_n$; and R" is selected from R, R', $(CH_2)_nCH_3$, CONH—X—, COO—X—, $C_6H_5$—R, —$CH_2$—$C_6H_5$, and $C_6H_5$;

and wherein n=0 to 20, and the compound is water-soluble and exhibits aggregation induced emission.

In another embodiment, the present subject matter relates to a water-soluble conjugated polyene compound, wherein the molecule has a backbone structure of formula I.

In an embodiment, the present subject matter relates to a water-soluble conjugated polyene compound of claim formula I, wherein R is H and R' is selected from the group consisting of H, OH, COOH, $CH_2NH_2$, $B(OH)_2$, $O(CH_2)_3SO_3^-Na^+$, $O(CH_2)_2N^+(CH_2CH_3)_3Br^-$, $O(CH_2)_4N^+(CH_2CH_3)_3Br^-$, and $N^+OCH_3$.

In a further embodiment, the present subject matter relates to a water-soluble conjugated polyene compound of formula I, wherein R and R' are the same and are selected from the group consisting of OH, $O(CH_2)_2N^+(CH_2CH_3)_3Br^-$, and $O(CH_2)_4N^+(CH_2CH_3)_3Br^-$.

The presently described subject matter is also directed to a water-soluble conjugated polyene compound of formula I, selected from the group consisting of
1,2-Bis(4-hydroxyphenyl)-1,2-diphenylethylene;
1,2-Bis(4-methoxyphenyl)-1,2-diphenylethylene;
1,2-diphenyl-1,2-bis(4,4'-(3-sulfonato)propoxyl)phenylethylene;

N,N'-[1,2-diphenyl-1,2-bis(1,4-phenoxyethyl)vinyl]bis(triethylammonium bromide);
N,N'-[1,2-diphenyl-1,2-bis(1,4-phenoxybutyl)vinyl]bis(triethylammonium bromide);
1,1,2,2-tetrakis(4-hydroxyphenyl)ethylene;
N,N',N'',N'''-[1,2-tetrakis(1,4-phenoxybutyl)vinyl]tetrakis(triethylammonium bromide);
N,N',N'',N'''-[1,2-tetrakis(1,4-phenoxyethyl)vinyl]tetrakis(triethylammonium bromide);
4,4'-(1,2-diphenylvinyl)di(phenylboronic acid);
4,4'-(1,2-diphenylvinyl)di(phenylcarboxylic acid); and
1,2-di[4-(aminomethyl)phenyl]-1,2-diphenylethylene.

In another embodiment, the present subject matter relates to a water-soluble conjugated polyene compound wherein the molecule has a backbone structure of formula II.

In yet another embodiment, the present subject matter relates to a water-soluble conjugated polyene compound wherein the molecule has a backbone structure of formula III.

In a further embodiment, the present subject matter relates to a water-soluble conjugated polyene compound wherein the molecule has a backbone structure of formula IV.

In an embodiment, the present subject matter relates to a water-soluble conjugated polyene compound of formula IV, wherein R is H and R' is selected from the group consisting of $CH_2N^+(CH_2CH_3)_2Br^-$ and $CH_2N(CH_2CH_3)_2$.

In another embodiment, the present subject matter relates to a water-soluble conjugated polyene compound of formula IV, selected from the group consisting of
1,1'-Bis-[4-(N,N'-diethylaminomethyl)phenyl]-2,3,4,5-tetraphenylsilole; and
N,N'-[1,1'-bis(1,4-benzylene)-2,3,4,5-tetraphenylsilolyl)bis(triethylammonium bromide).

In yet another embodiment, the present subject matter relates to a water-soluble conjugated polyene compound, wherein the molecule has a backbone structure of formula V.

In a further embodiment, the present subject matter relates to a water-soluble conjugated polyene compound, wherein the molecule has a backbone structure of formula VI.

Synthesis of Water-Soluble Conjugated Polyenes

In one embodiment, the present subject matter relates to water-soluble conjugated polyenes useful as bioprobes and for manufacturing sensors. These polyenes can be prepared according to a variety of different methods. Non-limiting examples of such synthetic methods are discussed below.

Scheme 1. Synthesis of TPE derivatives.

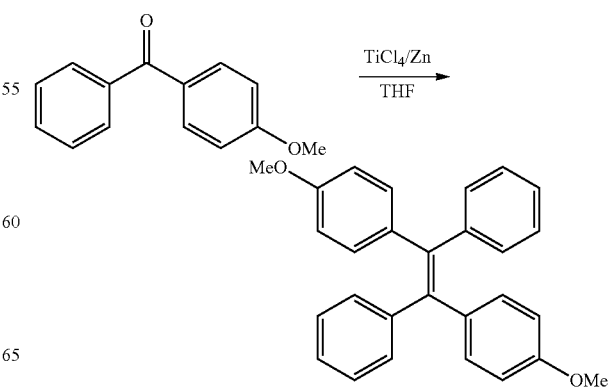

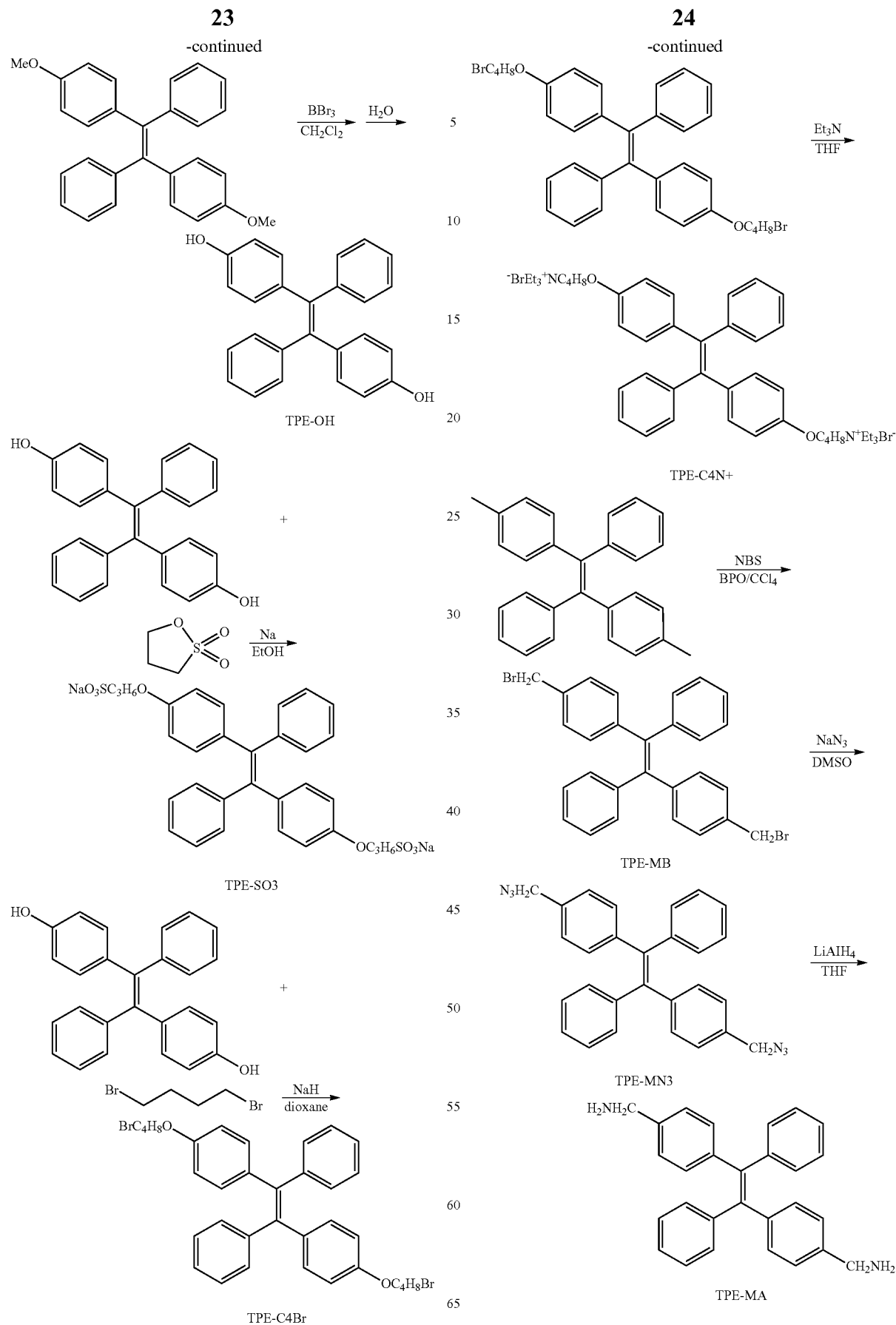

Scheme 2. Synthetic routes to the bromo- and carboxyl-substituted tetraphenylethylenes.
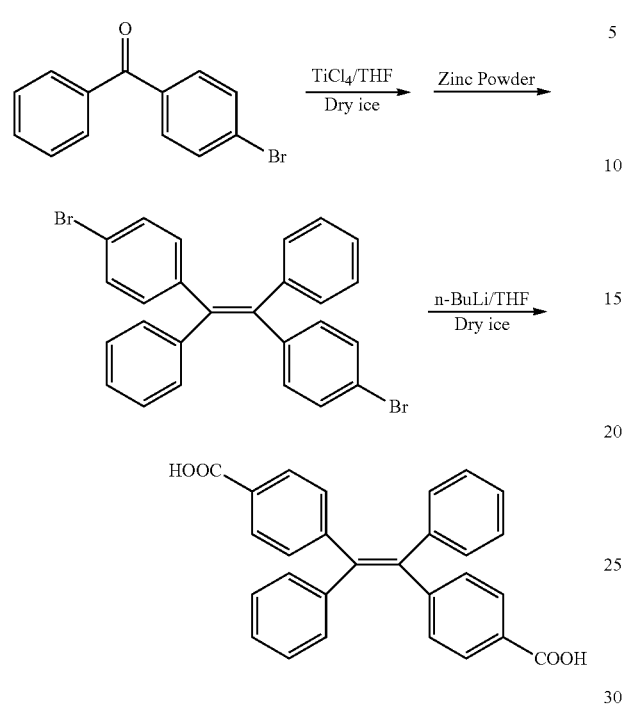
Scheme 3. Synthesis of silole derivatives.
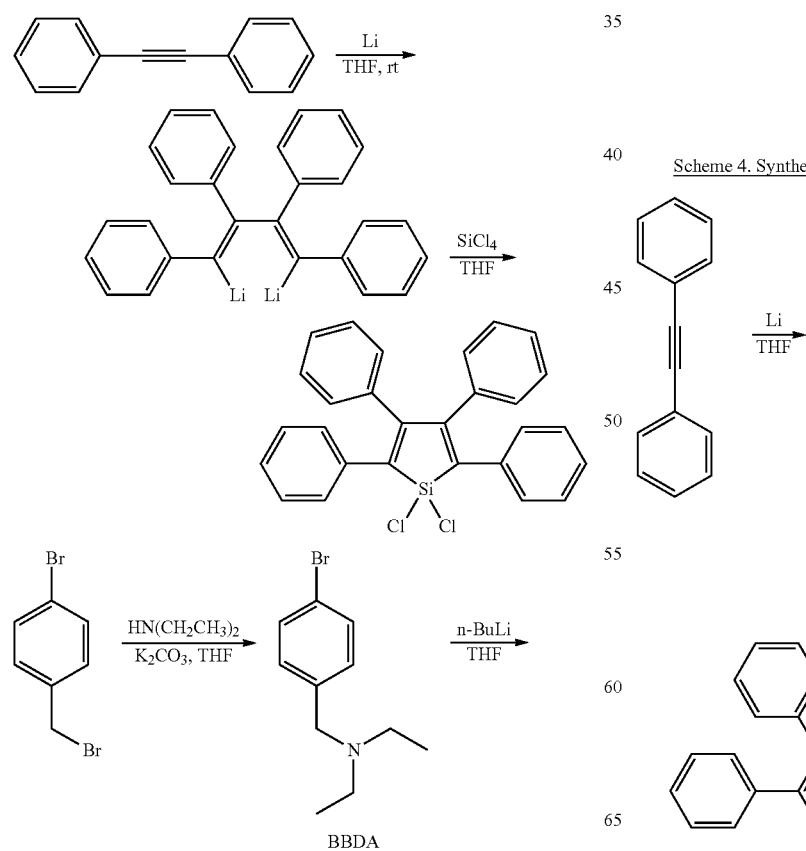
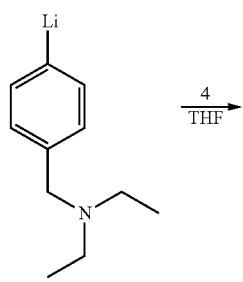
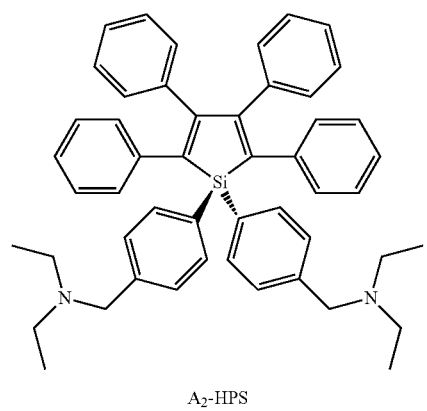
A₂-HPS
Scheme 4. Synthesis of Butadiene and Cyclobutadiene Derivatives
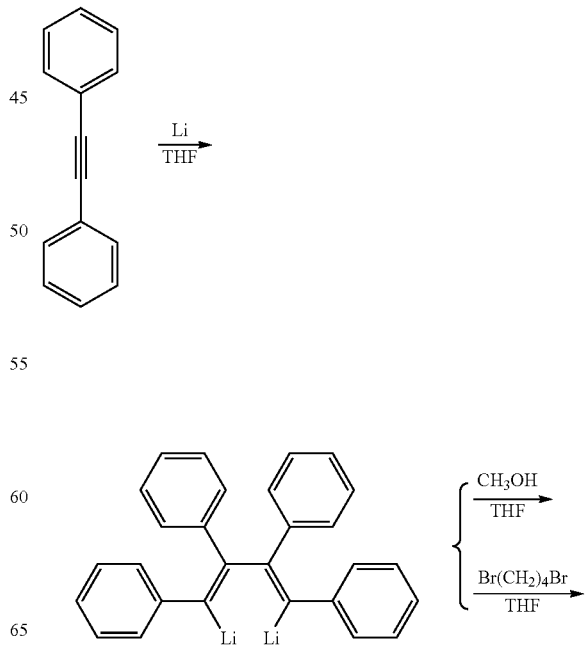

-continued

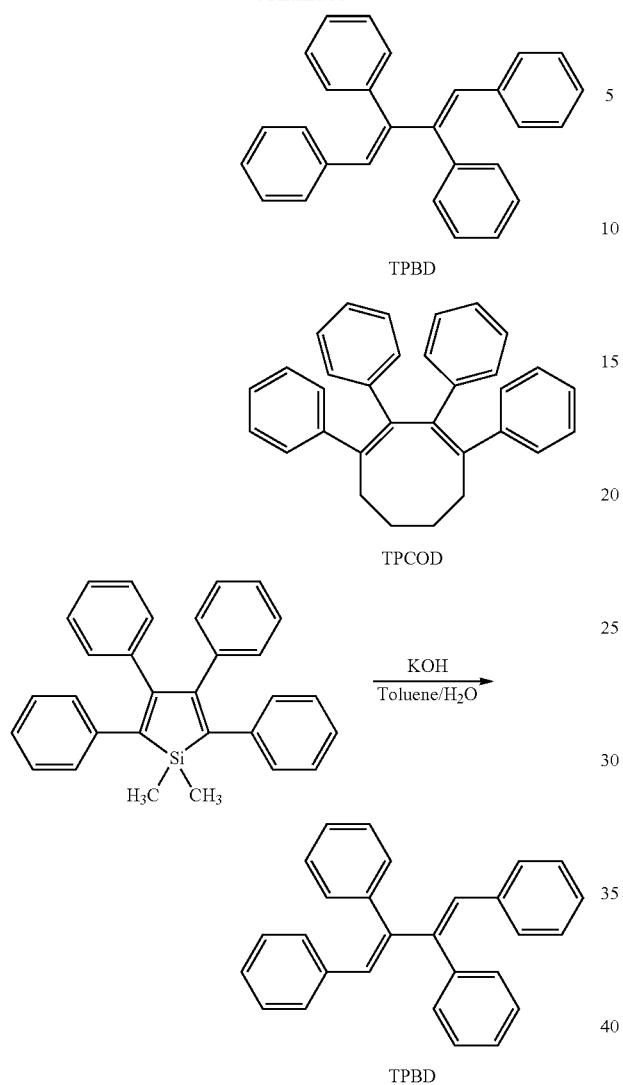

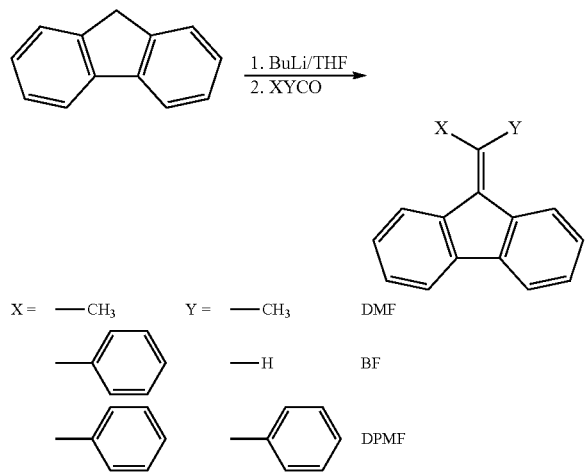

Scheme 6. Synthesis of Diphenylethylene Derivatives

Appropriately substituted versions of the precursors illustrated in the above schemes can be readily selected and employed, by the person of ordinary skill in the art to which the presently described subject matter pertains, to synthesize corresponding substituted products without undue experimentation.

Fluorescent Polymer Particles

The presently described subject matter is directed to water-dispersible, fluorescent, polymeric particles, which comprise or consist of the presently described TPE-derived water-soluble conjugated polyenes ("TPE dyes") that exhibit AIE, and a variety of polymer matrices having desirable hydrophilicity and chemical composition that can be designed to proved desirable characteristics.

Based on the proposed AIE mechanism, several of the presently described AIE-active dyes which exhibit fluorescent "turn-on" property when bound to biomacromolecules were investigated. A group of water-soluble AIE molecules were designed and synthesized. When the presently described water-soluble AIE molecules are dissolved in water or phosphate buffer saline (PBS), the solution is virtually nonemissive. However, the fluorescence increases significantly in the presence of proteins and DNA. There is a linear relationship between fluorescent intensity and the concentration of analytes in a certain range, which is of great importance in protein and DNA assays.

Furthermore, the presently described AIE water-soluble molecules are organic compounds, which make them easily accessible and much more economical compared to platinum or transition metal-containing counterparts. All of the presently described AIE-active water-soluble molecules are advantageous in that they can be synthesized in many structural forms and can be easily substituted with a variety of functional groups.

In addition, the presently described AIE-active water-soluble molecules are very stable. Virtually no change is observed in their photoluminescence spectra when they are stored under ambient temperature without any protection from light and air for more than two months. This is distinctly different from other dye molecules, which suffer from photobleaching when exposed to room illumination.

The presently described TPE dyes have conjugated molecular structures which can be expressed by the following formula:

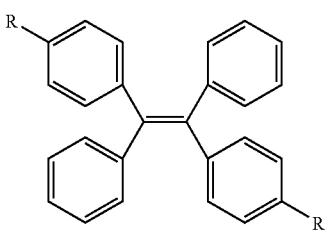

wherein R is selected from H, X, B(OH)$_2$, (X)$_n$COOR", (X)$_n$COOH, (X)$_n$NH$_2$, (X)$_n$NHR", (X)$_n$NR"$_2$, (X)$_n$N+R"$_3$Br$^-$, (X)$_n$OH, (X)$_n$SH, and (X)$_n$SO$_3^-$Na$^+$;

X is selected from (CH$_2$)$_n$, O(CH$_2$)$_n$, NH(CH$_2$)$_n$, N[(CH$_2$)$_n$]$_2$, and (OCH$_2$CH$_2$)$_n$; and R" is selected from R, R', (CH$_2$)$_n$CH$_3$, CONH—X—, COO—X—, C$_6$H$_5$—R, —CH$_2$—C$_6$H$_5$, and C$_6$H$_5$; and wherein n=0 to 20.

In an embodiment, R is selected from H, OH, COOH, and NH$_2$.

In a further embodiment, the present subject matter relates to water-dispersible, fluorescent, polymeric particles, wherein R is H and R' is selected from H, OH, COOH, and NH$_2$ In yet a further embodiment, the present subject matter relates to water-dispersible, fluorescent, polymeric particles, wherein the water-soluble conjugated polyene compound is selected from the group consisting of
4,4'-(1,2-diphenylvinyl)di(phenylcarboxylic acid);
1,2-Bis(4-methoxyphenyl)-1,2-diphenylethylene; and
1,2-Bis(4-hydroxyphenyl)-1,2-diphenylethylene.

In another embodiment, the present subject matter relates to water-dispersible, fluorescent, polymeric particles, wherein the polymer is a homopolymer or a copolymer comprising one or more monomers selected from the group consisting of a vinylaromatic monomer, an ethylenic monomer, an alkanoic acid or ester or anhydride, and an ethylchic acid or ester, wherein one or more of the one or more monomers is optionally functionalized.

In a further embodiment, the present subject matter relates to water-dispersible, fluorescent, polymeric particles, comprising at least one functionalized monomer.

In another embodiment, the present subject matter relates to water-dispersible, fluorescent, polymeric particles, wherein the ethylenic monomer is selected from an ethylenic monomer of isoprene, 1,3-butadiene, vinylidene chloride, or acrylonitrile; the vinylaromatic monomer is selected from styrene, bromo-styrene, α-methylstyrene, ethylstyrene, vinyl-toluene, chlorostyrene, chloromethylstyrene, or vinyl-naphthalene; the alkanoic acid or ester or anhydride is selected from acrylic acid, methacrylic acid, an alkyl acrylate or an alkyl methacrylate in which the alkyl group possess from 3 to 10 carbon atoms; an hydroxyalkyl acrylate, acrylamide, ethylenic acid ester containing 4 or 5 carbon atoms; or a difunctional monomer selected from divinylbenzene or 2,2-dimethyl-1,3-propylene diacrylate.

In yet a further embodiment, the present subject matter relates to water-dispersible, fluorescent, polymeric particles, wherein the one or more monomers are selected from the group consisting of styrene, methyl methacrylate, ethyl acrylate, butyl acrylate, 2-hydroxyethyl methacrylate, acrylic acid, and acrylamide.

In an embodiment, the present subject matter relates to water-dispersible, fluorescent, polymeric particles, wherein the at least one functionalized monomer is selected from the group consisting of 2-hydroxyethyl methacrylate, 2-amino-ethyl methacrylate, trimethylammoniumethyl methacrylate methosulfate, dimethylaminoethyl methacrylate, methacrylic acid, undecylenic acid, methyl propene sulfonic acid, undecylenyl alcohol, oleyl amine, glycidyl methacrylate, acrolein, and glutaraldehyde.

In a further embodiment, the present subject matter relates to water-dispersible, fluorescent, polymeric particles, wherein the one or more ethylenically unsaturated monomers comprise or consist of methyl methacrylate, butyl acrylate and 2-hydroxyethyl methacrylate.

In another embodiment, the present subject matter relates to water-dispersible, fluorescent, polymeric particles, wherein the methyl methacrylate, butyl acrylate, and 2-hydroxyethyl methacrylate are present in a ratio of from 4:5:1 to 5:4:1.

In yet another embodiment, the present subject matter relates to water-dispersible, fluorescent, polymeric particles, wherein the one or more ethylenically unsaturated monomers comprise or consist of methyl methacrylate, butyl acrylate, and acrylic acid and/or acrylamide.

In a further embodiment, the present subject matter relates to water-dispersible, fluorescent, polymeric particles, wherein the ratio of monomer to functionalized monomer is in the range of from about 3:1 to about 20:1.

In another embodiment, the present subject matter relates to water-dispersible, fluorescent, polymeric particles, wherein the ratio of monomer to functionalized monomer is in the range of from about 7:1 to about 11:1.

In yet another embodiment, the present subject matter relates to water-dispersible, fluorescent, polymeric particles, wherein the ratio of monomer to functionalized monomer is about 9:1.

In an embodiment, the present subject matter relates to water-dispersible, fluorescent, polymeric particles, having a glass transition temperature below room temperature.

In a further embodiment, the present subject matter relates to water-dispersible, fluorescent, polymeric particles, comprising microparticles.

In yet a further embodiment, the present subject matter relates to water-dispersible, fluorescent, polymeric particles, wherein the microparticles comprise a mean particle diameter in the range of from about 0.01 µm to about 5 µm.

In another embodiment, the present subject matter relates to water-dispersible, fluorescent, polymeric particles, wherein the microparticles comprise a mean particle diameter in the range of from about 10 nm to about 500 nm.

In an embodiment, the present subject matter relates to water-dispersible, fluorescent, polymeric particles, wherein greater than about 50% of the microparticles comprise a mean particle diameter in the range of from about 10 nm to about 500 nm.

In a further embodiment, the present subject matter relates to water-dispersible, fluorescent, polymeric particles, wherein greater than about 70% of the microparticles comprise a mean particle diameter in the range of from about 40 nm to about 400 nm.

In yet a further embodiment, the present subject matter relates to a method for making water-dispersible, fluorescent, polymeric particles, comprising or consisting of: dissolving the water-soluble conjugated polyene compound in the one or more monomers to form a monomer solution; providing an aqueous composition comprising one or more members selected from the group consisting of a surfactant, a stabilizer and a cross-linking agent; adding the monomer solution drop-wise to the aqueous composition to form a mixture; and polymerizing the mixture to produce the water-dispersible, fluorescent, polymeric particles.

In another embodiment, the present subject matter relates to the method for making water-dispersible, fluorescent, polymeric particles, wherein polymerizing comprises emulsion polymerization, microemulsion polymerization, suspension polymerization, or dispersion polymerization.

In another embodiment, the present subject matter relates to the method for making water-dispersible, fluorescent, polymeric particles, wherein the water-dispersible, fluorescent, polymeric particles are dispersed stably in the aqueous composition.

In a further embodiment, the present subject matter relates to the water-dispersible, fluorescent, polymeric particles, comprising a formulation selected from a bioprobe, a coating, a paint, a flexible free-standing film, a cosmetic, a fluidic tracer, or a marker. A fluidic tracer can be used to investigate capillary flow, to define neuronal cell connectivity and to study dye translocation through gap junctions, as well as to follow cell division, cell lysis or liposome fusion. A marker can be used as an indicator of a biologic state, for example, pH, polarity, and viscosity of the biological environment.

In another embodiment, the present subject matter relates to a flexible free-standing film comprising water-dispersible, fluorescent, polymeric particles.

The described TPE dyes possess unique characteristics, in that when molecularly dissolved in aqueous solutions, for example, water, emission is weak, whereas when aggregated in poor non-aqueous solvents or fabricated into thin films, emission is substantially increased.

The TPE dyes can be prepared according to the synthetic routes shown in Scheme 2 described herein. Bromo-substituted TPE (TPE-Br) can first be prepared by the McMurry coupling reaction of 4-bromobenzophenone using titanium (IV) chloride/zinc as catalyst. Then the bromo groups in TPE-Br can be transformed into other groups, e.g., carboxyl functionalities, by reaction with n-butyl lithium followed by dry ice.

The polymers for encapsulation of the presently described TPE dyes are obtained by polymerization of ethylenically unsaturated monomers. Such a polymer can be a homopolymer or copolymer containing units derived from vinylaromatic or ethylenic monomers, or from alkanoic or ethylchic acids or esters, which are optionally functionalized. This type of polymer is readily accessible to any person skilled in the art and it will be sufficient to mention only a few such polymers below, in a non-limiting manner. Such polymers can comprise or consist of one or more of the following: ethylenic monomers of isoprene, 1,3-butadiene, vinylidene chloride or acrylonitrile type; vinylaromatic monomers such as styrene, bromo-styrene, alpha-methylstyrene, ethylstyrene, vinyltoluene, chlorostyrene or chloromethylstyrene, or vinylnaphthalene; alkanoic acids, esters or anhydrides such as acrylic acid, methacrylic acid, alkyl acrylates and alkyl methacrylates in which the alkyl group possesses 3 to 10 carbon atoms; hydroxyalkyl acrylates, acrylamides, ethylenic acid esters containing 4 or 5 carbon atoms; and difunctional monomers such as divinylbenzene or 2,2-dimethyl-1,3-propylene diacrylate and/or other copolymerizable monomers. Suitable monomers can comprise or consist of styrene, methyl methacrylate, ethyl acrylate, butyl acrylate, 2-hydroxyethyl methacrylate, acrylic acid, and acrylamide. These monomers are used alone or mixed with each other in any proportion, or alternatively mixed with another copolymerizable monomer selected from those described above. The functional groups can be incorporated onto the surface of the fluorescent particles by, for example, using a mixture of monomer and functionalized monomer during the polymerization. The functionalized monomer used can comprise or consist of one or more of the following: 2-hydroxyethyl methacrylate, 2-aminoethyl methacrylate, trimethylammoniumethyl methacrylate methosulfate, dimethylaminoethyl methacrylate, methacrylic acid, undecylenic acid, methyl propene sulfonic acid, undecylenyl alcohol, oleyl amine, glycidyl methacrylate, acrolein, glutaraldehyde and the like.

The polymer particles may be formed by the use of appropriate polymerization techniques such as conventional emulsion polymerization, microemulsion polymerization, suspension polymerization or other means of polymerization with or without a crosslinking agent such as divinyl benzene or the like. These techniques and agents are well known to those of ordinary skill in the art to which the present subject matter pertains. The skilled artisan can readily select and employ such techniques and agents without undue experimentation.

The described TPE dyes are dissolved in the monomer(s) prior to polymerization, then incorporated into the polymer matrices through the particle formation process. TPE dyes are organic in nature, which makes them readily soluble in the monomers used. TPE dyes can also withstand common polymerization conditions. Further, TPE dyes, for example, having various peripheral substituent groups on the aromatic rings, have an affinity towards the interior of the particles. That is, they are chemically compatible with the polymers constituting the latex particles. This compatibility is important during the formation of the corresponding fluorescent polymer particles.

The fluorescent polymer particles prepared according to the present subject matter are stable aqueous dispersions whose size is as described herein and is generally between 0.01 micron and 5 microns, for example, less than 1 micron in diameter, regardless of the polymer composition. The aqueous dispersions have a content of polymer particles from 0.1% to 50% by weight relative to the total weight of the dispersion, for example, from 10% to 30% by weight.

The spectral characteristics of these fluorescent particles can be varied by incorporating different TPE dyes. The fluorescent intensity of these polymer particles can be adjusted by varying the load concentration of the TPE dyes. The maximum TPE dye content in the polymer particles depends on the nature of the fluorochromes, the encapsulation technique used, the nature of the polymer constituting the particles and the size of these particles. Load concentration can depend on the functionalization density (the number of functional groups per particle) and the interaction (covalent or non-covalent) between the dye and the particles. The functionalization density depends on the size of the particles and the nature of the polymer (the polymer chain bearing functional groups), while the interaction depends on the nature of the fluorophores, the nature of the polymer, and the encapsulation technique used. The nature of the fluorophores depends on the kinds of functional groups they are facilitated. The maximum TPE dye content in the polymer particles may thus vary considerably and reach values of several million fluorochrome molecules per latex particle. The dye content of the presently described fluorescent polymer particles can be much higher in comparison to the conventional particles, owing to the absence of self-quenching of the TPE dyes. On the contrary, the fluorescence of the present TPE dyes can be remarkably enhanced at high concentrations, resulting from the AIE effect of TPE dyes.

By using the processes of the present subject matter, fluorescent polymer particles can be optimized in terms of size, polymer composition, surface chemistry, and/or spectral characteristics. The fluorescent polymer particles according to the present subject matter may be used in all the conventional applications of polymer particles which are well known to those skilled in the art (paint, coating, cosmetic, marker, fluidic tracer, etc.). The fluorescent polymer particles according to the present subject matter are more particularly intended for direct or indirect involvement in biological analyses.

Use of the Conjugated Polyenes

While biosensing processes such as molecular beacons require non-trivial effort to covalently label or mark biomolecules, we here present a label-free DNA assay system using a simple dye with aggregation-induced emission (AIE) characteristics as the fluorescent bioprobe. G-quadruplex, a secondary structure of DNA, has been identified to be associated with human telomeres or telomerase, which may affect gene expression and control cancel cell proliferation. 1,1,2,2-tetrakis[4-(2-triethylammonioethoxy)-phenyl]ethene tetrabromide (TTAPE) is nonemissive in solution but becomes highly emissive when aggregated [Aggregation-induced emission (AIE)]. When TTAPE is bound to DNA via electrostatic attraction, its emission is turned on. This process can be reversible. When a competitive cation is added to the DNA solution, TTAPE is released and its emission is turned off. TTAPE works as a sensitive poststaining agent for electrophoresis gel visualization of DNA. The dye is highly affinitive to a secondary structure of G-quadruplex. The bathochromic shift involved in the folding process allows spectral discrimination of the G-quadruplex from other DNA structures. The strong affinity of TTAPE dye to G-quadruplex structure is associated with a geometric fit aided by the electrostatic attraction. The distinct AIE feature of TTAPE enables real-time monitoring of folding process of G1 in the absence of any pre-attached fluorogenic labels on the DNA strand. TTAPE can be used as a $K^+$ biosensor because its specificity to $K^+$-induced and stabilized quadruplex structure. On the other hand, TPE-SO3, the counterpart of TTAPE, can serve as a probe for protein detection in aqueous media. TPE-SO3 shows higher affinity to human serum albumin (HSA), the main protein in human urine. A higher level of protein loss in the urine, called proteinuria, may mean there is a kidney disease. Thus, TPE-SO3 can be potential used for urinary protein detection.

Figure 23:
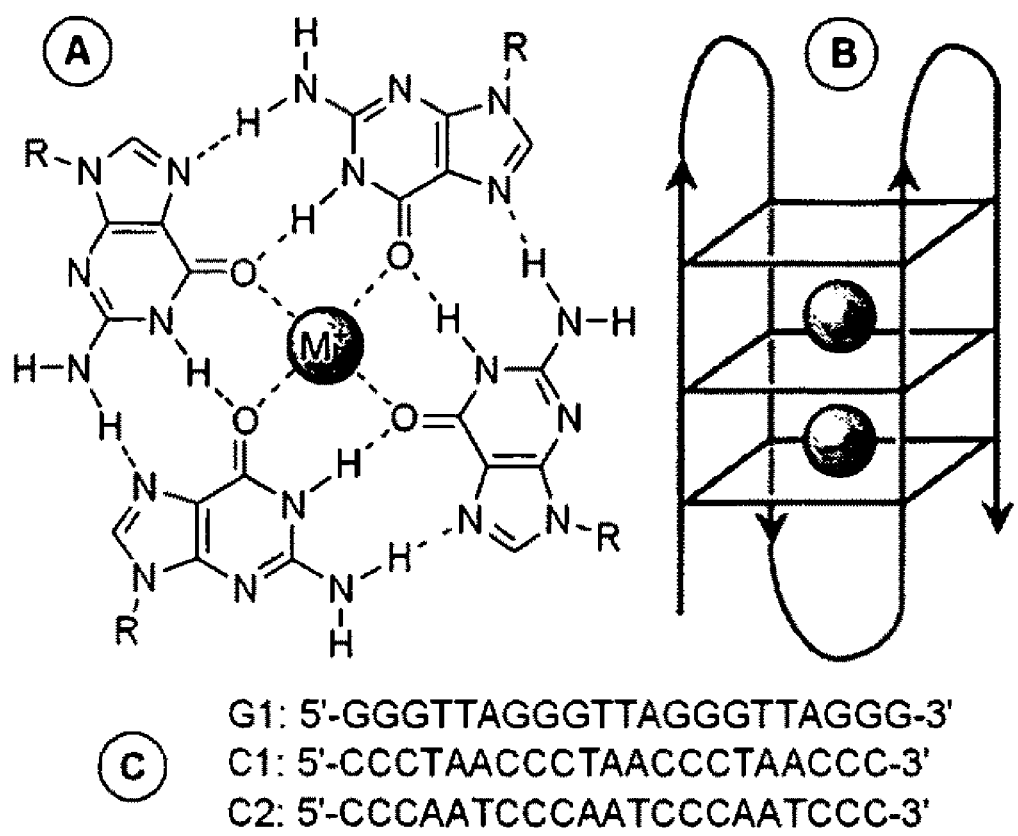
FIG. 23A shows the structure of a G-quartet showing hydrogen bonds between G units and interaction with a cation ($M^+$).
FIG. 23B shows a G-quadruplex folded by a human telomeric DNA strand.
FIG. 23C shows the sequences of G1 (SEQ ID 1) and its complementary (C1) (SEQ ID 2) and non-complementary (C2) (SEQ ID 3) strands.
Figure 24:
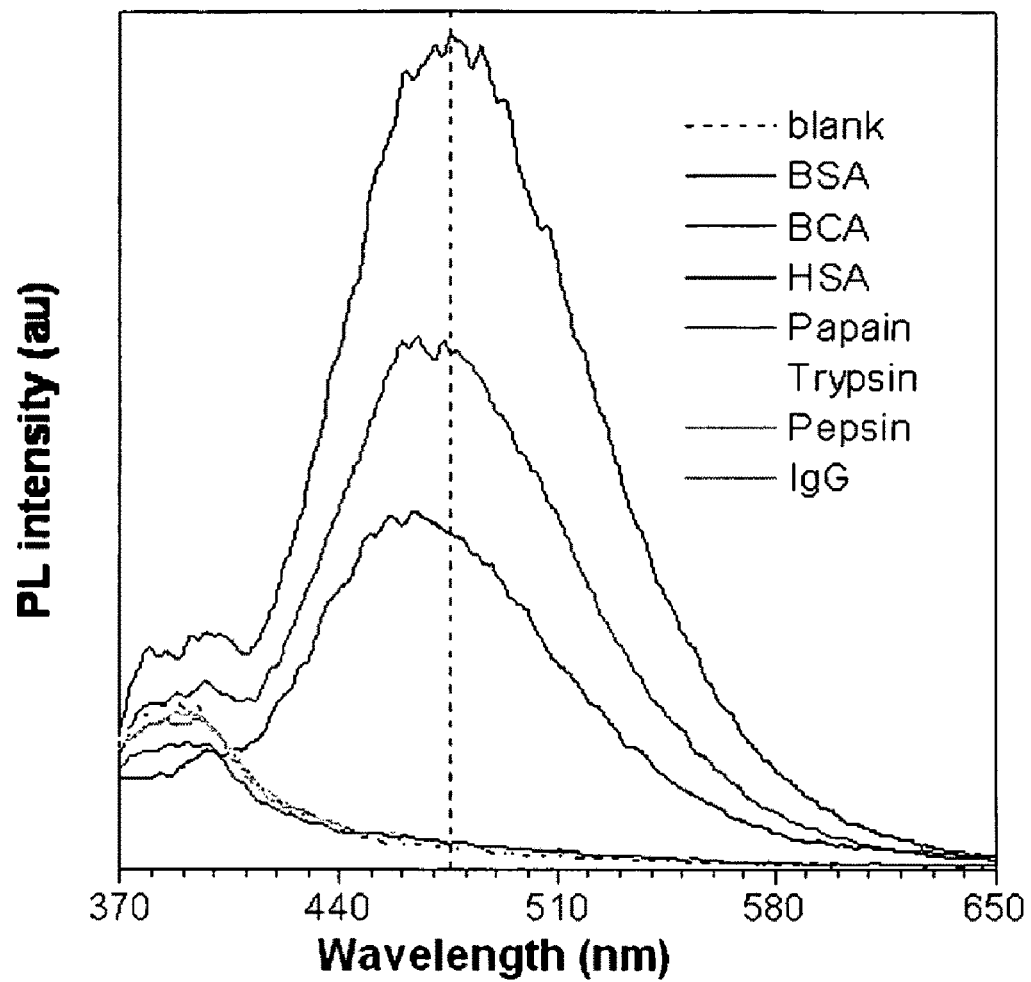
FIG. 24 shows the FL spectrum of TPE-SO3 with addition of different proteins in phosphate buffer saline (pH=7.0). [TPE-SO3]=5 μM. Excitation wavelength: 350 nm.

A single-stranded (ss) DNA with guanine (G)-rich repeat sequences can assume a square planar arrangement of the G units stabilized by Hoogsteen hydrogen bonds (FIG. 23A). An array of these G-quartets can stack on top of each other to form a secondary structure named G-quadruplex (FIG. 23B). This structure is further stabilized by the monovalent cations (e.g., $K^+$) located in the centers of G-tetrads. It is predicted that thousands of DNA sequences sprinkled over the human genome are potential quadruplex-forming sites, making the tetrad structure one of the most prevalent regulatory motifs in the body. Much effort has been devoted to the studies on the biology of genomic and telomeric G-quadruplexes. It has been found, for example, that quadruplex formation can affect gene expression and inhibit telomerase activity in cancer cells. It has been envisioned that quadruplex-targeting drugs may enable artificial regulation of gene expression and control of cancel cell proliferation. Clearly, efficient probing of G-quadruplex structures is a prerequisite to the rational design of quartet-specific medication and telomere-aimed anticancer therapy.

A variety of techniques, including nuclear magnetic resonance (NMR), mass spectroscopy, circular dichroism (CD), UV melting profile analysis, poly(acrylamide) gel electrophoresis (PAGE), and surface plasmon resonance, have been used to study G-quadruplex formation. These methods, however, require large quantities of DNA samples because of their poor sensitivities. Fluorescence (FL)-based probe system, on the other hand, offers superb sensitivity, low background noise, and wide dynamic working range. A few FL sensors based on "molecular beacons" and fluorescent resonance energy transfer processes have been developed, which prove to be powerful in studying conformational transitions of quadruplexes. These processes, however, require pre-labeling of oligonucleotides by fluorophores or dual tagging on a single DNA strand by chemical reactions. Precise synthesis of a DNA-dye conjugate is a nontrivial job, and product isolation and purification is often painstaking. In addition, structural changes caused by the chemical modifications may affect conformations of the G-quadruplexes and interfere with their folding kinetics.

Biological processes are undertaking in physiological fluids and accordingly biological assays are commonly conducted in aqueous buffer solutions. The working units in the FL probes, however, are hydrophobic aromatic rings and other π-conjugated chromophores. The FL dyes tend to aggregate when absorbed onto strand surfaces or after entering hydrophobic pockets of folded strands, due to the incompatibility of the dyes with the hydrophilic media and the π-π stacking interaction between their π-conjugated chromophores. The aggregate formation normally quenches light emissions of the dyes, which poses a thorny obstacle to the development of efficient FL probes. Various approaches have been taken in an effort to impede aggregate formation, such as using long spacers to separate chromophoric units. Obviously, it is nicer and more desirable to have sensitive and selective G-quadruplex probes that do not require pre-modifications of the DNA strands and that do not suffer from aggregation-caused emission quenching.

It has recently been observed a novel phenomenon of AIE: a series of nonemissive dyes, such as siloles, butadienes, pyrans, fulvenes, biaryls and TPEs, are induced to luminesce by aggregate formation. The AIE dyes are not only excellent emitters for the fabrication of efficient light-emitting diodes but also sensitive probes for the detection of biomolecules. Among them, the TPE-based dyes have received much attention because of their facile synthesis, ready functionalization, good photostability, and high FL quantum yields ($\Phi_F$). In this work, we synthesized a new AIE-active TPE salt, i.e. 1,1,2,2-tetrakis[4-(2-triethylammonioethoxy)phenyl]ethene tetrabromide (TTAPE), and explored its potential application as a G-quadruplex probe, using an oligonucleotide of 5'-GGGT-TAGGG-TTAGGGTTAGGG-3' or [$dG_3(T_2AG_3)_3$] (G1) (SEQ ID 1) as a model DNA that mimics the $T_2AG_3$ repeat sequences in the single-stranded region of a human telomere (FIG. 23C). In an aqueous buffer, the nonemissive TTAPE dye becomes highly luminescent upon its binding to G1 via electrostatic attraction, thanks to its multiple positive charges. When G1 folds into G-quadruplex structure, emission peak ($\lambda_{em}$) of the AIE dye undergoes a noticeable bathochromic shift, allowing easy differentiation of the G-quadruplex from other DNA structures. The folding processes of G1 can be followed by the time-dependent FL measurement of the AIE dye.

In another embodiment, the present subject matter relates to a method of detecting G-quadruplex formation, DNA, or protein and protein levels wherein the cation added to the biological sample and polyene mixture is selected from the group consisting of $K^+$, $Li^+$, $Na^+$, $NH_4^+$, $Mg^{2+}$, and $Ca^{2+}$.

In yet another embodiment, the present subject matter relates to a method of detecting G-quadruplex formation, DNA, or protein and protein levels wherein the cation added to the biological sample and polyene mixture is $K^+$.

In a further embodiment, the present subject matter relates to a method of detecting G-quadruplex formation, DNA, or protein and protein levels wherein the water-soluble conjugated polyene compound is a tetraphenylethylene ("TPE").

In yet another embodiment, the present subject matter relates to a method of detecting G-quadruplex formation, DNA, or protein and protein levels wherein the TPE is selected from the group consisting of 1,2-diphenyl-1,2-bis(4, 4'-(3-sulfonato)propoxyl)phenylethylene (TPE-SO3) and 1,1,2,2-tetrakis[4-(2-triethylammonioethoxy)-phenyl] ethene tetrabromide (TTAPE).

In another embodiment, the present subject matter relates to a method of detecting G-quadruplex formation, DNA, or protein and protein levels wherein the TPE is 1,1,2,2-tetrakis [4-(2-triethylammonioethoxy)-phenyl]ethene tetrabromide (TTAPE).

Functional kidneys are capable of removing wastes from the body, regulating electrolyte balance and blood pressure, and stimulating red blood cell production. Kidney diseases are a major cause of health problems world-wide. E.g. >20 million Americans—1 of 9 adults—have chronic kidney disease (CKD). Another 20 million more Americans are at increased risk (US National Kidney Foundation). Each year in the United States, more than 100,000 people are diagnosed with kidney failure (ESRD: End-Stage Renal Disease). The high-risk groups for kidney disease include diabetes and hypertension patient. Most kidney diseases do not cause noticeable symptoms until very late. Nearly 50% of people with an advanced form of kidney disease even don't know. However, certain changes in the urine can be seen earlier, which may suggest problems with kidneys or urinary tract. There are over a hundred different types of proteins in the blood and the kidneys are very good at keeping them from entering the urine. Most of the proteins that make it into the urine are reabsorbed, chewed up and returned to the blood. As a result, less than 150 mg (30 mg/L) of protein is normal lost in the urine per day. A higher level of protein loss in the urine is called proteinuria and may mean there is a kidney disease. Determination of urinary protein is of major clinical importance because it readily reflects kidney functionality.

In an embodiment, the present subject matter relates to a method of diagnosing a kidney disorder comprising contacting a biological sample with a water-soluble conjugated polyene compound and detecting luminescence.

In another embodiment, the present subject matter relates to a method of diagnosing a kidney disorder wherein the biological sample is selected from the group consisting of a tissue sample, cell sample, blood, saliva, spinal fluid, lymph fluid, vaginal fluid, seminal fluid, and urine.

In yet another embodiment, the present subject matter relates to a method of diagnosing a kidney disorder wherein the biological sample is urine.

In a further embodiment, the present subject matter relates to a method of diagnosing a kidney disorder wherein the water-soluble conjugated polyene compound is a tetraphenylethylene ("TPE").

In a still further embodiment, the present subject matter relates to a method of diagnosing a kidney disorder wherein the TPE is selected from the group consisting of 1,2-diphenyl-1,2-bis(4,4'-(3-sulfonato)propoxyl)phenylethylene (TPE-SO3) and 1,1,2,2-tetrakis[4-(2-triethylammonioethoxy)-phenyl]ethene tetrabromide (TTAPE).

In another embodiment, the present subject matter relates to a method of diagnosing a kidney disorder wherein the TPE is 1,2-diphenyl-1,2-bis(4,4'-(3-sulfonato)propoxyl)phenylethylene (TPE-SO3).

In the past, colorimetric assays have been used for the confirmation and semi-quantitative measurement of urinary proteins. However, these methods generally lack of sensitivity and accuracy. Sensors based on luminescent materials have attracted special attention because of their superb sensitivity, selectivity and rapidity, which makes them widely applicable for clinical assays. In the present subject matter, an AIE-active molecule, TPE-SO3, was developed for the detection of urinary proteins. TPE-SO3 exhibits high sensitivity and selectivity upon the presence of HSA especially in the media of artificial urine.

Dye Synthesis

Figure 49:
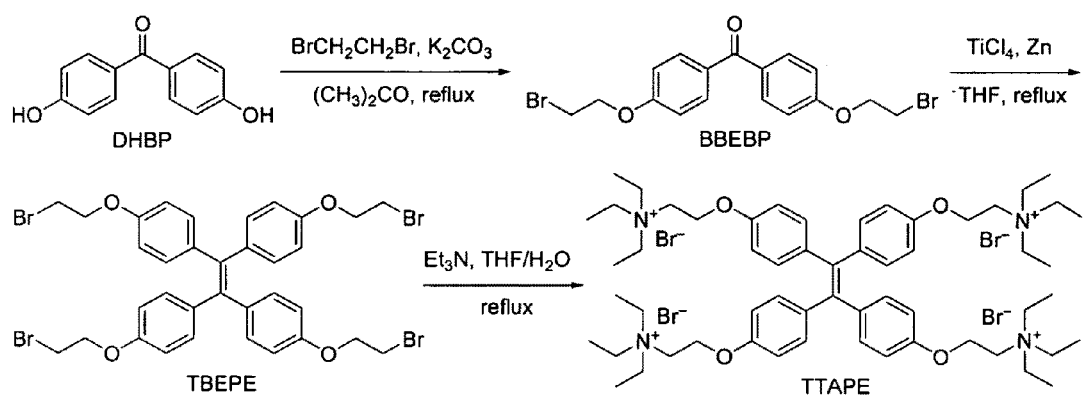
FIG. 49 is the Synthesis of 1,1,2,2-tetrakis[4-(2-triethylammonioethoxy)phenyl]ethene tetrabromide (TTAPE)
Figure 50:
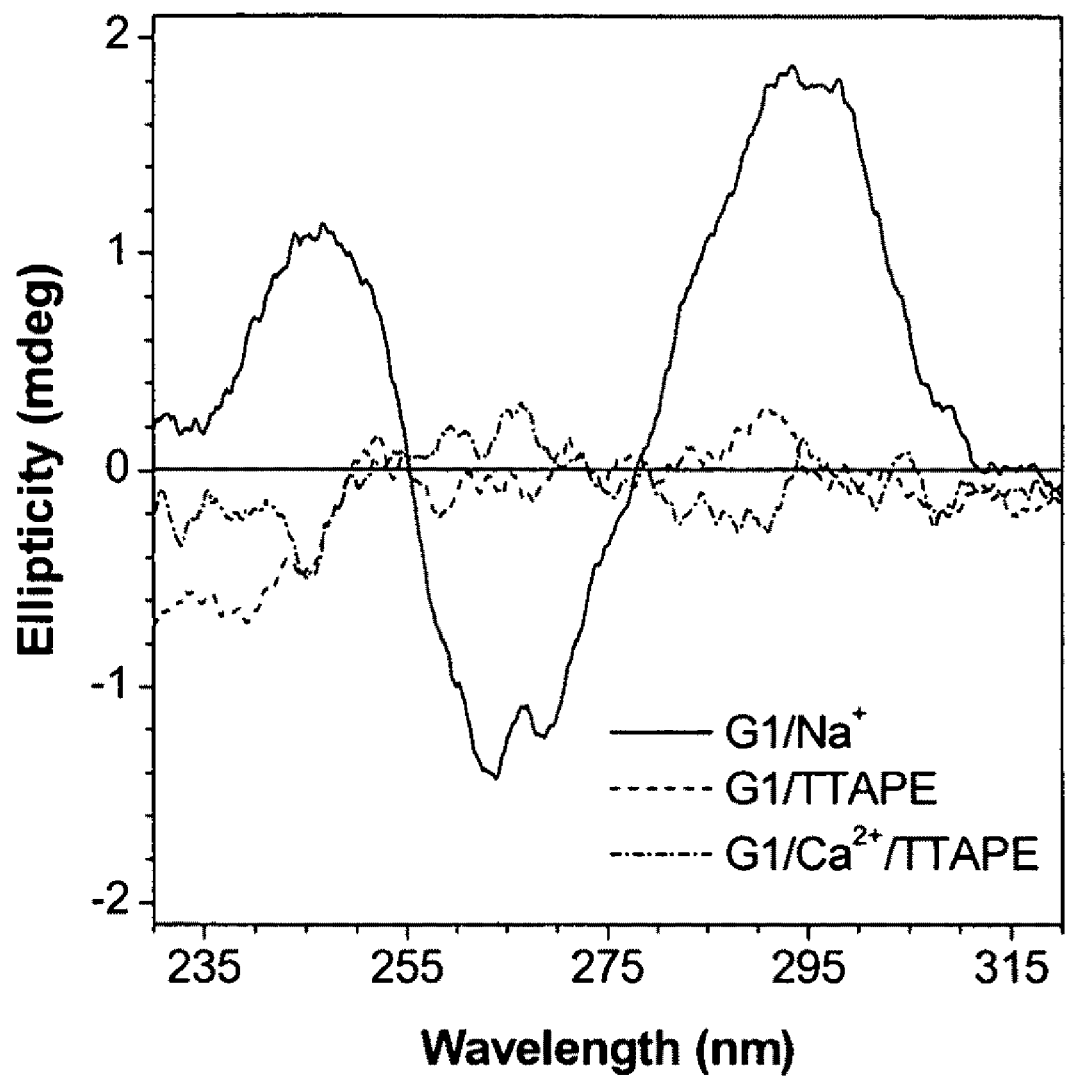
FIG. 50 shows the CD spectra of G1 in a Tris-HCl buffer in the presence or absence of a metal ion and/or TTAPE at 20° C. [G1]=9 μM, [ion]=0.5 M, [TTAPE]=4.5 μM.
Figure 51:
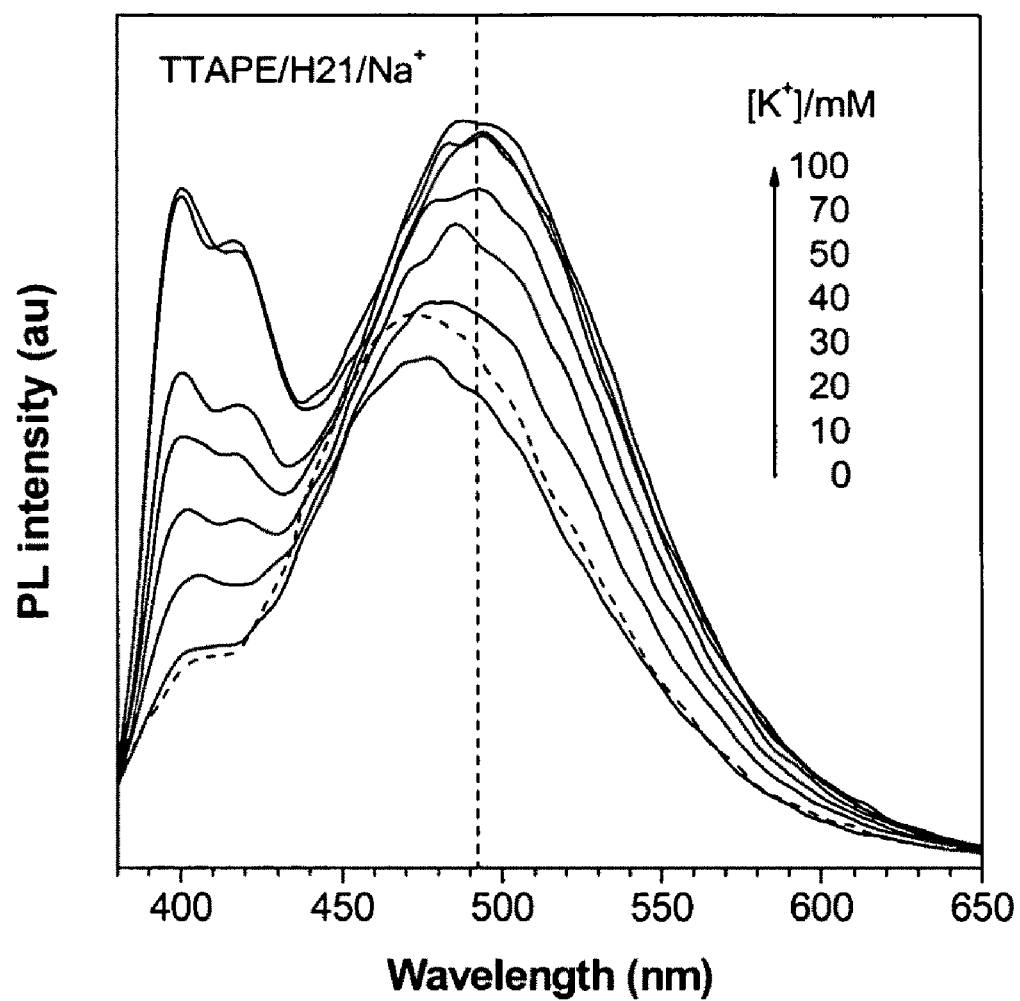
FIG. 51 shows the emission spectra of TTAPE/H21 in $Na^+$ solution (100 mM) upon $K^+$ titration in buffer solutions (pH=7.5). The final concentration of $Na^+$ is kept at 100 mM. [TTAPE]=4.5 μM, [H21]=4.5 μM. Excitation wavelength: 350 nm.
Figure 52:
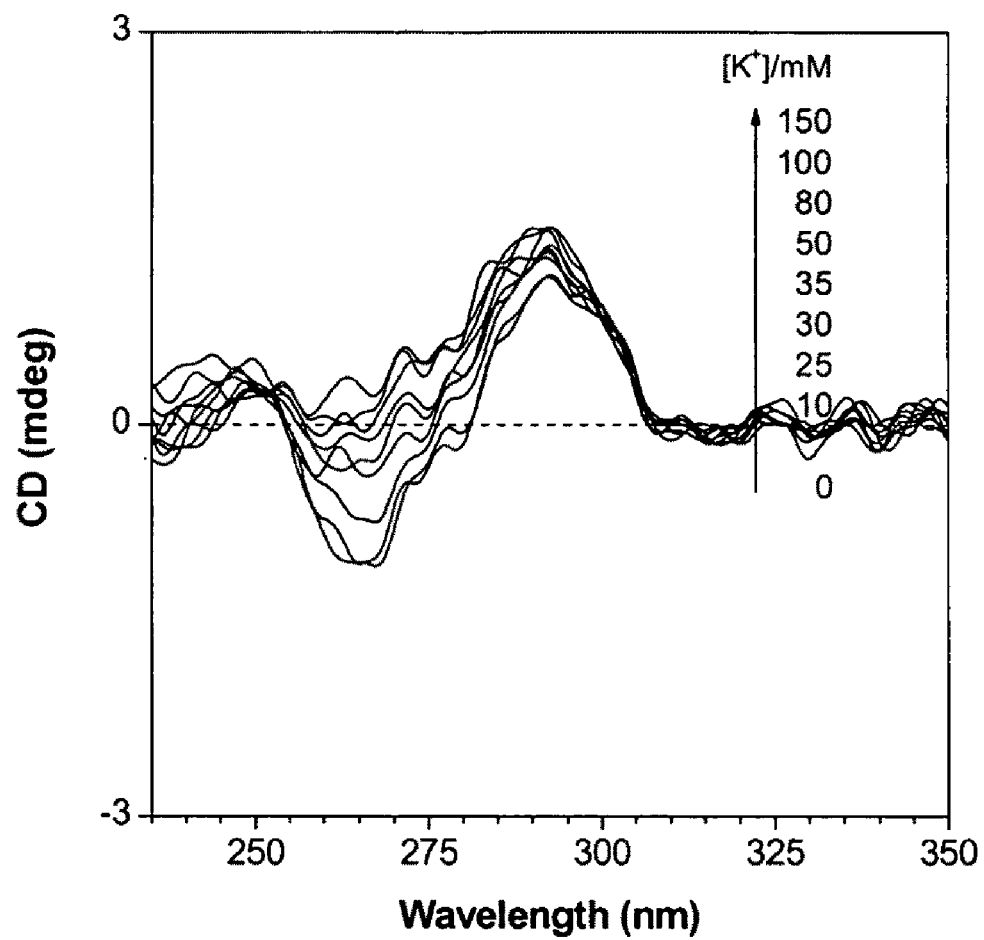
FIG. 52 shows the CD spectra of H21 (5 μM) in $Na^+$ solution (100 mM) upon $K^+$ titration in 5 mM Tris-HCl (pH=7.50).
Figure 53:
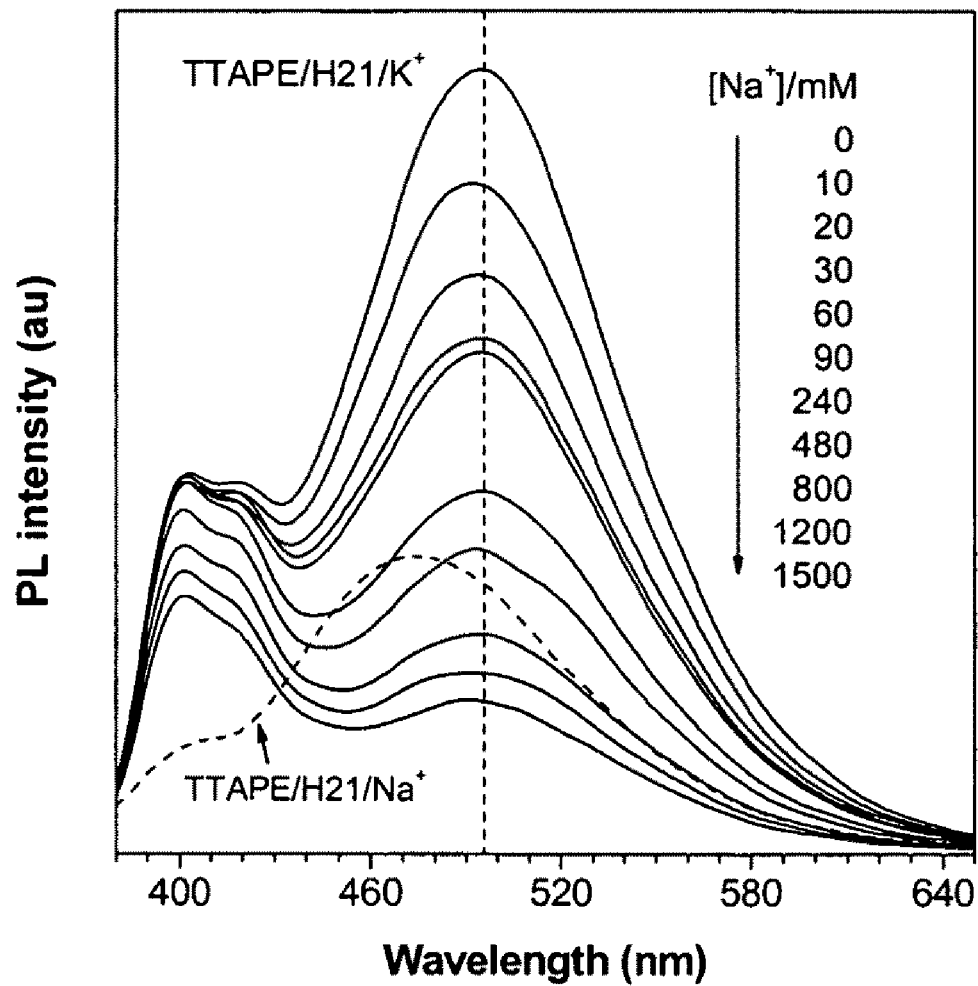
FIG. 53 shows the emission spectra of buffer solutions (pH=7.5) of TTAPE/G1 containing $K^+$ and $Na^+$ ions. The final concentration of $K^+$ is kept at 100 mM. [TTAPE]=4.5 μM, [DNA]=4.5 μM. Excitation wavelength: 350 nm.
Figure 54:
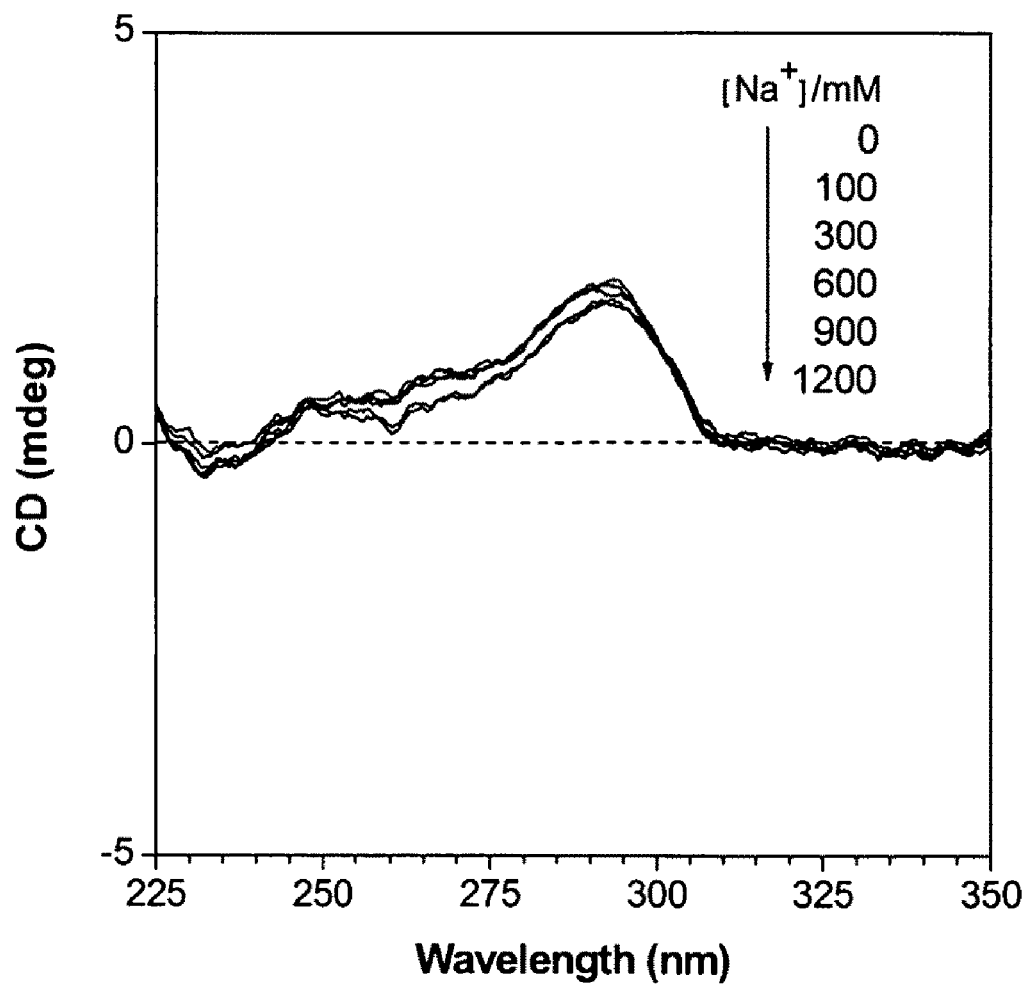
FIG. 54 shows the CD spectra of buffer solutions (pH=7.50) of TTAPE/G1 containing $K^+/Na^+$ ions. The final concentration of $K^+$ is kept at 100 mM. [TTAPE]=4.5 μM, [DNA]=9 μM. Excitation wavelength: 350 nm.
Figure 55:
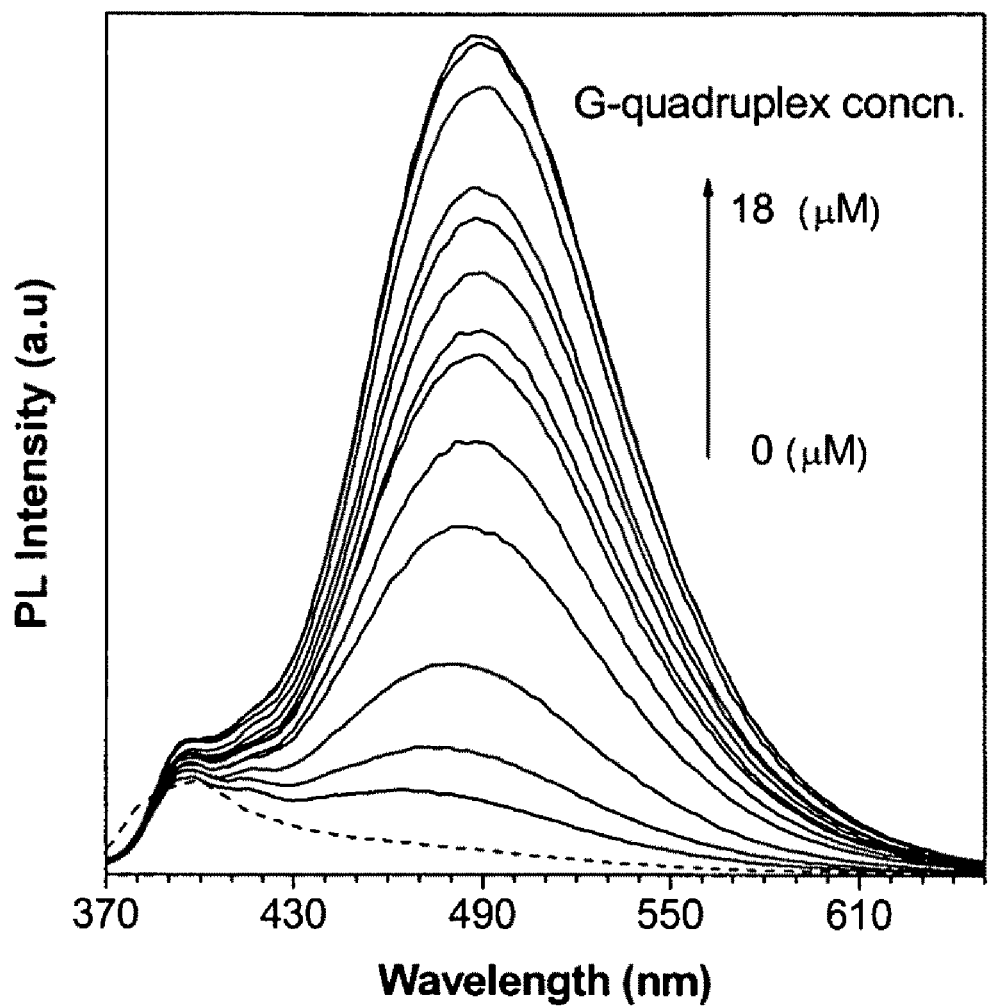
FIG. 55 shows the PL spectra of TTAPE (4.5 μM) in the presence of different concentrations of G-quadruplex DNA (G1 in 150 mM $K^+$) in 5 mM Tris-HCl buffer (pH=7.5). Excitation wavelength: 350 nm.
Figure 56:
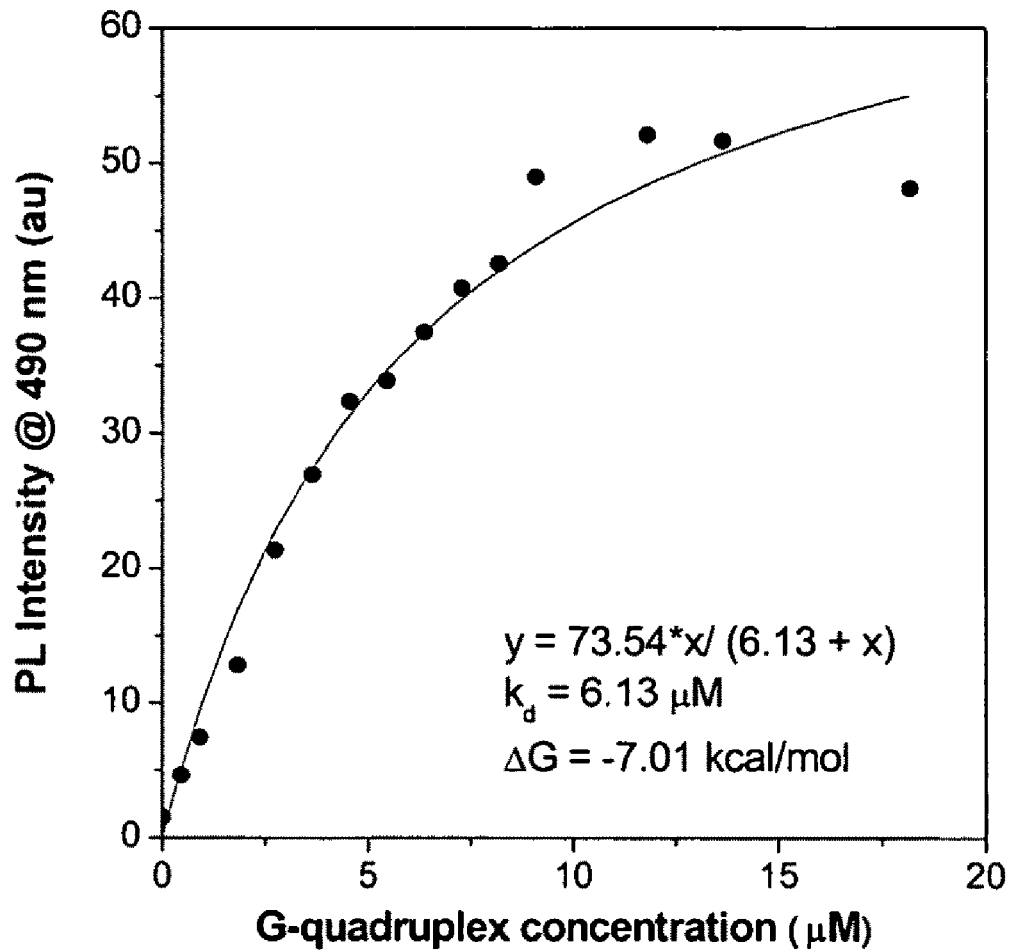
FIG. 56 shows the fluorometric titration of G-quadruplex DNA (plot of the fluorescence intensity at 470 nm) to the solution with TTAPE (4.5 μM) in 5 mM Tris-HCl buffer (pH=7.5) and its fitting curve to OneSiteBind mode. Excitation wavelength: 350 nm
Figure 57:
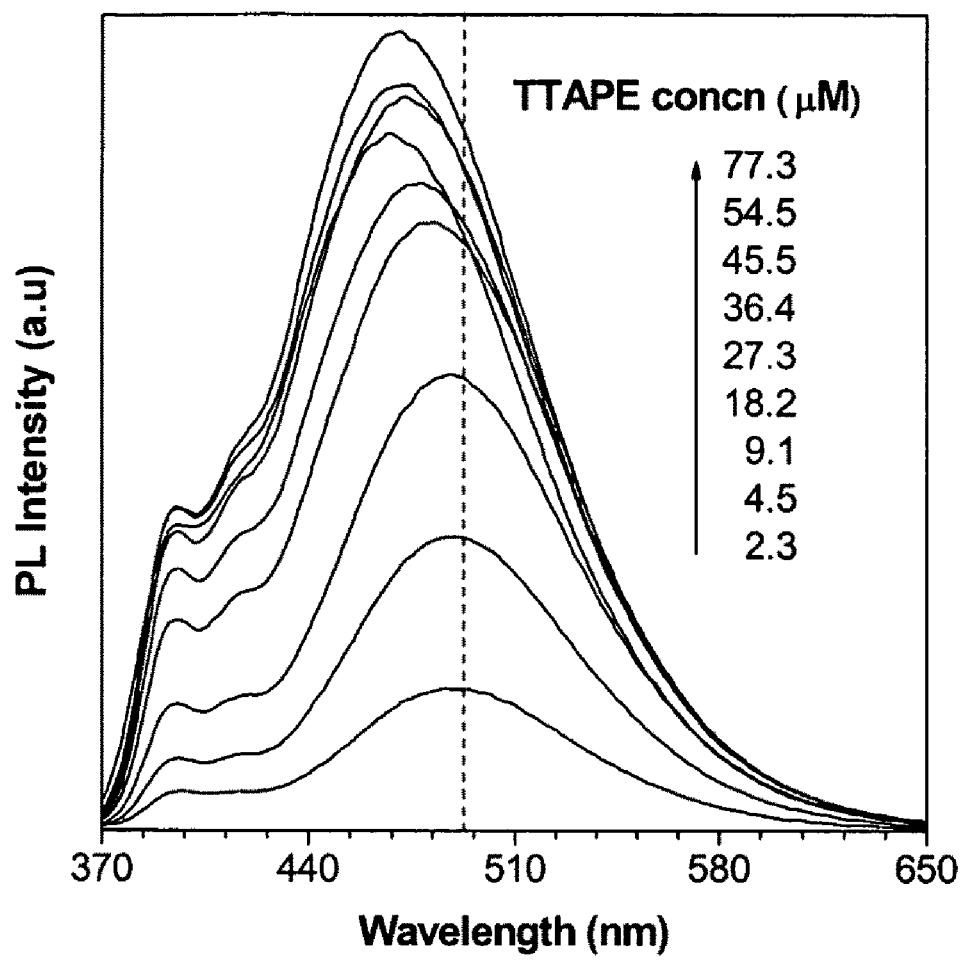
FIG. 57 shows the PL spectra of 9 μM of G-quadruplex DNA (G1 in 150 mM $K^+$) in the presence of different concentrations of TTAPE in 5 mM Tris-HCl buffer (pH=7.5). Excitation wavelength: 350 nm.
Figure 58:
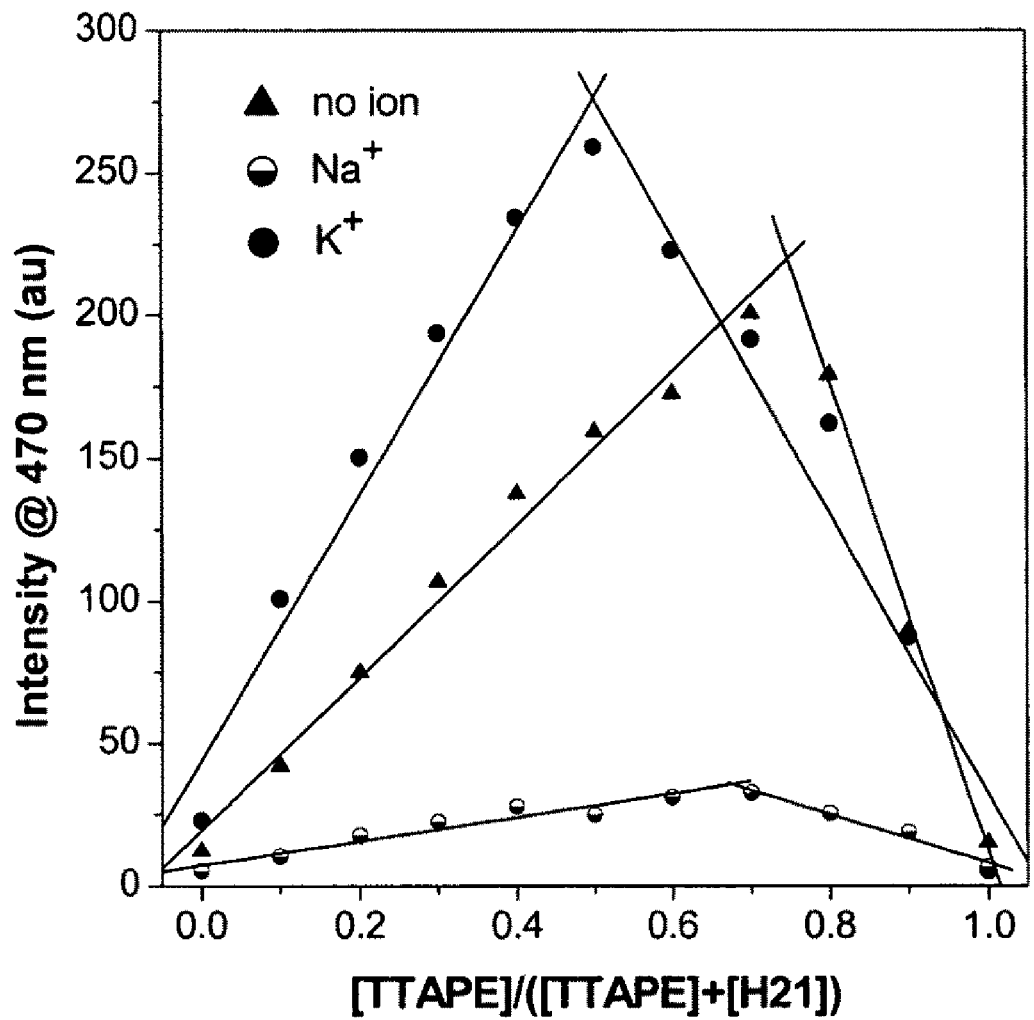
FIG. 58 shows the job plots for the binding of TTAPE to H21 in Tris-HCl (blue), K-Tris (black), or Na-Tris (red) buffer solution (pH=7.50). The sum of TTAPE and DNA concentrations was kept at 10 μM. Fluorescent intensities for the bound TTAPE at 470 nm are normalized to the maximum increase in each case. The y-axis represents the difference in PL intensity for mole fraction of ligand ($\chi_L$) in DNA. Intercept mole fraction values were determined from least-squares fits to the linear data portions, giving $\chi_{int}$ values of 0.50 (1:1 stoichiometry) for H21 in K-Tris, 0.67 (3:1) for H21 in Na-Tris, and 0.75 (4:1) for H21 in Tris-HCl, respectively.
Figure 59:
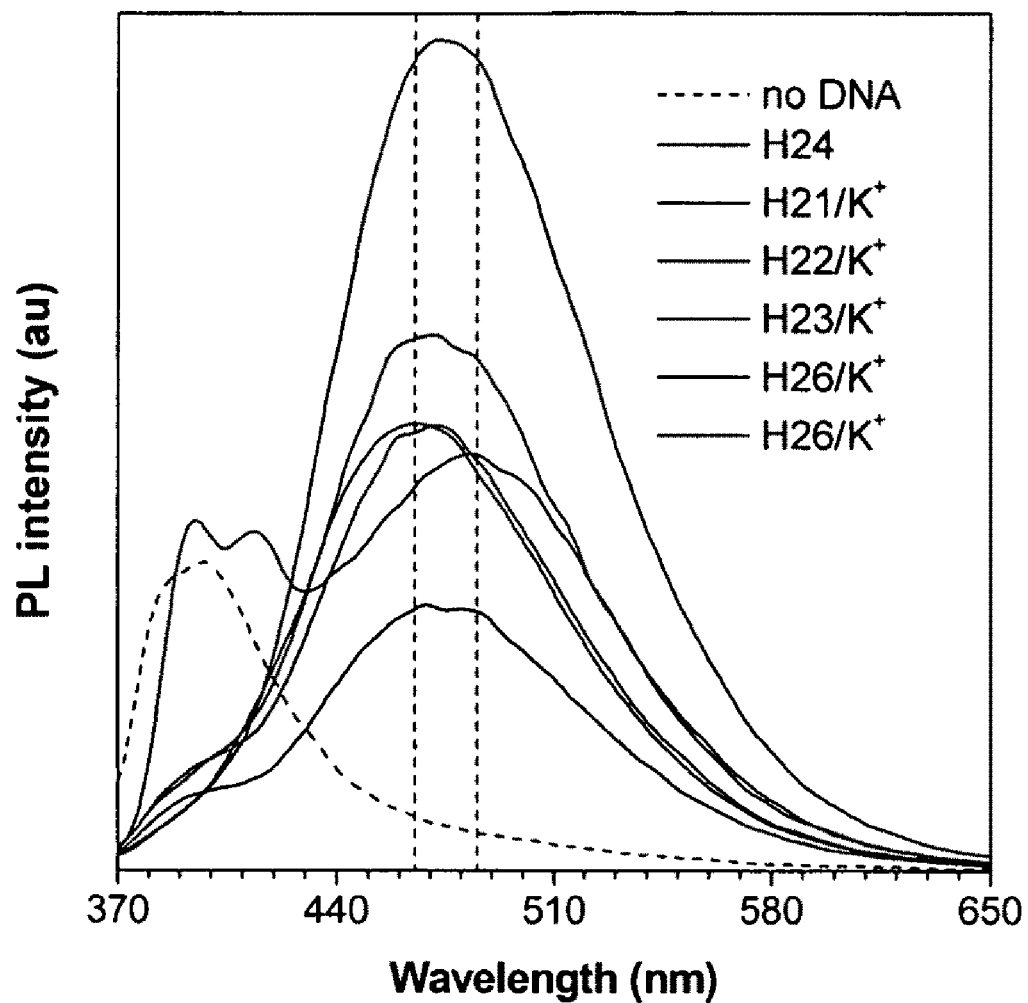
FIG. 59 shows the emission spectra of buffer solutions (pH=7.5) of TTAPE/DNA containing $K^+$. [TTAPE]=4.5 μM, [DNA]=4.5 μM. Excitation wavelength: 350 nm
Figure 60A:
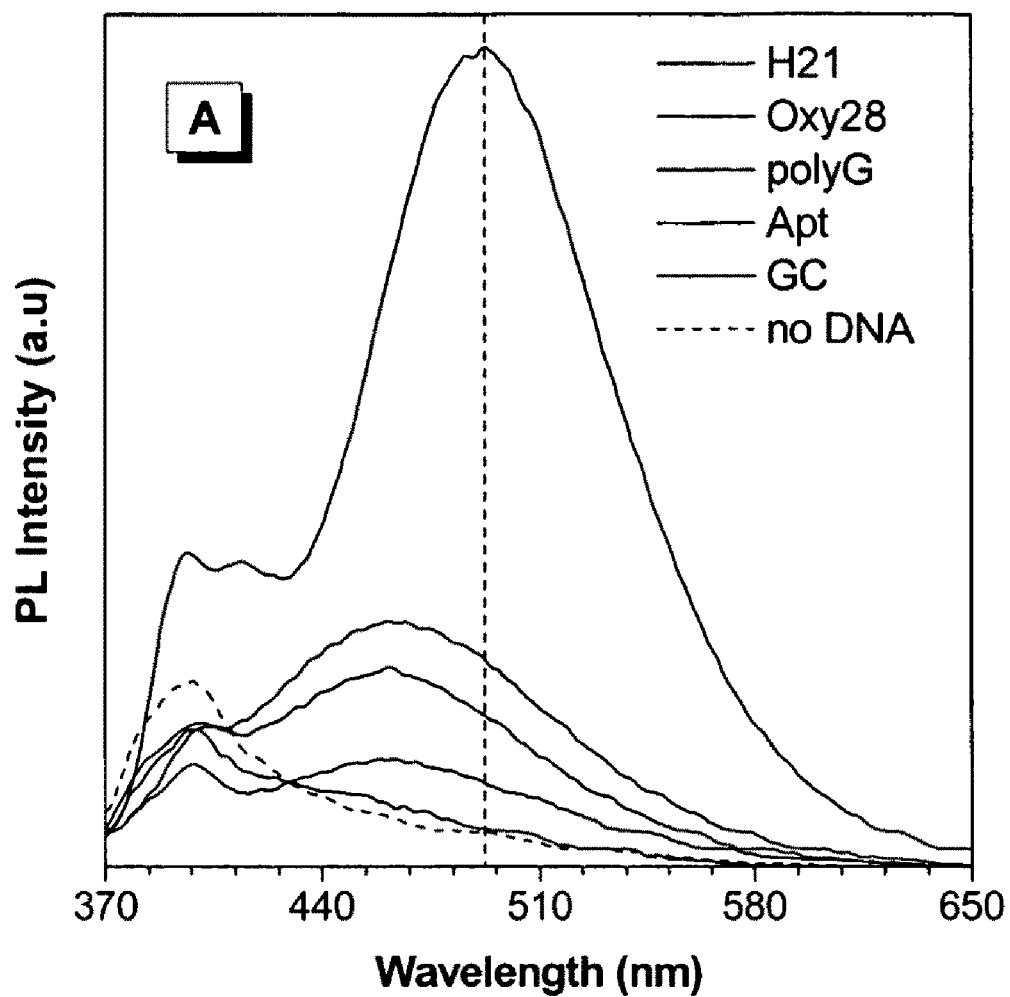
FIG. 60A shows the emission spectra of TTAPE with different G-rich DNA sequences in the presence of $K^+$. [TTAPE]= 4.5 μM; [DNA]=9 μM; [$K^+$]=0.5 M. Excitation wavelength: 350 nm
Figure 60B:
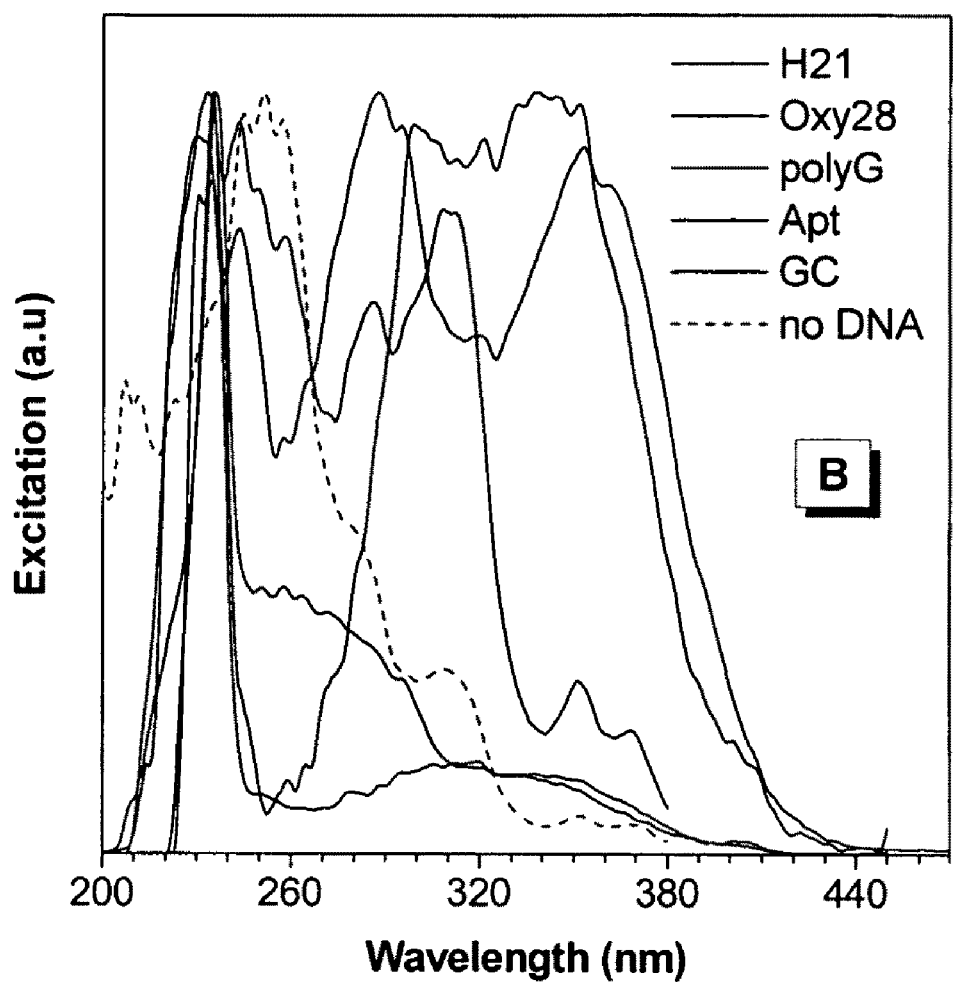
FIG. 60B shows the excitation spectra of TTAPE with different G-rich DNA sequences in the presence of $K^+$. [TTAPE]=4.5 μM; [DNA]=9 μM; [$K^+$]=0.5 M. Excitation wavelength: 350 nm
Figure 60C:
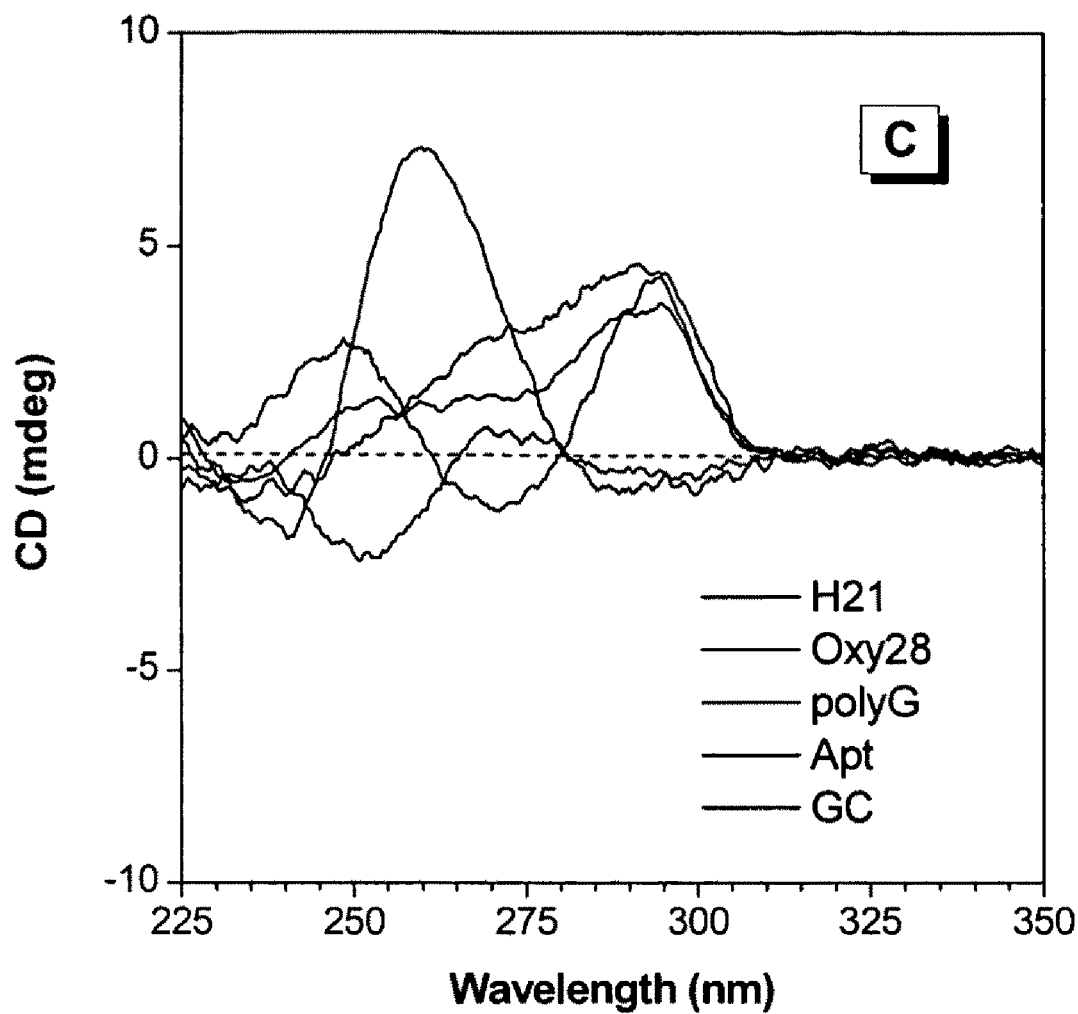
FIG. 60C shows the CD spectra of TTAPE with different G-rich DNA sequences in the presence of $K^+$. [TTAPE]=4.5 μM; [DNA]=9 μM; [$K^+$]=0.5 M. Excitation wavelength: 350 nm
Figure 61:
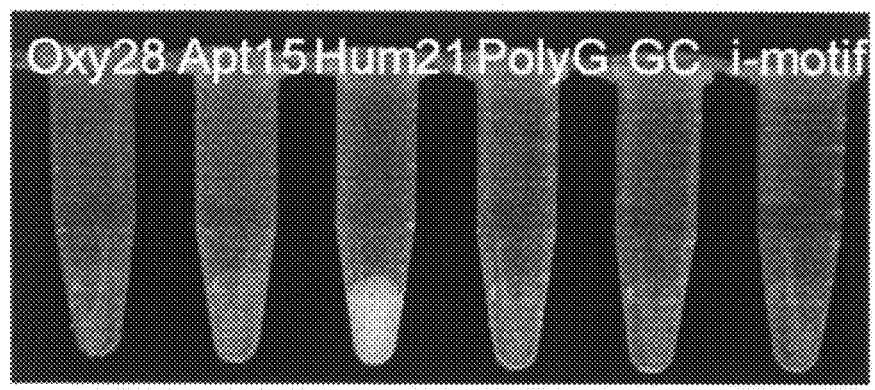
FIG. 61 is a photograph of $K^+$-Tris-HCl buffer solution of TTAPE in the presence of different DNAs under the illumination of a handheld UV lamp. [TTAPE]=4.5 μM, [DNA]= 4.5 μM, [$K^+$]=0.5 M.
Figures 62A, 62B:
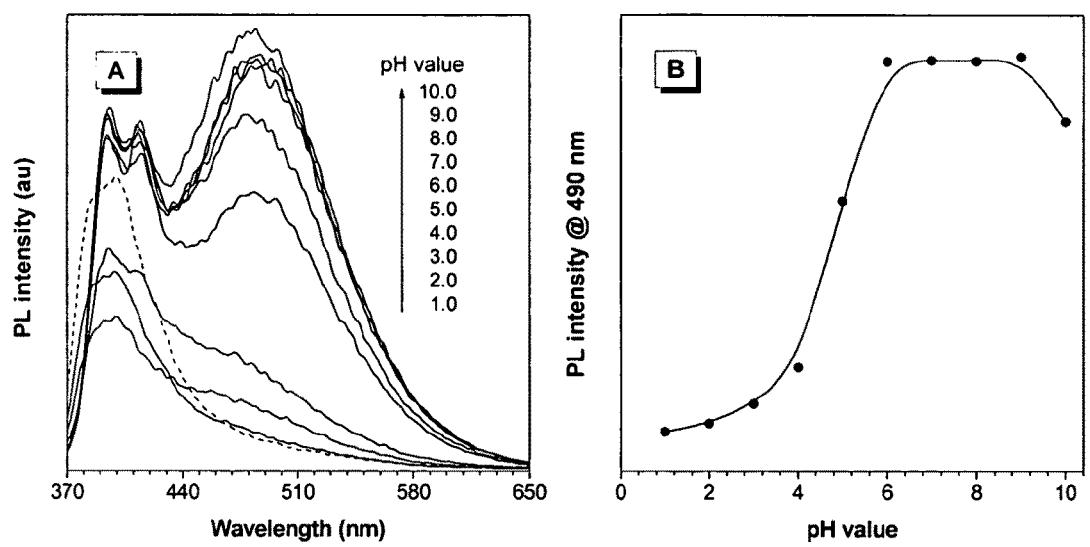
FIG. 62A shows the emission spectra of TTAPE/H21 containing $K^+$ under environments of different pH value. [TTAPE]=4.5 μM, [DNA]=4.5 μM, [$K^+$]=0.5 M. Excitation wavelength: 350 nm.
FIG. 62B shows the effect of pH value on the PL intensity at 490 nm of TTAPE/H21 in the presence of $K^+$. [TTAPE]= 4.5 μM, [DNA]=4.5 μM, [$K^+$]=0.5 M. Excitation wavelength: 350 nm.
Figure 63:
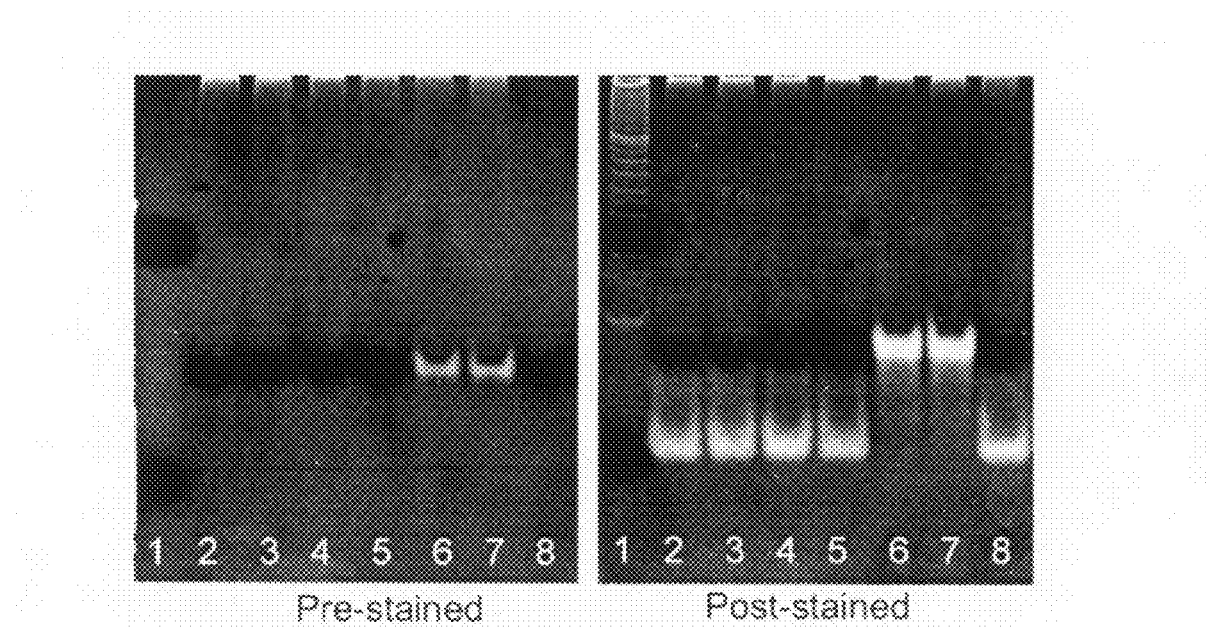
FIG. 63 shows the prestained poly(acrylamide) gels of (1) DNA ladder on the left side; (2) H21/TTAPE; (3) H21/$Na^+$/ TTAPE; (4) H21/$K^+$/TTAPE; (5) H21/$Ca^{2+}$/TTAPE; (6) H26/ TTAPE; (7) H26/$K^+$/TTAPE; (8) H21. On the right side the figure shows the post-stained gels with either 10 μM TTAPE for 10 min.
Figure 64:
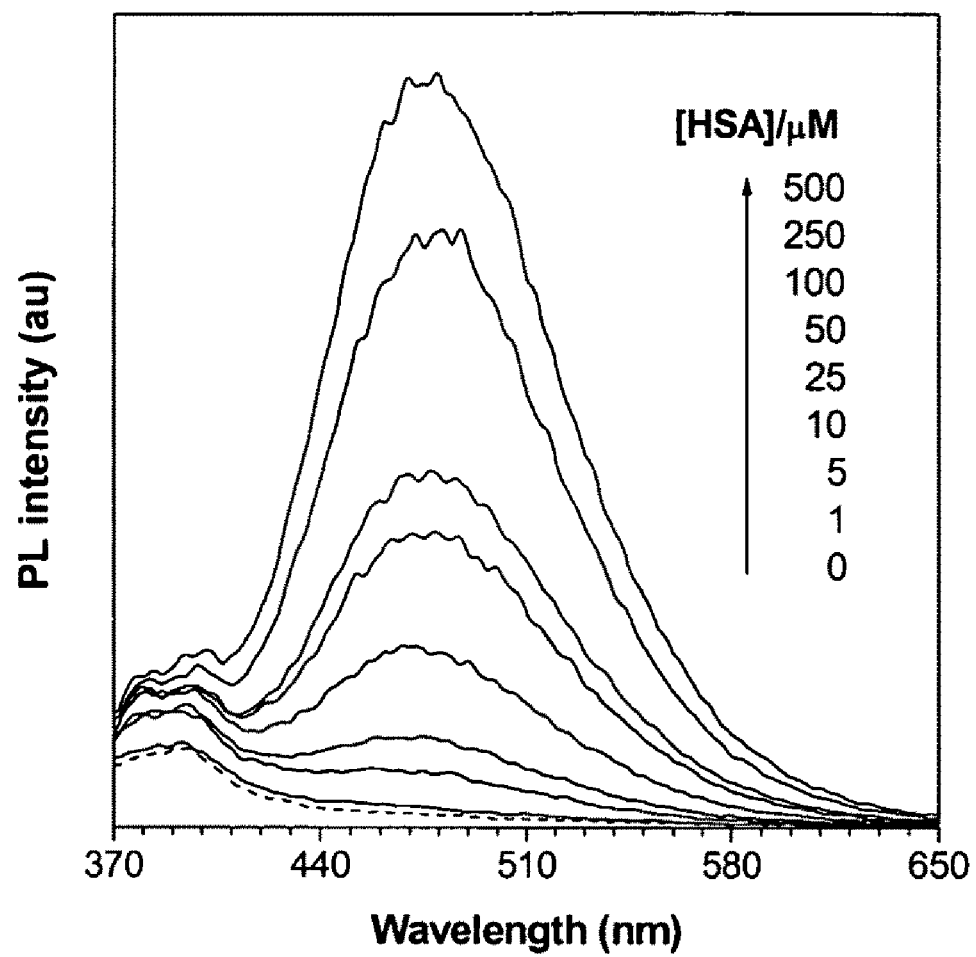
FIG. 64 shows the FL spectrum of SATPE with addition of HSA in artificial urine solution (pH=6.0). [SATPE]=5 μM. Excitation wavelength: 350 nm.
Figure 65:
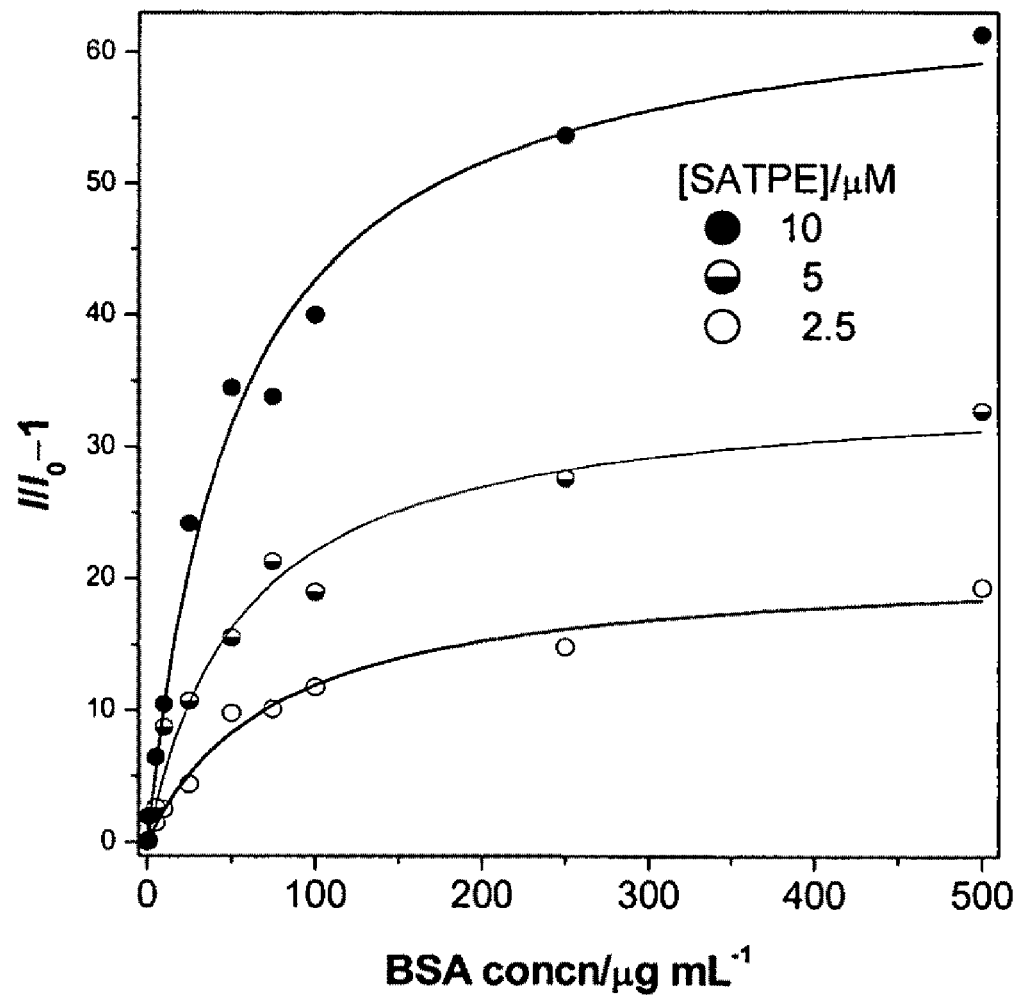
FIG. 65 shows the binding isotherm of BSA to different concentrations of SATPE in artificial urine (plot of FL intensity at 470 nm). Excitation wavelength: 350 nm.

TTAPE was prepared by the synthetic route shown in FIG. 49. Dehydrobromination of 4,4'-dihydroxybenzophenone (DHBP) with 1,2-dibromoethane in the presence of potassium carbonate yields 4,4'-bis(2-bromoethoxy)-benzophenone (BBEBP). McMurry coupling [S] of BBEBP produces 1,1,2,2-tetrakis[4-(2-bromoethoxy)phenyl]ethene (TBEPE), which is quaternized by triethylamine to furnish a salt 1,1,2, 2-tetrakis[4-(2-triethylammonioethoxy)phenyl]ethene tetrabromide (TTAPE). The reaction intermediates and final product were fully characterized by spectroscopic methods, from which satisfactory analysis data were obtained. TBEPE is completely soluble chloroform, acetonitrile (AN) and THF, slightly soluble in ethanol and methanol, but totally insoluble in water. TTAPE, on the other hand, is soluble in water as well as all the organic solvents mentioned above, due to the amphiphilic nature of the ammonium salt.

AIE Effect

Figure 31:
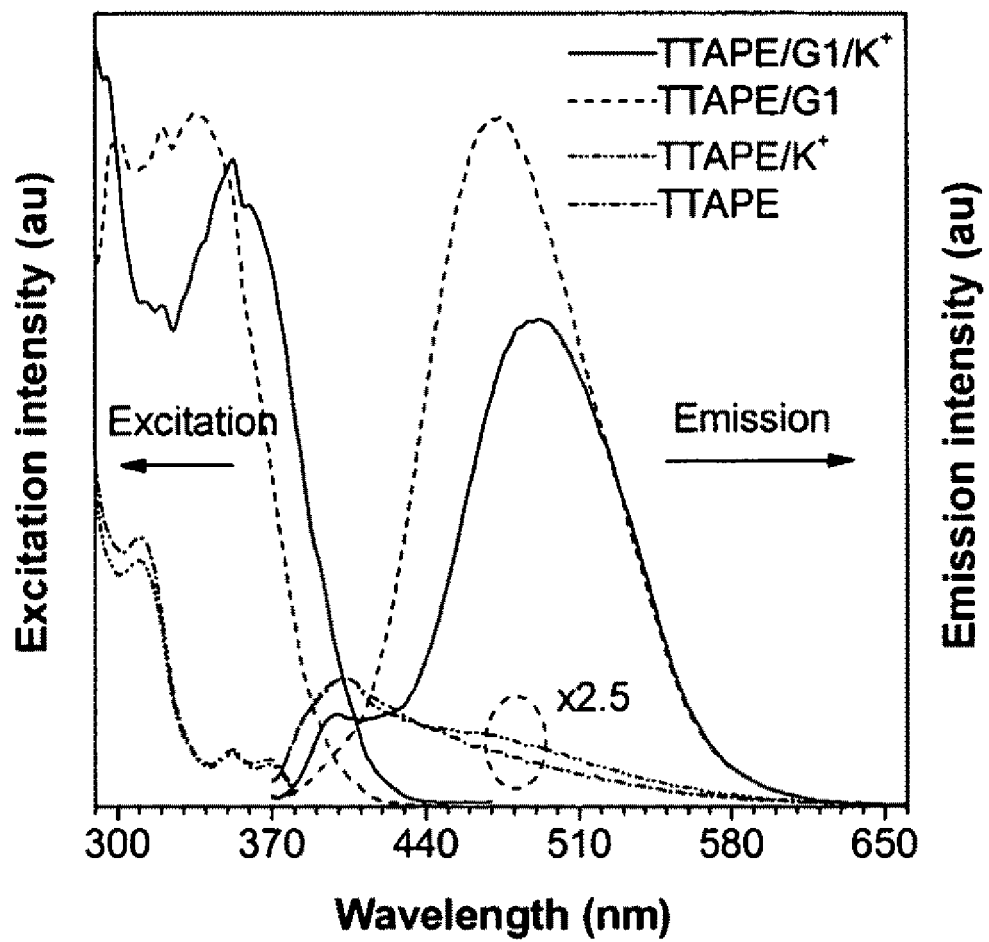
FIG. 31 shows the excitation and emission spectra of TTAPE solutions in a Tris-HCl buffer in the presence or absence of $K^+$ ion and/or G1. [TTAPE]=4.5 μM, [G1]=9 μM, [$K^+$]=0.5 M; $\lambda_{ex}$=350 nm.

When dissolved in its good solvents at molecular level, TBEPE is virtually nonluminescent. Addition of poor solvents into its solutions dramatically boosts its emission efficiency. A dilute AN solution of TBEPE, for example, emits a faint UV light (FIG. 31). When a large amount of water (99 vol %) is added, the resultant mixture shows an intense FL spectrum peaked at 479 nm. Since water is a nonsolvent of TBEPE, its molecules must have aggregated in the aqueous mixture. TBEPE is therefore induced to emit by aggregate formation; in other words, it is AIE active. The mixture is transparent and homogeneous, suggesting that the dye aggregates suspended in the mixture are nanosized. In the dilute AN solution, the phenyl rings of TBEPE can rotate against its central olefinic double bond, which nonradiatively deactivates the excited state and renders the dye nonemissive. The intramolecular rotations are largely restricted in the nanoaggregates in the An/water mixture. This blocks the nonradiative decay channel of the dye and makes it highly luminescent.

Figure 26A:
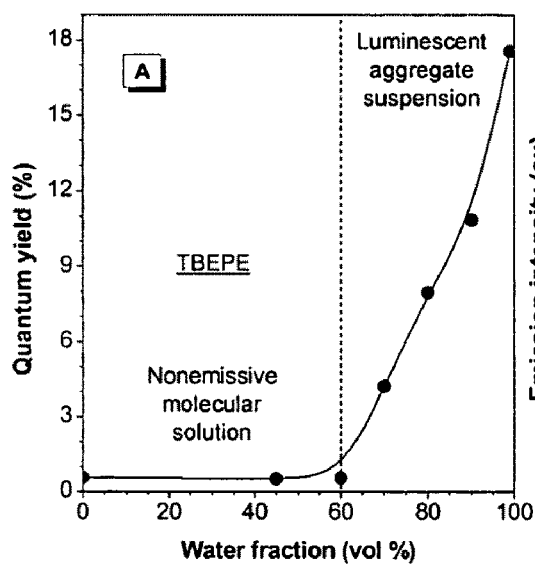
FIG. 26A is a plot of quantum yield of TBEPE vs. composition of AN/water mixture.

Changes in the $\Phi_F$ values of TBEPE in the AN/water mixtures with different water contents further confirm its AIE nature. In the AN solution, TBEPE exhibits a negligibly small $\Phi_F$ value (~0.5%), which remains almost unchanged till up to ~60% of water is added (FIG. 26A). Afterward the $\Phi_F$ value starts to increase swiftly. In the AN/water mixtures with lower water fractions, TBEPE is genuinely dissolved, while in the aqueous mixtures with higher water fractions (>60%), the dye molecules cluster together due to the deterioration in the solvating power of the mixture. When the water fraction is increased to 99 vol %, the $\Phi_F$ value is increased to ~18%, which is ~35-fold higher than that in the pure AN solvent. The absolute $\Phi_F$ values of the aggregates should be much higher than the relative ones given in FIG. 26A, if the light scattering caused by the Mie effect of the nanoaggregates is taken into consideration.

Figure 26B:
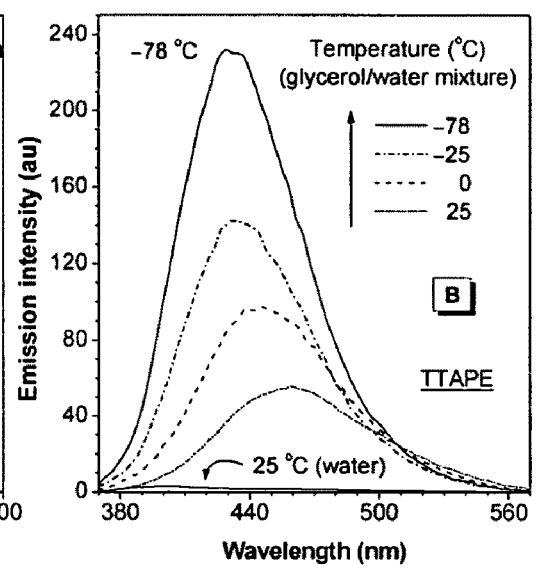
FIG. 26B shows the FL spectra of TTAPE in a glycerol/water mixture (99:1 by volume) at different temperatures; the spectrum of its water solution at 25° C. is shown for comparison. [dye]=5 μM; $\lambda_{ex}$=350 nm.

TTAPE is completely soluble in water. Owing to its amphiphilic nature associated with its quaternary tetraalkylammonium moieties, addition of AN, THF or methanol into its water solution fails to make the dye molecules aggregate. As a result, the emissions from TTAPE in all these mixtures are as weak as that in the pure water solution. However, increasing viscosity and decreasing temperature of the solution of TTAPE can activate its FL process. As can be seen from FIG. 26B, TTAPE in a viscous glycerol/water mixture at 25° C. emits an intense blue light of 464 nm. When the viscous mixture is cooled to −78° C., its emission intensity is further increased. At the cryogenic temperature, solvent viscosity is increased and molecular motions are further hampered. TTAPE can thus be induced to emit by restricting its intramolecular rotations, which is the exact cause for the AIE effect of its TBEPE cousin (vide supra).

DNA Probing

Figures 27A, 27B:
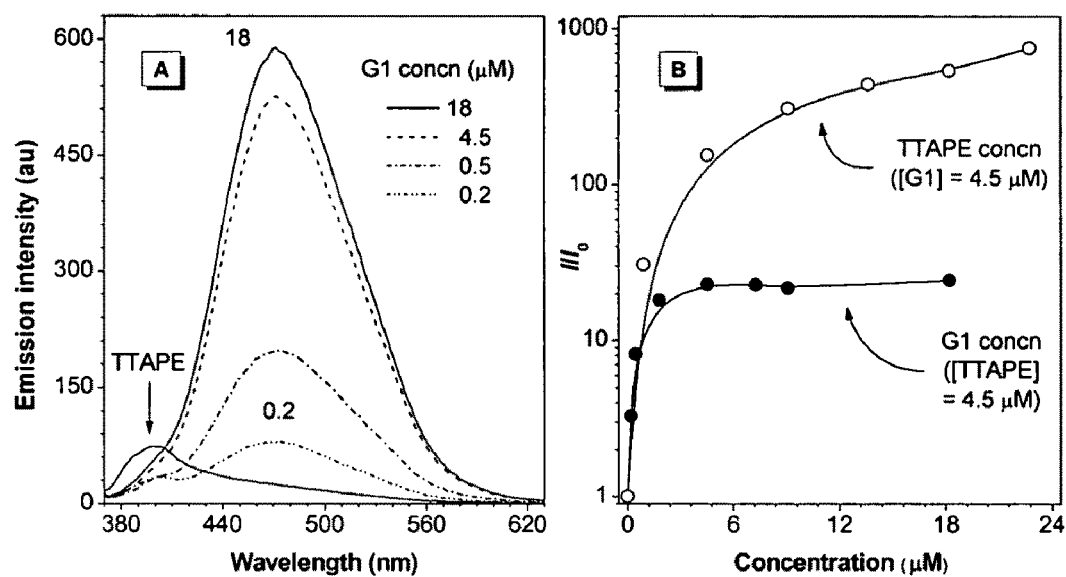
FIG. 27A shows the fluorimetric titration of G1 to an aqueous solution of TTAPE (4.5 μM) in 5 mM Tris-HCl buffer (pH=7.50).
FIG. 27B shows the change in emission intensity (I) at 470 nm with variation in concentration of G1 or TTAPE; $\lambda_{ex}$=350 nm.
Figure 28:
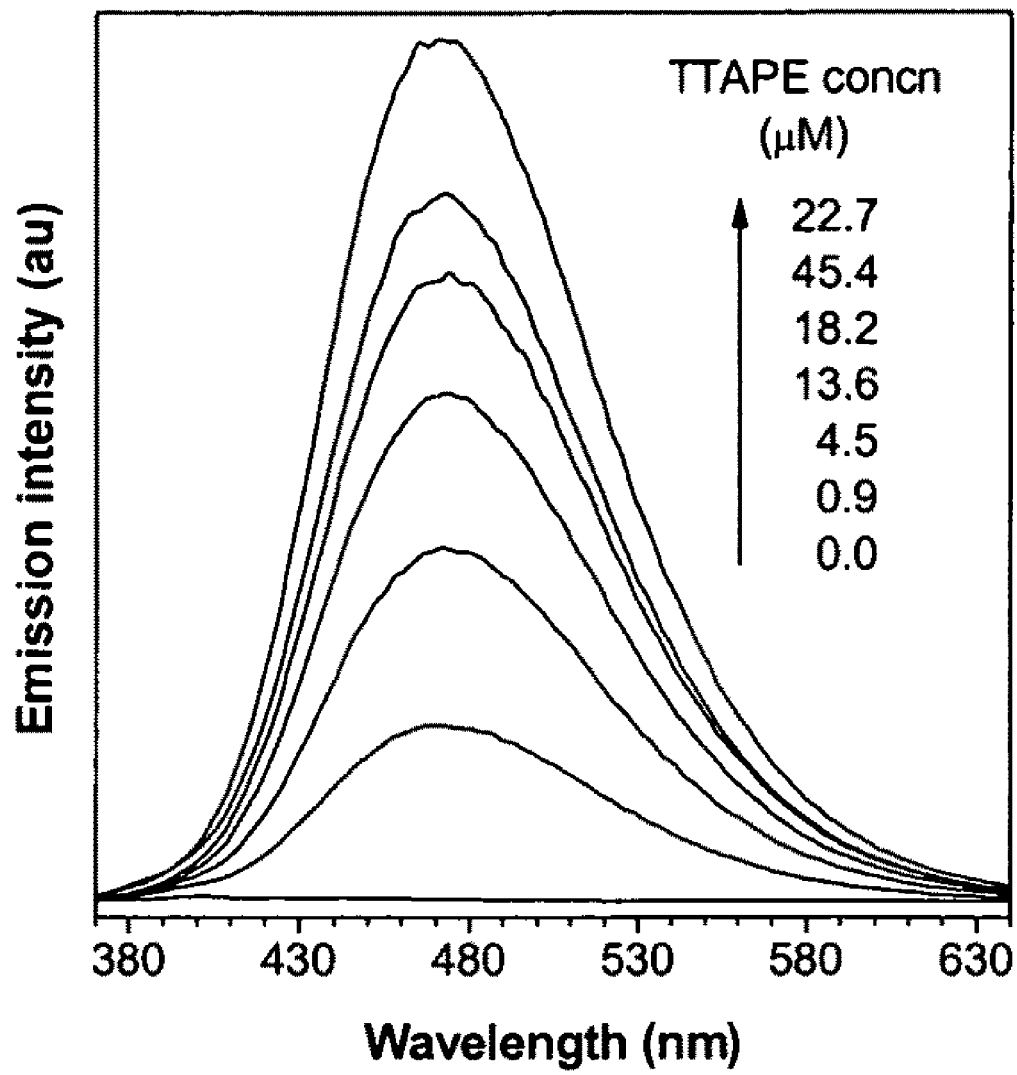
FIG. 28 shows the emission spectra of TTAPE in the presence of a solution of G1 (4.5 μM) in 5 mM Tris-HCl buffer (pH=7.50).

G1 is a 21-mer ssDNA that mimics human telomeric sequence. When the DNA is added into a solution of TTAPE in a tris(hydroxymethyl)aminomethane (Tris)-HCl buffer, the solution starts to luminesce (FIG. 27A). Similar FL "light up" phenomenon has been observed in the thiazole orange system. The $I/I_0$ ratio of TTAPE at 470 nm increases rapidly in a narrow DNA concentration range and reaches its maximum at [G1]≈5 µM (FIG. 27B). While conventional FL dyes suffer from self-quenching problem at high dye concentrations, the FL of TTAPE is continuously intensified with increasing its concentration (FIG. 28 and FIG. 27B), thanks to its unique AIE feature. In the aqueous buffer, the cationic dye spontaneously binds to the anionic DNA via electrostatic attraction, resulting in the formation of a TTAPE/G1 complex. Hydrophobic interaction between TTAPE and G1 may have also played a role in the binding process. These intermolecular forces lock conformations of the TTAPE molecules bound to the G1 strands. Consequently, the intramolecular rotations of TTAPE are restricted, which thus blocks its radiationless relaxation pathways and activates its FL process.

The FL "turn-on" switching of TTAPE by binding to G1 strand inspires us to check whether it can be used as a DNA marker in the PAGE assay. Electrophoresis assay of G1 was performed on a Hoefer miniVE system in 1×TBE buffer under nondenaturing conditions using a 20% native poly(acrylamide) gel at 100 V for 3 h at 4° C. An AlphaDigiDoc™ system with a DE-500 MultiImage™ II light cabinet and an ML-26 UV transilluminator (Alpha Innotech) was used for data collection and analysis. The gel was poststained with a 10 µM TTAPE solution for 5 min at room temperature, rinsed with distilled water, and photographed under UV light at 290-330 nm by the gel documentation system. EB was used to poststain the gel in parallel for comparison. Concentrations of G1 in the range of 0.5-10.0 µM were used to check the visualizability of the dye-stained DNA in the PAGE assay.

Figure 29:
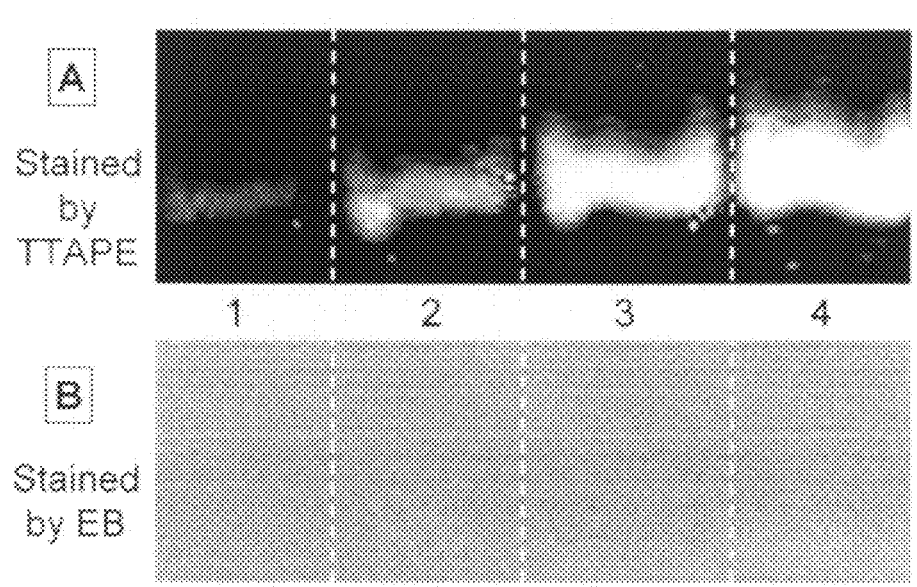
FIG. 29 shows the PAGE assays of G1 at concentrations of 0.5, 1.0, 5.0 and 10.0 μM (lanes 1-4). The gels were post-stained by (A) 10 μM TTAPE and (B) 1.3 μM EB for 5 min.

After running PAGE of G1 in a Tris-borate-ethylene-diaminetetraacetic acid (TBE) buffer, the gel is stained by a TTAPE solution for 5 min. Upon UV illumination, the stained gel shows FL bands at various G1 concentrations (FIG. 29A). Ethidium bromide (EB) is a widely used visualization agent for PAGE assay. The gel stained by EB exhibits bright background emissions (FIG. 29B), although a much lower EB concentration has been used. The G1 bands are not visualized until the gel has been stained by EB for as long as 30 min. Band visualization by EB is usually realized by its intercalation into the hydrophobic region of DNA, which makes the staining a slow process. On the other hand, the FL of TTAPE is activated by its spontaneous electrostatic interaction with charged surface of DNA, which can be achieved in a short time. Sensitivity test reveals that TTAPE can detect ~0.5 µM of G1. The detection limit can be further lowered by increasing the dye concentration, as suggested by the solution $I/I_0$ data (c.f., FIG. 27B). The present subject matter thus has the advantages of fast response and high sensitivity, in addition to its excellent miscibility with aqueous media.

Effects of Cationic Species

Among the cationic species, $Na^+$ and $NH_4^+$ are known to be able to induce quadruplex formation but the TTAPE emission is still diminished by these cations. It is known that the conformation of G-quadruplex is highly dependent on the type of cationic species. In the presence of $Na^+$, G1 exhibits a CD spectrum with positively and negatively signed Cotton effects at 295 and 265 nm, respectively (cf., FIG. 30). This suggests the formation of a G-quadruplex with an antiparallel strand alignment, which differs from the G-quadruplex with mixed parallel/antiparallel strand arrangements formed in the presence of $K^+$. The difference in the geometric conformation may account for the observed difference in the emission behavior. This offers an attractive possibility of using TTAPE as a bioprobe to discriminate between quadruplexes with different conformations.

Figure 36:
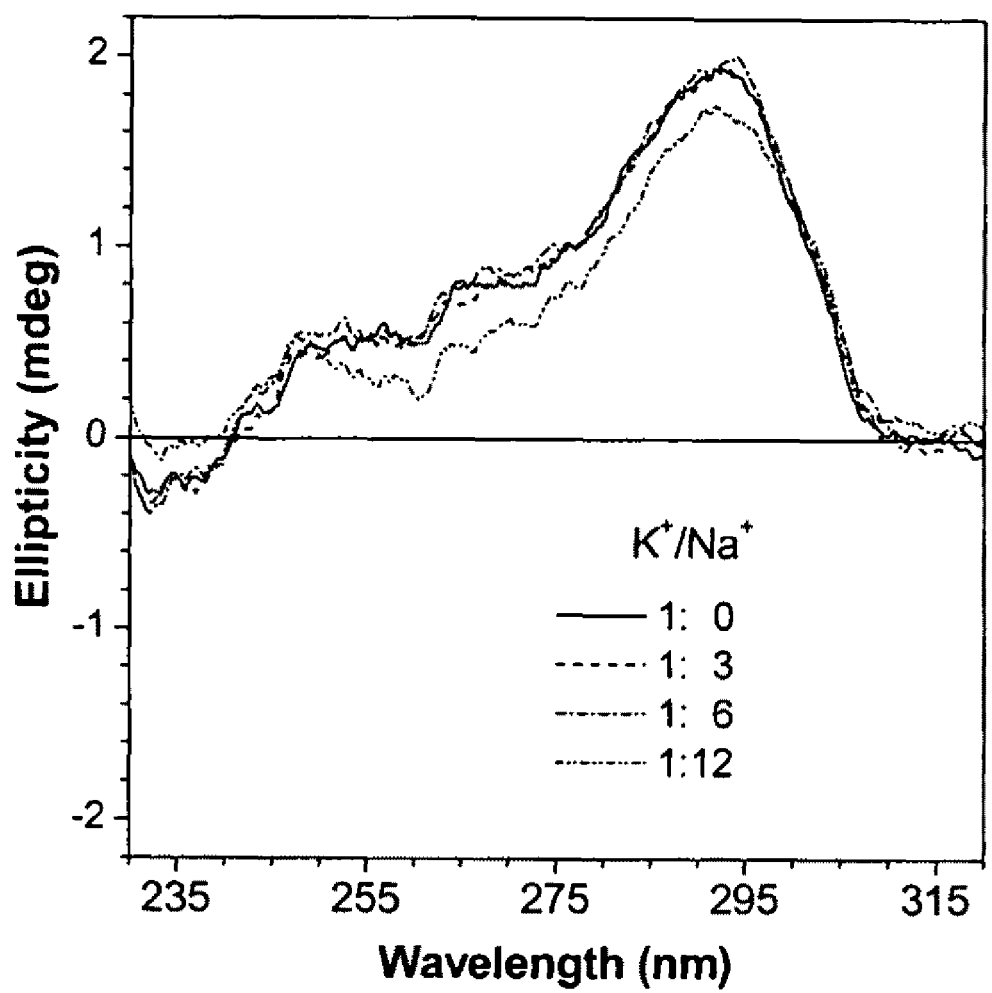
FIG. 36 is a CD spectra of the G1/TTAPE/$K^+$ solutions in a Tris-HCl buffer titrated by different amounts of $Na^+$ ions. [G1]=9 μM, [TTAPE]=4.5 μM, [$K^+$]=100 mM; $\lambda_{ex}$=350 nm.

Various electrolytes exist in the biological systems and excess or absence of one or two of these ionic species can cause biomolecules to undergo conformational transitions, resulting in either favorable biological effect or undesirable dysfunction. How does coexistence of two cationic species, e.g., physiologically important $K^+$ and $Na^+$, affect the quadruplex conformation? As can be seen from FIG. 34B, addition of $Na^+$ into TTAPE/G1/$K^+$ gradually decreases the intensity of the quadruplex-specific emission at 492 nm. The large amount of $Na^+$ ions drives the dye molecules chemisorbed on the G-quadruplex surface into the aqueous media, resulting in the observed emission attenuation. The spectral profile, however, remains unchanged, even when the amount of the added $Na^+$ ions is 12-fold higher than that of $K^+$, indicating that the G-quadruplex has maintained its structural integrity. This is further proved by the CD data: the CD spectrum of the G-quadruplex formed in the presence of $K^+$ is unaffected by the perturbations from the excess amount of externally added $Na^+$ ions (FIG. 36). This suggests that the $K^+$-containing quadruplex is more stable than the $Na^+$ one or that $K^+$ is superior to $Na^+$ in inducing/stabilizing the quadruplex structure.

It is clear that TTAPE is highly affinitive to $K^+$-containing G-quadruplex but not its $Na^+$ cousin (Example 30). Isothermal titration calorimetry (ITC) measurements are performed, in an effort to understand the thermodynamic basis for the binding affinity difference. ITC is a sensitive technique for the studies of bimolecular processes and can provide direct information about binding affinities and associated thermodynamic parameters. A calorimetric titration experiment was performed at 25.00±0.01° C. on a MicroCal VP-ITC apparatus. G1 solutions for the ITC experiments were prepared in all-potassium (K-Tris: 5 mM Tris-HCl and 150 mM KCl) or all-sodium (Na-Tris: 5 mM Tris-HCl and 150 mM NaCl) buffer at pH 7.50, as required. The buffer solution of G1 was heated to 85° C. and cooled slowly to ensure the folding of the DNA into G-quadruplex structure. For a typical titration, a series of 10 μL aliquots of TTAPE solution were injected into the G1/M$^+$ solution at a 240 s interval. The heat for each injection was determined by the integration of the peak area in the thermogram with respect to time. Blank titration was conducted by injecting TTAPE into the sample cell containing only buffer under the same condition. The interaction heat was corrected by subtracting the blank heat from that for the TTAPE/G1 titration. The $k_b$ values were derived by fitting the isotherm curves with Origin 5.0 software.

Figures 37A, 37B:
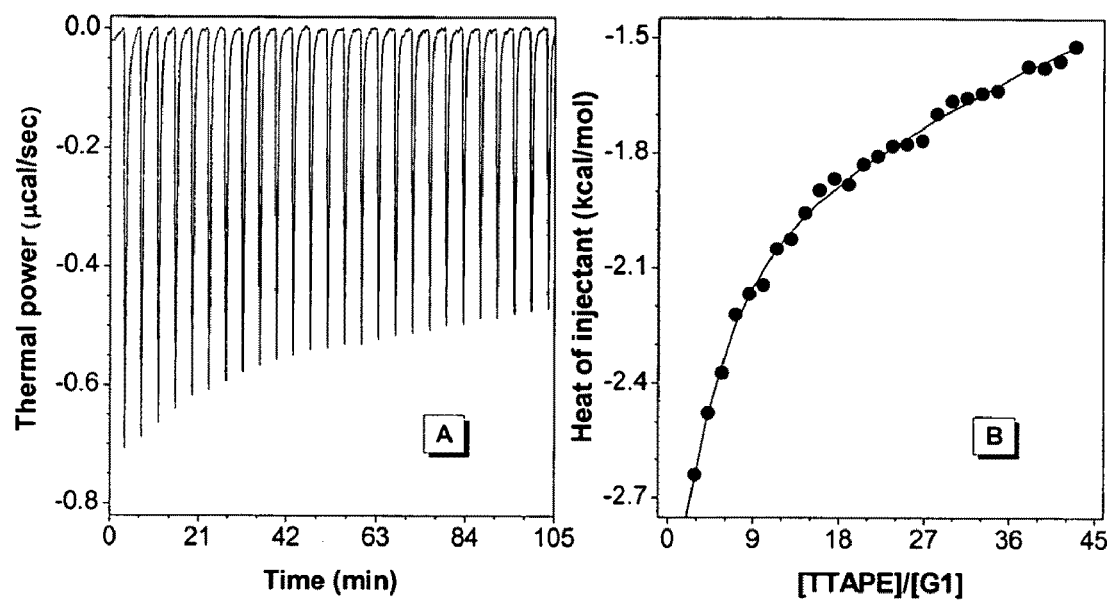
FIG. 37A shows the calorimetric curves for titration of G1 in a K-Tris buffer with serial injections of TTAPE at 25° C.
FIG. 37B shows the binding isotherm as a function of [TTAPE]/[G1] molar ratio in the buffer solution

As can be seen from FIG. 37A, injection of a tiny aliquot (10 μL) of a TTAPE solution into a G1/K$^+$ buffer yields a large exothermic peak. Fitting the data of integrated heat generated per injection in the binding isotherm (FIG. 37B) gives a binding constant ($K_b$) of 2.4×10$^5$ M$^{-1}$, from which a Gibbs energy ($\Delta G°$) of −7.3 kcal mole$^{-1}$ is obtained. However, in the case of the Na$^+$ titration, the binding constant is too small to be determined accurately from the ITC data.

Biosensing Processes

Figure 45:
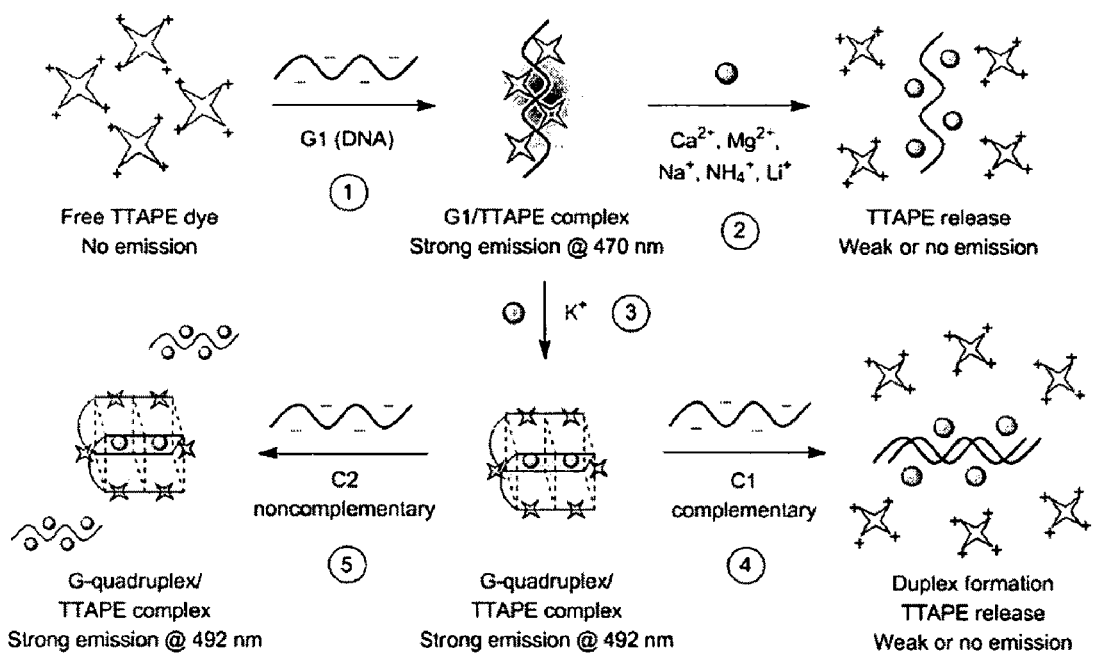
FIG. 45 shows the fluorescent bioprobing processes of TTAPE.

It has now become clear that TTAPE is a fluorescent marker that can perform multiple functions, including DNA probing, G-quadruplex recognition, and potassium-ion sensing (FIG. 45). The nonemissive TTAPE molecules dissolved in the aqueous buffer become highly luminescent upon binding to G1 via mainly electrostatic attraction, as the DNA binding restricts their intramolecular rotations (Process 1 of FIG. 45). Addition of competitive cations such as Li$^+$, Na$^+$, NH$_4^+$, Mg$^{2+}$ and Ca$^{2+}$ weakens or quenches the emission, because the cations drive the bound dye molecules back to solution (Process 2 of FIG. 45). Addition of K$^+$, however, induces G1 to fold into a G-quadruplex structure, resulting in a red shift in the emission spectrum (Process 3 of FIG. 45). Hybridization with a complementary ssDNA (C1) unfolds the G-quadruplex and affords a duplex. The K$^+$ ions in the solution compete with the TTAPE molecules for binding with the dsDNA. The dye molecules are released back to the solution and the emission is thus diminished (Process 4 of FIG. 45). On the other hand, a noncomplementary ssDNA strand (C2) does not disassemble the G-quadruplex structure. As a result, the characteristic emission of the quadruplex/TTAPE complex at 492 nl is preserved (Process 5 of FIG. 45).

A water-soluble TPE derivative, i.e., TTAPE, with novel AIE characteristics has now been synthesized. It has been shown that TTAPE can function as a "light-up" bioprobe for DNA detection, G-quadruplex identification, and potassium-ion sensing. The data presented demonstrates that TTAPE can be utilized as an external fluorescent marker to study conformational structures, to monitor folding processes of label-free oligonucleotides with G-rich strand sequences, and to visualize DNA bands in PAGE assay. The spectral red-shift diagnostically signals the presence of quadruplex structure, allowing a visual distinguishment of G-quadruplex from other DNA conformations. The results of studies have application in biomedicine studies, especially to high-throughput quadruplex-targeting anticancer drug screening. Further studies, especially computational simulations of the biosensing processes, are ongoing in our laboratories in an effort to better understand the binding modes of TTAPE with DNA.

EXAMPLES

The following examples are illustrative of the presently described subject matter and are not intended to be limitations thereon.

Example 1

1,2-Bis(4-hydroxyphenyl)-1,2-diphenylethylene (TPE-OH)

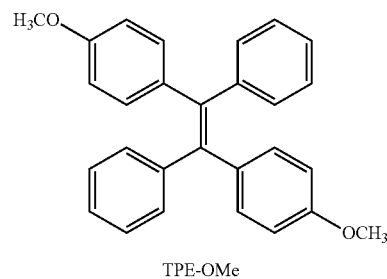

TPE-OMe

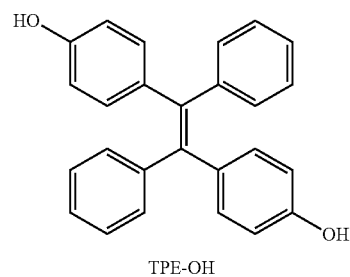

TPE-OH

A suspension of p-methoxybenzophenone (1.06 g, 5.0 mmol), 1.34 equiv of $TiCl_3/AlCl_3$ (5.81 g, 6.7 mmol), and 25 equiv of Zn dust (8.01 g, 122.0 mmol) in 100 ml of dry THF was refluxed for 20 h. The reaction mixture was cooled to room temperature and filtered. The filtrates were evaporated and the crude product was purified by a silica gel column using hexane as eluent. 1,2-Bis(4-methoxyphenyl)-1,2-diphenylethene (TPE-OMe) was isolated in 91% yield.

TPE-OMe (1.40 g, 3.56 mmol) was dissolved in 20 ml of dichloromethane (DCM) in a 100 ml flask, and the flask was placed in an acetone-dry ice bath at −78° C. A solution of 3.59 g (14.3 mmol) of boron tribromide in 10 ml of DCM was added carefully to the mixture under stirring. The resultant mixture was allowed to warm to room temperature overnight under stirring. The reaction product was hydrolyzed by careful shaking with 20 ml of water. The organic phase was separated and concentrated by a rotary evaporator. The crude product was purified by recrystallization from THF/methanol to afford a white solid in 97% yield.

Characterization data of TPE-OMe: $^1H$ NMR ($CDCl_3$, 300 MHz) δ (ppm): 7.10-7.06 (m, 10H), 6.93 (t, 4H), 6.64 (t, 4H), 3.74 (s, 6H). $^{13}C$ NMR ($CDCl_3$, 75 MHz) δ (ppm): 158.0, 144.4, 139.7, 136.5, 132.6, 131.5, 127.8, 126.3, 113.2, 55.2. MS (TOF) m/e: 392.1 (M+, calcd. 392.2).

TPE-OH: $^1H$ NMR ($CDCl_3$, 300 MHz) δ (ppm): 7.11-7.02 (m, 10H), 6.88 (t, 4H), 6.56 (d, 4H). $^{13}C$ NMR ($CDCl_3$, 75 MHz) δ (ppm): 154.1, 144.2, 139.7, 135.5, 132.8, 131.5, 127.8, 126.3, 114.7. MS (TOF) m/e: 363.1 [(M-H)+, calcd: 363.1].

Example 2

1,2-Diphenyl-1,2-bis(4,4'-(3-sulfonato)propoxyl) phenylethylene (TP-SO3) or (SATPE)

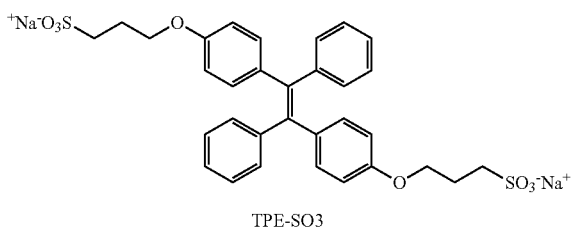

TPE-SO3

Into a 100 m round-bottom flask were added TPE-OH (0.5 g, 1.37 mmol) and 20 m of anhydrous ethanol under nitrogen. The mixture was stirred until all solids disappeared. A mixture of NaOEt (0.20 g, 3.0 mmol) in 20 ml ethanol was added dropwise and stirred for 1 h, causing the colorless solution to turn orange-red. Into the solution was added 0.35 g of 1,3-propanesultone (2.88 mmol) in 20 m of ethanol. The mixture was vigorously stirred for 12 h and a white product precipitated out from the solution. The product was collected by filtration and washed with ethanol and acetone twice to give a white solid in 61% yield.

Characterization data of TPE-SO3: $^1H$ NMR (DMSO-d6, 300 MHz) δ (ppm): 7.25-7.13 (m, 6H), 7.08-7.02 (m, 4H), 6.95-6.90 (m, 4H), 6.81-6.73 (m, 4H), 4.09-4.02 (m, 4H), 2.66-2.58 (m, 4H), 2.08-2.02 (m, 4H). $^{13}C$ NMR (DMSO-d6, 75 MHz) δ (ppm): 157.0, 143.9, 139.2, 135.5, 131.9, 130.8, 127.8, 126.2, 113.8, 66.4, 47.9, 25.3. MS (TOF) m/e: 631.1 [(M+2H)+−Na, calcd. 631.1], 609.2 [(M+3H)$^+$-2Na, calcd. 609.1].

Example 3

N,N'-[1,2-Diphenyl-1,2-bis(1,4-phenoxyethyl)vinyl] bis(triethylammonium bromide) (TPE-C2N+)

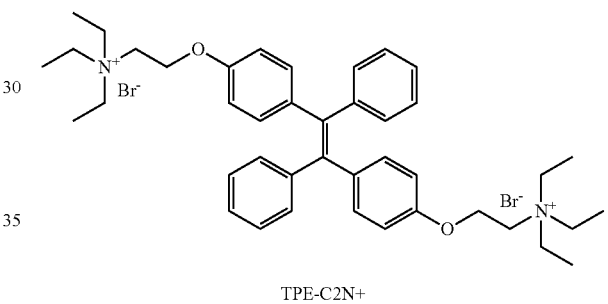

TPE-C2N+

To a mixture of sodium hydride (84 mg) and 1,2-bis(4-hydroxyphenyl)-1,2-diphenylethene (0.50 g) in dry dioxane (20 ml), 1,2-dibromoethane (1.50 g) was added at room temperature. The mixture was heated to reflux and stirred for 24 h. After filtration and concentration, the product was isolated and purified by silica gel chromatography using chloroform/hexane (1:1 v/v) as elute. 1,2-Bis[4-(2-bromoethoxy)phenyl]-1,2-diphenylethene (TPE-C2Br) was obtained in 32% yield.

A 250 ml flask with a magnetic spin bar was charged with TPE-C2Br (100 mg) dissolved in 100 ml of THF. To this solution was added triethylamine (5 ml). The mixture was heated to reflux and stirred for 3 days. During this period, 10 ml of water was added at several intervals. THF and extra triethylamine were evaporated. The water solution was washed by chloroform three times. After solvent evaporation, the residue was washed with chloroform and acetone and then dried overnight in vacuo at 50° C. TPE-C2N+ was isolated in 56% yield.

Characterization data of TPE-C2Br: $^1$H NMR (300 MHz, CDCl$_3$), δ (ppm): 7.10-7.02 (m, 10H), 6.95-6.92 (m, 4H), 6.65-6.59 (m, 4H), 4.15-4.11 (m, 4H), 3.55-3.49 (m, 4H). $^{13}$C NMR (75 MHz, CDCl$_3$), δ (ppm): 156.6, 144.1, 139.8, 137.2, 132.7, 131.5, 127.8, 126.4, 114.0, 67.8, 29.3. MS (TOF), m/e: 578.03 ([M]+, calcd. 578.03).

TPE-C2N+: $^1$H NMR (300 MHz, CDCl$_3$), δ (ppm): 7.09-7.00 (m, 10H), 6.97-6.87 (m, 4H), 6.61-6.54 (m, 4H), 3.90-3.84 (m, 4H), 3.45-3.40 (m, 4H), 2.00-1.97 (m, 4H), 1.88-1.84 (m, 4H). $^{13}$C NMR (75 MHz, CDCl$_3$), δ (ppm): 157.9, 144.9, 140.3, 137.2, 133.2, 132.1, 128.3, 126.9, 114.2, 67.3, 34.2, 30.2, 28.6. MS (TOF), m/e: 634.09 ([M]+, calcd. 634.09).

Example 4

N,N'-[1,2-Diphenyl-1,2-bis(1,4-phenoxybutyl)vinyl]bis(triethylammonium bromide) (TPE-C4N+)

The synthesis of the below compound was carried out according to Example 3 by using the corresponding dibromobutane.

66.5, 55.6, 52.0, 25.5, 18.0, 7.2. MS (TOF), m/e: 789.50 ([M.2H$_2$O−HBr]+, calcd. 789.44).

Example 5

1,1,2,2-tetrakis(4-hydroxyphenyl)ethylene (DHTPE)

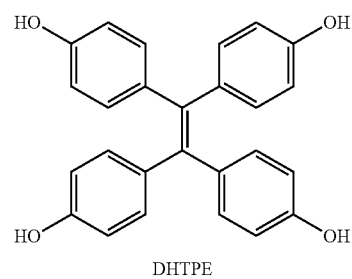

DHTPE

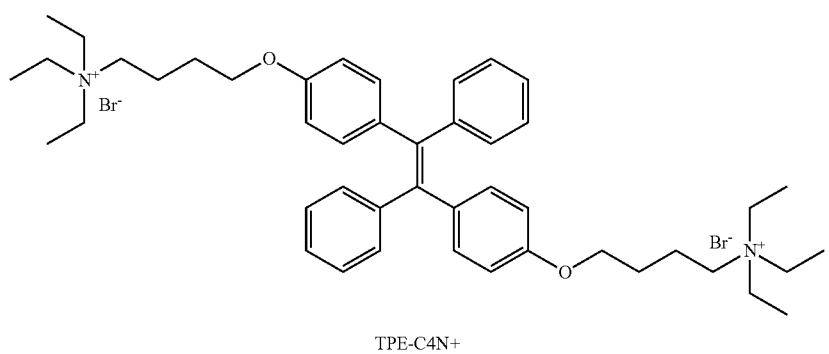

TPE-C4N+

Characterization data of TPE-C4Br: $^1$H NMR (300 MHz, CDCl$_3$), δ (ppm): 7.09-7.00 (m, 10H), 6.97-6.87 (m, 4H), 6.61-6.54 (m, 4H), 3.90-3.84 (m, 4H), 3.45-3.40 (m, 4H), 2.00-1.97 (m, 4H), 1.88-1.84 (m, 4H). $^{13}$C NMR (75 MHz, CDCl$_3$), δ (ppm): 157.9, 144.9, 140.3, 137.2, 133.2, 132.1, 128.3, 126.9, 114.2, 67.3, 34.2, 30.2, 28.6. MS (TOF), m/e: 634.09 ([M]+, calcd. 634.09).

TPE-C4N+: $^1$H NMR (300 MHz, d-DMSO), δ (ppm): 7.25-7.19 (m, 6H), 7.07-6.92 (m, 8H), 6.83-6.77 (m, 4H), 4.04-4.02 (m, 4H), 3.36-3.29 (m, 16H), 1.86-1.81 (m, 8H), 1.34-1.11 (m, 18H). $^{13}$C NMR (75 MHz, d-DMSO), δ (ppm): 156.9, 143.8, 139.3, 135.7, 132.0, 130.7, 127.9, 126.4, 113.7, A suspension of 4,4'-dihydroxybenzophenone (3.0 g, 14.0 mmol), 1 equiv of TiCl$_4$ (1.54 ml, 14.0 mmol), and 2 equiv of Zn dust (1.83 g, 28.0 mmol) in 100 ml of dry THF was refluxed for 20 h. The reaction mixture was cooled to room temperature and filtered. The filtrates were evaporated and the crude product was purified by a silica gel column using ethyl acetate (EA) as eluent. DHTPE was obtained as slight yellow powder of 83% yield.

Characterization data of DHTPE: $^1$H NMR (300 MHz, d-DMSO), δ (ppm): 9.24-8.94 (br), 7.07-7.04 (d, 4H), 6.95-6.95 (d, 4H), 6.70-6.56 (m, 4H), 6.47-6.42 (t, 4H). $^{13}$C NMR (75 MHz, CDCl$_3$), δ (ppm): MS (FAB), m/e: 391.2 ([M−4H]+, calcd. 392.1).

Example 6

N,N',N'',N'''-[1,2-Tetrakis(1,4-phenoxybutyl)vinyl]
tetrakis(triethylammonium bromide) (N+C4-TPE-C4N+)

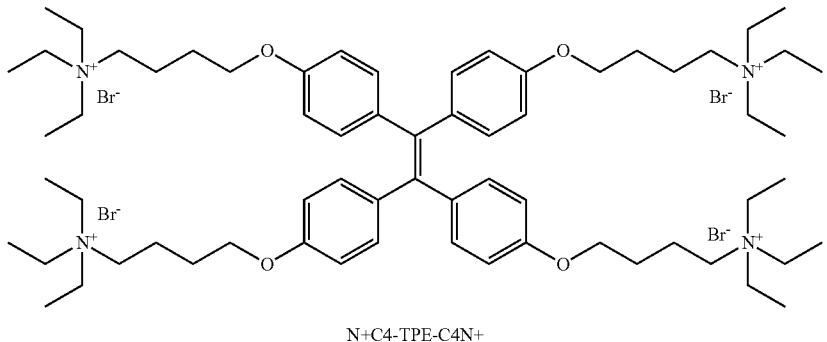

N+C4-TPE-C4N+

To a mixture of DHTPE (0.4 g, 20 mmol) and potassium carbonate in acetone, 1,4-dibromobutane (3 ml) was added and the mixture was heated to reflux and stirred for 24 h. After filtration and concentration, the product was isolated and purified by silica gel chromatography using chloroform/hexane (1:1 v/v) as eluent. The product 1,1,2,2-tetrakis(4-(4-bromobutoxy)phenyl)ethane (BrC4-TPE-C4Br) was obtained as white powder in 21% yield.

Characterization data of BrC4-TPE-C4Br: $^1$H NMR (300 MHz, CDCl$_3$), δ (PPM): 7.08-6.99 (m, 8H), 6.81-6.60 (m, 8H), 3.94-6.86 (m, 8H), 3.49-3.42 (m, 8H), 2.07-2.00 (m, 8H), 1.92-1.85 (m, 8H). $^{13}$C NMR (75 MHz, CDCl$_3$), δ (Ppm): 157.2, 136.6, 132.7, 129.5, 114.3, 66.9, 33.9, 29.9, 28.3. MS (FAB), m/e: 937.0 ([M]$^+$, calcd. 936.4).

N+C4-TPE-C4N+: $^1$H NMR (300 MHz, d-DMSO), δ (ppm): 7.29-7.27 (d, 1H), 7.10-7.08 (d, 1H), 6.83-6.80 (d, 7H), 6.83-6.80 (m, 7H), 3.91-3.83 (m, 8H), 3.23-3.18 (m, 16H), 2.89-2.84 (m, 8H), 1.70-1.65 (m, 20H), 1.17-1.06 (m, 40H). $^{13}$C NMR (75 MHz, d-DMSO), δ (ppm): 157.3, 135.6, 132.6, 130.6, 114.4, 67.2, 56.5, 52.9, 46.5, 26.4, 18.9, 8.0. MS (TOF), m/e: 933.6 ([M-4Br-3CH$_2$CH$_3$]+, calcd. 933.7).

Example 7

N,N',N'',N'''-[1,2-Tetrakis(1,4-phenoxyethyl)vinyl]
tetrakis(tri ethyl ammonium bromide) (N+C2-TPE-C2N+)

The synthesis of the below compound was carried out according to Example 6 by using the corresponding dibromoethane.

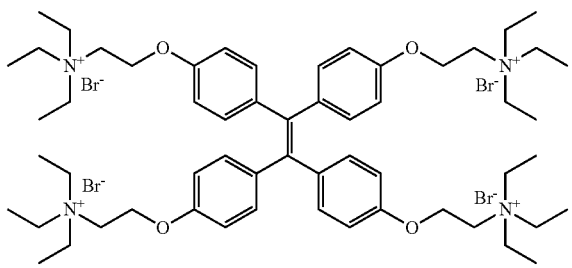

N+C2-TPE-C2N+

Characterization data of BrC2-TPE-C2Br: $^1$H NMR (300 MHz, CDCl$_3$), δ (ppm): 7.71-7.70 (m, 1H), 7.54-7.53 (m, 1H), 7.10-7.07 (d, 4H), 6.93-6.90 (d, 3H), 6.84-6.82 (d, 4H), 6.65-6.63 (d, 3H), 4.28-4.22 (m, 8H), 3.63-3.60 (m, 8H). $^{13}$C NMR (75 MHz, CDCl3), δ (ppm): 156.7, 132.8, 130.0, 115.0, 114.1, 68.0, 29.6. MS (TOF), m/e: 823.9 ([M]+, calcd. 824.2).

N+C2-TPE-C2N+: $^1$H NMR (400 MHz, D$_2$O), δ (ppm): 6.94-6.89 (m, 8H), 6.67-6.65 (m, 4H), 4.24-4.23 (m, 8H), 3.54-3.45 (m, 8H), 3.30-3.25 (m, 16H), 3.10-3.05 (m, 8H), 1.20-1.13 (m, 36H). $^{13}$C NMR (100 MHz, D$_2$O), δ (ppm): 156.2, 138.2, 133.1, 114.5, 98.0, 61.9, 56.0, 54.2, 54.1, 47.4, 9.1, 7.6. MS (FAB), m/e: 1222.5 ([M−2H]+, calcd. 1224.4).

Example 8

4,4'-(1,2-diphenylvinyl)di(phenylboronic acid) (TPE-BA)

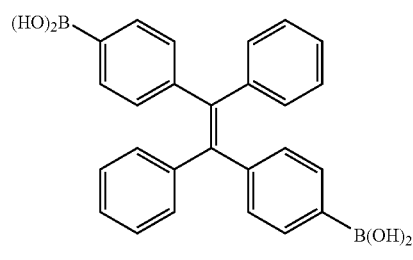

TPE-BA 1,2-bis(4-bromophenyl)-1,2-diphenylethene (0.4 g, 0.82 mmol) was dissolved in 20 ml of distilled tetrahydrofuran (THF) in a 100 ml flask, and the flask was placed in an acetone-dry ice bath at −78° C. A solution of 1.0 ml (2.6 mmol) of n-butyllithium (2.5 M in hexane) was added carefully to the mixture under stirring. After 1 h, 0.46 ml (4.0 mmol) of trimethyl borate was added to the solution and allowed to react for 45 min. The mixture was warmed to room temperature and overnight. Then dilute HCl was used to quench the reaction. After filtration and drying, the product was purified by silica gel column with ethyl acetate as eluent. The product was obtained as yellow solid in 54% yield.

Characterization data of TPE-BA: $^1$H NMR (d-MeOH, 300 MHz) δ (ppm): 7.26-7.17 (m, 10H), 7.01-6.94 (m, 4H), 6.73-6.65 (m, 4H); $^{13}$C NMR (d-MeOH, 75 MHz), 6(TMS, ppm):

157.2, 146.2, 141.4, 137.0, 133.9, 132.7, 128.9, 127.4, 115.7; MS (TOF) m/e: 422.2 ([M−2H]+ calcd: 420.1).

Example 9

4,4'-(1,2-diphenylvinyl)di(phenylcarboxylic acid) (TPE-CA)

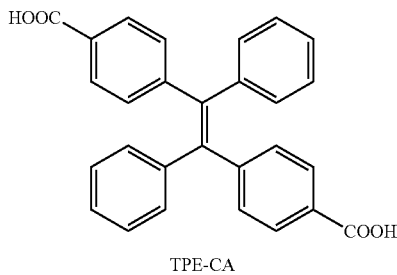

TPE-CA 1,2-bis(4-bromophenyl)-1,2-diphenylethene (1 g, 2.04 mmol) was dissolved in 20 ml of distilled tetrahydrofuran (THF) in a 100 ml flask, and the flask was placed in an acetone-dry ice bath at −78° C. A solution of 0.56 ml (6.12 mmol) of n-butyllithium (2.5 M in hexane) was added carefully to the mixture under stirring. The solution was transferred to a 500 ml flask with dry ice in it. The resultant mixture was stirred overnight under nitrogen at room temperature. After evaporation of THF, potassium hydroxide solution was added and the aqueous solution was washed by diethyl ether for several times. 3 M hydrochloric acid was used to acidify the aqueous solution. Ethyl acetate was used to extract the product. And the organic layer was dried with $MgSO_4$ to give the product with the yield of 24%.

Characterization data of TPE-CA: $^1$H NMR (d-Acetone, 300 MHz) δ(ppm): 7.99-7.93 (m, 3H), 7.50-7.46 (m, 1H), 7.35-7.28 (m, 9H), 7.25-7.16 (m, 4H), 7.15-7.10 (m, 1H); $^{13}$C NMR (d-Acetone, 75 MHz), δ (TMS, ppm): 166.1, 147.8, 142.4, 142.3, 141.1, 132.6, 130.7, 130.5, 128.8, 128.4, 127.6, 127.3, 126.7, 126.3, 120.0; MS (TOF) m/e: 403.14 ([M−OH]+ calcd: 403.14).

Example 10

1,2-di[4-(aminomethyl)phenyl]-1,2-diphenylethylene (TPE-MA)

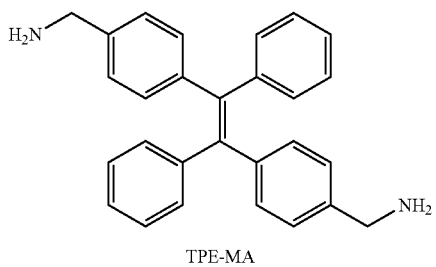

TPE-MA

A mixture of 1,2-diphenyl-1,2-dip-tolylethene (TPE-Me, 2 g, 5.6 mmol), NBS (2 g, 11.1 mmol) and a catalyst amount of benzoyl peroxide in carbon tetrachloride (50 ml) was gently refluxed for 8 h in a 150 ml round-bottom flask. After filtration and concentration, the product was isolated and purified by silica gel chromatography using chloroform/hexane (1:4 v/v) as eluent. 1,2-bis(4-(bromomethyl)phenyl)-1,2-diphenylethene (TPE-MB) was obtained as light yellow powder in 45% yield.

A mixture of TPE-MB (0.8 g, 1.5 mmol) and $NaN_3$ (0.1 g, 1.5 mmol) in DMSO (30 ml) was stirred under $N_2$ at room temperature for 18 h. The reaction mixture was added to water (200 ml) slowly, and then extracted with dichloromethane. The combined organic layers were dried with $MgSO_4$ and evaporated to dryness. The crude product was purified by silica gel chromatography eluting with 1:1 chloroform/hexane to give 1,2-bis(4-(azidomethyl)phenyl)-1,2-diphenylethene (TPE-MN3) as a white-off solid in 73% yield.

The azido-substituted TPE (TPE-MN3) (0.3 g, 0.7 mmol) was dissolved in dry THF (60 ml) and $LiAlH_4$ (0.15 g, 4.1 mmol) was added slowly at room temperature with constant stirring under nitrogen. Following the addition, the mixture was heated at reflux for 8 h. Water (5 ml-10 ml) was added slowly to decompose the excess $LiAlH_4$. The solution was then filtered and THF was used to wash the solid residue. After evaporation of the organic filtrate, dilute hydrochloric acid was added and the aqueous solution was washed by diethyl ether for several times. Ammonium hydroxide was used to basify the aqueous solution, following the extraction by diethyl ether. The organic layer was dried with $Na_2SO_4$ and evaporated to dryness. TPE-MA was obtained as light yellow powder in 87% yield.

Characterization data of TPE-MB: $^1$H NMR (CDCl$_3$, 300 MHz) δ (ppm): 7.14-7.07 (m, 10H), 7.02-6.96 (m, 8H), 4.42-4.40 (d, 4H); $^{13}$C NMR (CDCl$_3$, 75 MHz), δ (TMS, ppm): 144.4, 143.9, 141.5, 126.6, 132.3, 132.0, 129.2, 128.5, 127.4, 34.3; MS (TOF) m/e: 518.0 ([M]+ calcd: 518.2).

TPE-MN3: $^1$H NMR (CDCl$_3$, 300 MHz) δ(ppm): 7.12-7.07 (m, 6H), 7.04-6.99 (m, 12H), 4.24 (s, 4H); $^{13}$C NMR (CDCl$_3$, 75 MHz), δ (TMS, ppm): 144.4, 143.9, 141.5, 134.1, 132.4, 131.9, 128.5, 128.4, 127.3, 55.2; MS (TOF) m/e: 400.15 ([M−3N]+ calcd: 400.14)

TPE-MA: $^1$H NMR (d-MeOH, 300 MHz) δ (ppm): 7.10-7.06 (m, 10H), 7.00-6.93 (m, 8H), 3.75-3.70 (br, 4H); $^{13}$C NMR (CDCl$_3$, 75 MHz), δ (TMS, ppm): 143.9, 142.4, 140.7, 131.6, 131.4, 127.8, 127.7, 126.5, 126.4, 30.4; MS (TOF) m/e: 374.1 ([M−NH$_2$]+ calcd: 374.2)

Example 11

1,1'-Bis-[4-(N,N'-diethylaminomethyl)phenyl]-2,3,4,5-tetraphenylsilole (A$_2$-HPS) and N,N'-[1,1'-bis(1,4-benzylene)-2,3,4,5-tetraphenylsilolyl)bis(triethylammonium bromide) (HPS-(ClN+)2

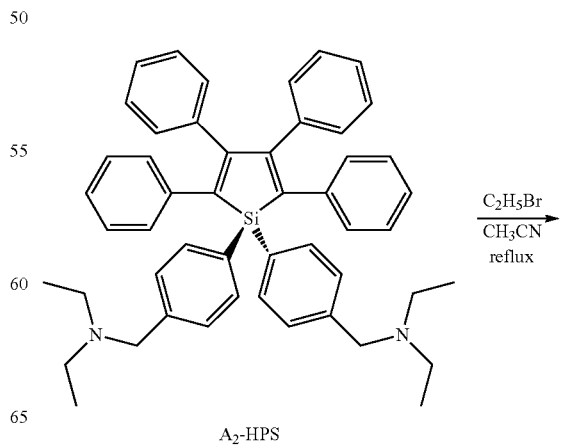

A$_2$-HPS

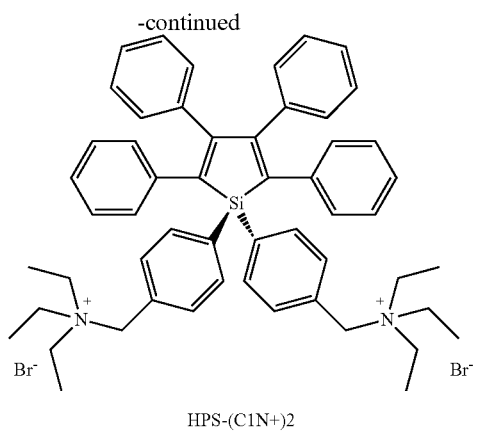

HPS-(C1N+)2

Into a 500 ml round-bottomed flask were added 150 ml THF, 5 ml water, 2.2 g potassium carbonate, 6 ml diethyl amine, and 5 g p-bromobenzyl bromide. The resultant mixture was refluxed for 12 h. The mixture was then cooled to room temperature, into which 6 ml concentrated HCl was added, followed by the addition of 150 ml water. The mixture was extracted with 100 ml diethyl ether for three times. The diethyl ether solution was dried with anhydrous magnesium sulfate over night and then the magnesium sulfate was removed by filtration. Diethyl ether was evaporated and the raw product was purified by a silica gel column using hexane/chloroform mixture (1:1 by volume) as the eluent. (p-bromobenzyl)diethyl amine (BBDA) was obtained in 74% yield (3.6 g).

Into a solution of tolan (5 g, 28 mmol) in THF (25 ml) was added under dry nitrogen lithium shaving (0.214 mg, 31 mmol). The mixture was stirred for 12 h at room temperature and the resultant green-blue colored THF solution was added dropwise to a solution of tetrachlorosilane (1.61 ml, 14 mmol) in 125 ml THF. The reaction mixture was stirred for 2 h at room temperature and then refluxed for 5 h.

Into another flask were added BBDA (6.8 g, 28 mmol) and 80 ml THF. The mixture was cooled to −78° C., into which 10 ml n-BuLi (2.5 M in hexane) was added. After stirring for 1.5 h, the mixture was transferred dropwise at −78° C. to the solution of chlorosilole (preparation shown in previous patent). The reaction mixture was allowed to warm to room temperature and was then stirred overnight at that temperature. Then THF was removed by evaporation, and the crude product was dissolved in diethyl ether. The solution was washed three times by water. The crude product was purified by a silica gel column using chloroform as the eluent at first and changed to ethyl acetate when no by product came out. The product $A_2$-HPS was obtained in 28% yield after recrystallization from actone/ethanol mixture.

Characterization data of BBDA: $^1$H NMR (CDCl$_3$, 300 MHz) δ (ppm): 7.40 (d, 2H), 7.23 (d, 2H), 3.51 (s, 2H), 2.50 (m, 4H), 1.04 (m, 6H).

$A_2$-HPS: $^1$H NMR (CDCl$_3$, 300 MHz) δ (ppm): 7.56 (d, 2H), 7.32 (d, 2H), 7.05-6.75 (m, br, 20H), 3.55 (s, 4H), 2.54 (m, 8H), 1.04 (m, 12H). $^{13}$C NMR (75 MHz, CDCl$_3$), δ (TMS, ppm): 156.6, 142.3, 140.0, 139.9, 139.0, 136.2, 130.2, 129.8, 129.0, 127.9, 127.6, 126.5, 125.7, 57.8, 47.2, 12.1. MS (CI): m/e calcd for $C_{50}H_{52}N_2Si$, 708.4, found 709.4 (M$^+$). UV (THF, 4.0×10$^{-5}$ mol/L), $\lambda_{max}$ (nm): 364. Melting point: 119-120° C.

HPS-(C1N+)2 was obtained by refluxing $A_2$-HPS together with bromoethane in acetonitrile.

Example 12

Fluorimetric titration of biomacromolecules to polyenes Bovine serum albumin (BSA) and calf thymus DNA (ctDNA) were selected as model proteins and DNA. BSA was dissolved in a pH 7.0 phosphate buffer solution (1.0 mg/ml). DNA was dissolved in deionized water (1.0 mg/ml) and filtered through a 0.45 μm filter. The actual concentration (in nucleic base) was determined by UV photometry using the extinction coefficient $\epsilon_{260}$=6600 M$^{-1}$ cm$^{-1}$.

Stock solutions of polyenes were 5×10$^{-4}$ M in water. Fluorescence titration was carried out by sequentially adding 100 μl aliquots of DNA or BSA solutions to a 100 μl stock solution of polyenes, followed by adding an aqueous phosphate buffer (10 mM, pH 7) to acquire a 10.00 ml solution. The mixtures were stirred for half an hour prior to taking their spectra. See FIGS. 1-10 and Table 1 below.

TABLE 1

Photophysical Properties of TPEs in Solution (soln),[a] Aggregate (aggr),[b] and Binding (bind)[c] States

| TPE | $\lambda_{ab}$, nm[d] | | $\lambda_{em}$, nm ($\Phi_F$, %)[e] | | |
|---|---|---|---|---|---|
| | soln | aggr | soln | aggr | bind |
| TPE-OMe | 311 | 330 | 394 (0.11) | 477 (15.30) | |
| TPE-OH | 312 | 316 | 393 (0.57) | 439 (8.90) | 467 (35.7) |
| TPE-SO3 | 312 | 320 | 398 (0.37) | 442 (17.47) | 472 (58.2) |

[a]In acetonitrile for TPE-OMe and TPE-OH (10 μM); in water for TPE-SO3 (5 μM).
[b]In 99% water/AN mixture for TPE-OMe and TPE-OH; in 99% AN/water mixture for TPE-SO3.
[c]In BSA solution of TPE-OH•Na$_2$ or TPE-SO3 in an aqueous phosphate buffer with pH = 7.0.
[d]Absorption maximum.
[e]Emission maximum (quantum yield given in the parentheses); excitation wavelength: 350 nm.

Example 13

Comparison of Water Soluble and Non-Water Soluble Tetraphenylethylene Derivatives In this example, a group of AIE-active tetraphenylethylene (TPE) derivatives, i.e., derivatives 1-4 below, were synthesized and water-soluble cationic salts 3 and 4 were evaluated for their utility as bioprobes. In aqueous buffer solutions, these non-emissive fluorophores become highly emissive upon binding to protein and DNA molecules through noncovalent, such as hydrophobic and electrostatic, interactions.

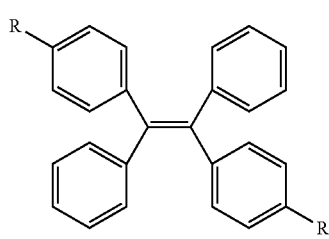

Derivative 1: R is —O(CH$_2$)$_2$Br
Derivative 2: R is —O(CH$_2$)$_4$Br
Derivative 3: R is —O(CH$_2$)$_2$N$^+$(C$_2$H$_5$)$_3$Br$^-$
Derivative 4: R is —O(CH$_2$)$_4$N$^+$(C$_2$H$_5$)$_3$Br$^-$ The TPE derivatives were prepared by the synthetic route as described herein. Reactions of 1,2-bis(4-hydroxyphenyl)-1,2-diphenylethene with α,ω-dibromoalkanes in the presence of sodium hydride yielded TPEs 1 and 2, whose quaternizations by NEt$_3$ gave salts 3 and 4, respectively. Molecular structures of the TPEs were characterized by spectroscopic techniques, from which satisfactory analysis data were obtained. Dyes 1 and 2 are soluble in common organic solvents such as acetonitrile (AN), chloroform and THF but insoluble in water. Salts 3 and 4, on the other hand, are soluble in water as well as in DMF and DMSO.

Figure 11A:
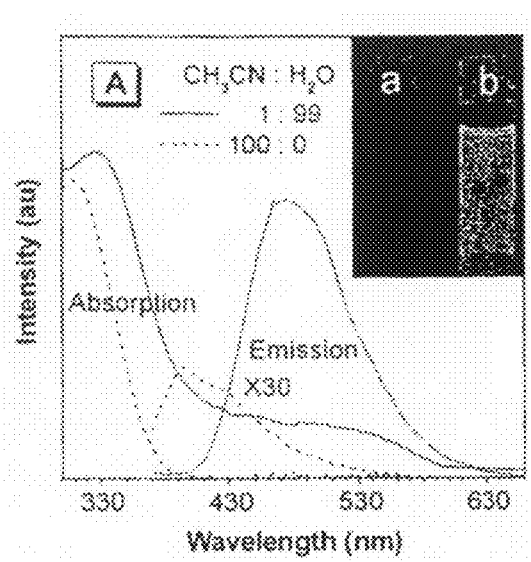
FIG. 11A illustrates the absorption and emission spectra of solutions of derivative 1 (10 μM) in AN and AN-water mixture (1:99 v/v). The inset is photographs of solutions of derivative 1 in (a) AN and (b) the AN-water mixture taken under illumination of a UV lamp.

Dilute solutions of TPEs 1 and 2 in AN are practically non-luminescent. Addition of non-solvent water into the AN solutions can turn on the emissions of the dyes. From the molecular solution in AN to the aggregate suspension in an AN-water mixture (1:99 by volume), the fluorescent intensity of TPE 1 at 476 nm is increased by ~240 fold (FIG. 11A). Its absorption maximum shifts from 310 nm in the solution to 330 nm in the suspension. The excitation maximum of TPE 1 locates at 330 nm, coinciding well with its absorption maximum. The formation of nanoscopic aggregates of TPE 1 is suggested by the level-off tail in the visible region of its absorption spectrum due to the Mie effect of the nanoparticles. Evidently, the emission of TPE 1 is induced by the aggregate formation, or in other words, TPE 1 is AIE-active.

Figure 11B:
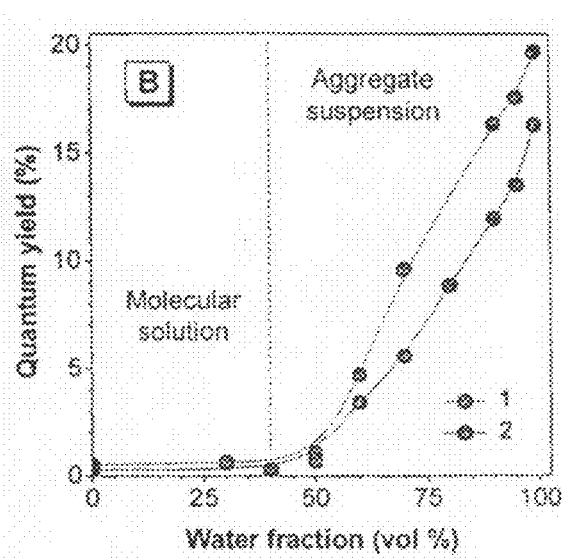
FIG. 11B illustrates the dependence of fluorescence quantum yields of solutions of derivatives 1 and 2 on the solvent composition of AN-water mixture $\lambda_{ex}$=350 nm.

The change of $Ø_F$ value of TPE 1 with water fraction in the AN-water mixture further reveals its AIE characteristics (FIG. 11B). In the mixtures with water fractions below ~40%, TPE 1 exhibits negligibly small OF values (~0.5%) because the dye molecules are actually dissolved in the mixtures. The $Ø_F$ value of TPE 1 starts to increase when the water fraction is increased to ~50%, at which the solvating power of the mixture is decreased to such an extent that the dye molecules begin to aggregate. The $Ø_F$ value reaches 20% at a water content of 99%, which is ~40-fold higher than that of its AN solution. The absolute $Ø_F$ values of the aggregates should be much higher than the relative $Ø_F$ values given in FIG. 11B, because the determination of the latter did not take into consideration the strong absorption caused by the Mie effect of the aggregates. TPE 2 exhibits similar AIE behavior. TPE Salts 3 and 4 are soluble in water. Addition of methanol, AN, THF and dioxane to their water solutions do not cause the salts to aggregate, possibly due to their amphiphilic nature. Their emissions in the mixtures remain as faint as those in the water solutions. However, increasing the concentrations of the salts can increase their $Ø_F$ values, indicating that the salts are also AIE-active.

Complexation of the water-soluble AIE TPEs 3 and 4 with calf thymus DNA (ctDNA) and bovine serum albumin (BSA) were investigated by spectrometric titrations in aqueous phosphate buffer (pH=7.0) at 25° C. Stock solutions of TPEs 3 and 4 (0.25 mM) were prepared. The mixture of 100 µl stock solution of 3 with 9.9 ml buffer emits faintly at 395 nm with a side band at 462 nm. Its absorption maximum locates at 311 nm, with a molar absorptivity of 12400M$^{-1}$ cm$^{-1}$. Upon addition of the DNA, FL intensity of TPE 3 increased by 5.4 fold. Meanwhile its emission maximum shifted to ~462 nm, giving a Stokes shift as large as 134 nm. In the DNA concentration range of 0-100 µg/ml$^{-1}$, the plot of the FL intensity (I) at 462 nm as a function of DNA concentration (c) is a linear line with a correlation coefficient of 0.996. Addition of BSA to a buffer solution of TPE 3 induced a similar effect. The linear range of the I/I$_o$–1 vs. c plot in this case is 0-50 µg/ml$^{-1}$. The excitation maximums of the solutions of TPE 3 containing BSA and ctDNA both locate at 328 mm.

The effects of the biopolymers on the FL properties of TPE 4 are much more pronounced. As can be seen from FIG. 12, I/I$_o$ values as high as 16.3 and 23.8 are achieved when 300 µg/ml$^{-1}$ ct DNA and 500 µg/ml$^{-1}$ BSA are added into solutions of TPE 4, respectively. Clearly TPE 4 is a more sensitive bioprobe. The excitation maximum of TPE 4 is at 328 nm and the Stokes shift is ~135 nm. The linear ranges of TPE 4 are narrower: 0-20 µg/ml$^{-1}$ for DNA and 0-40 µg/ml$^{-1}$ for BSA. It is clear that the AIE salts TPEs 3 and 4 can be used as light-up bioprobes for DNA and protein detection. The probing sensitivity and linear range can be tuned by modifying their structures.

Regarding the origin of the emission induced by the addition of the biomacromolecules, the correlation with the AIE nature of the dyes must be considered. In both cases, similar shifts in the fluorescent maximums (from 390-399 nm to 463-478 nm) are observed. The excitation spectra of the biopolymer-induced emissions are also similar to those of the AIEs for the TPE derivatives. These facts lead to a natural conclusion that the strong blue emissions are from the same excited species.

It appears that the restriction of intramolecular rotations in the aggregates of AIE dyes may have blocked their nonradiative channels, thus making them highly emissive. If the AIE process of the TPE dyes follows the same mechanism, they should become emissive in the solutions with high viscosities at low temperatures, because under these conditions their intramolecular rotations would be hampered. The fluorescent behaviors of TPE 4 were thus investigated in a highly viscous glycerol-water (99:1 by volume) mixture at different temperatures. At 25° C., the glycerol-water solution of TPE 4 emits a strong blue light of 467 nm with a Stokes shift of 147 nm (FIG. 13), demonstrating that the high viscosity indeed helps. As the solution temperature is decreased from 25 to ~5° C., the FL intensity of TPE 4 is increased as expected. Its excitation maximum locates at 328 nm, close to those of its nanoscopic aggregates and its complexes with the biopolymers.

It is well known that fast conformational exchanges caused by fast intramolecular rotations give sharp NMR resonance peaks, which can be broadened by cooling because the rotations and hence the exchanges become slower at lower temperatures. Dynamic NMR experiments of a dichloromethane solution of 1 reveals that its resonance peaks are broadened with a decrease in temperature. The plot of $\delta_{fwhm}$ vs. 1/T gives a linear line, indicating a single mechanism for the peak broadening. All these results confirm that the restriction of intramolecular rotations plays a crucial role in the AIE process. We now may envision how the emissions of the TPE salts are turned on by the addition of the biomacromolecules. In the buffer solutions containing the DNA and BSA, the cationic amphiphilic dyes bind to the biomacromolecules via noncovalent interactions, such as electrostatic attraction (especially for the negative-charged DNA) and hydrophobic effect (particularly for the protein with hydrophobic pockets in its native folding structure). When docked on the surfaces of the biopolymers and in the cavities of their folding structures, the dye molecules aggregate with the aid of strong electronic and hydrophobic interactions between their aryl rings. This suppresses intramolecular rotations of the dye molecules, which in turn impedes their radiationless transitions and activates their fluorescent processes. Thanks to the AIE nature, the emissions of the TPE-biopolymer complexes are greatly intensified with increasing concentration, for the TPE 4-BSA complex. This is truly remarkable, because conventional fluorescent probes suffer from the ACQ problem at high dye concentrations. In summary, in this example, we have successfully developed AIE active, water-soluble, conjugated polyene compounds (cationic dyes) for protein and DNA detection in aqueous media for the first time. The nonemissive dye solutions become emissive upon addition of the biomacromolecule, for example, DNA and/or BSA. These AIE compounds exhibit large molar absorptivities, high quantum yields and wide Stokes shifts and are thus ideal "turn-on" fluorescent bioprobes. The restriction of their intramolecular rotations plays a critical role in their AIE processes. Accordingly, any molecule whose electronic conjugation is affected by the twisting of multiple pendants around its core due to involved steric effects can be AIE active. This example demonstrates that AIE luminophors can be utilized as fluorescent probes in the area of biological research.

Example 14

Synthesis of 4,4'-(1,2-diphenylvinyl)di(phenylcarboxylic acid) (TPE-COOH)

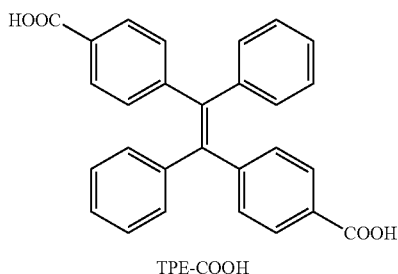

TPE-COOH

The scheme of the synthesis of TPE-COOH is shown in Scheme 1 above. 1,2-bis(4-bromophenyl)-1,2-diphenylethene (1 g, 2.04 mmol) was dissolved in 20 ml of distilled tetrahydrofuran (THF) in a 100 ml flask, and the flask was placed in an acetone/dry ice bath at −78° C. A solution of 0.56 ml (6.12 mmol) of n-butyllithium (2.5 M in hexane) was added carefully to the mixture under stirring. The solution was transferred to a 500 ml flask with dry ice in it. The resultant mixture was stirred overnight under nitrogen at room temperature. After evaporation of THF, potassium hydroxide solution was added and the aqueous solution was washed by diethyl ether for several times. 3 M hydrochloric acid was used to acidify the aqueous solution. Ethyl acetate was used to extract the product. And the organic layer was dried with $MgSO_4$ to give the product with the yield of 24%.

Characterization data of TPE-COOH: $^1$H NMR (d-Acetone, 300 MHz) δ (ppm): 7.99-7.93 (m, 3H), 7.50-7.46 (m, 1H), 7.35-7.28 (m, 9H), 7.25-7.16 (m, 4H), 7.15-7.10 (m, 1H); $^{13}$C NMR (d-Acetone, 75 MHz), δ (TMS, ppm): 166.1, 147.8, 142.4, 142.3, 141.1, 132.6, 130.7, 130.5, 128.8, 128.4, 127.6, 127.3, 126.7, 126.3, 120.0; MS (TOF) m/e: 403.14 ([M−OH]$^+$ calcd: 403.14).

Figure 14:
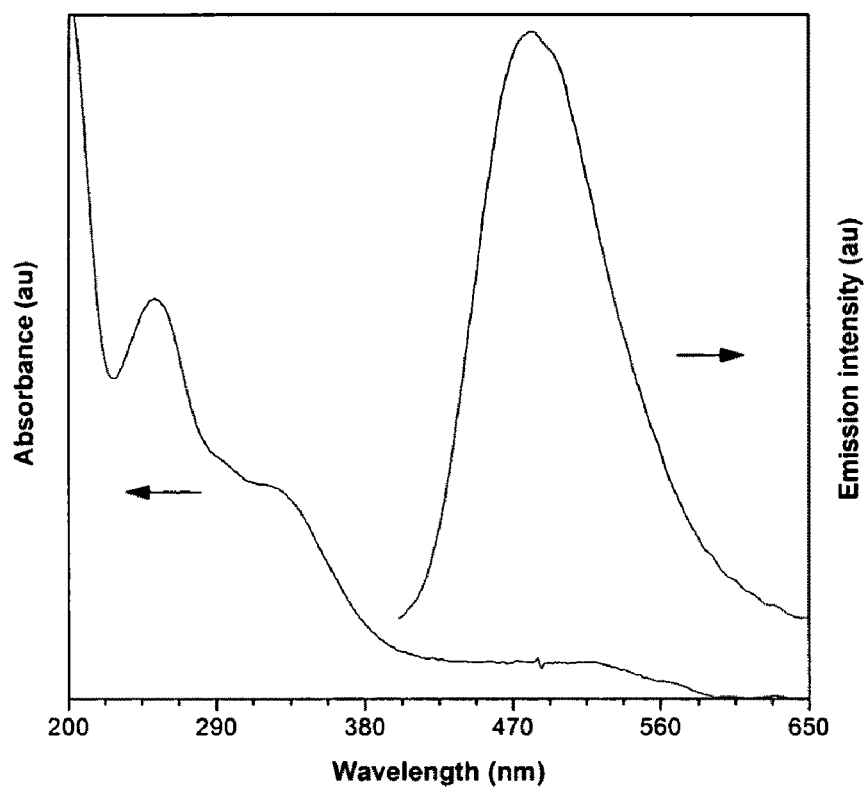
FIG. 14 illustrates the absorption and photoluminescence spectra of TPE-COOH in acetonitrile/water mixture (1:99 v/v). TPE-COOH concentration: 10 μM; excitation wavelength: 346 nm.

The absorption and photoluminescence spectra of the dye in acetonitrile/water:mixture (1:99 v/v) are shown in FIG. 14. When it is molecularly dissolved in acetonitrile, it is practically nonfluorescent. However, when large amount of water (insoluble to TPE-COOH yet miscible with acetonitrile) is added, bright cyan light (~480 nm) is observed. The emission becomes stronger with an increase in water content, suggesting that TPE-COOH is AIE-active.

Example 15

Synthesis of 1,2-Bis(4-hydroxyphenyl)-1,2-diphenylethylene (TPE-OH)

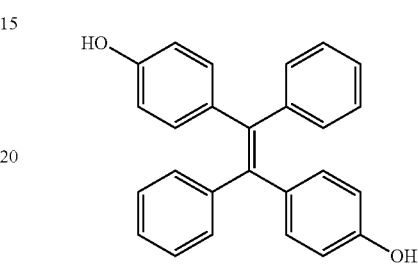

TPE-OH

A suspension of p-methoxybenzophenone (1.06 g, 5.0 mmol), 1.34 equiv of $TiCl_3/AlCl_3$ (5.81 g, 6.7 mmol), and 25 equiv of Zn dust (8.01 g, 122.0 mmol) in 100 ml of dry THF was refluxed for 20 h. The reaction mixture was cooled to room temperature and filtered. The filtrates were evaporated and the crude product was purified by a silica gel column using hexane as eluent. 1,2-Bis(4-methoxyphenyl)-1,2-diphenylethene (TPE-OMe) was isolated in 91% yield.

TPE-OMe (1.40 g, 3.56 mmol) was dissolved in 20 ml of dichloromethane (DCM) in a 100 ml flask, and the flask was placed in an acetone-dry ice bath at −78° C. A solution of 3.59 g (14.3 mmol) of boron tribromide in 10 ml of DCM was added carefully to the mixture under stirring. The resultant mixture was allowed to warm to room temperature overnight under stirring. The reaction product was hydrolyzed by careful shaking with 20 ml of water. The organic phase was separated and concentrated by a rotary evaporator. The crude product was purified by recrystallization from THF/methanol to afford a white solid in 97% yield.

Characterization data of TPE-OMe: $^1$H NMR (CDCl$_3$, 300 MHz) δ (ppm): 7.10-7.06 (m, 10H), 6.93 (t, 4H), 6.64 (t, 4H), 3.74 (s, 6H). $^{13}$C NMR (CDCl$_3$, 75 MHz) δ (ppm): 158.0, 144.4, 139.7, 136.5, 132.6, 131.5, 127.8, 126.3, 113.2, 55.2. MS (TOF) m/e: 392.1 (M$^+$, calcd. 392.2).

Characterization data of TPE-OH: $^1$H NMR (CDCl$_3$, 300 MHz) δ (ppm): 7.11-7.02 (m, 10H), 6.88 (t, 4H), 6.56 (d, 4H). $^{13}$C NMR (CDCl$_3$, 75 MHz) δ (ppm): 154.1, 144.2, 139.7, 135.5, 132.8, 131.5, 127.8, 126.3, 114.7. MS (TOF) m/e: 363.1 [(M−H)$^+$, calcd: 363.1].

Example 16

N,N',N'',N'''-[1,2-Tetrakis(1,4-phenoxyethyl)vinyl] tetrakis(triethylammonium bromide) (N+C2-TPE-C2N+)

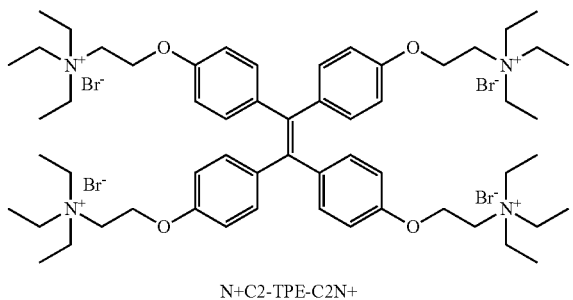

N+C2-TPE-C2N+

THF (Labscan) was purified by distillation from sodium benzophenone ketyl under nitrogen immediately prior to use. DHBP, titanium(IV) chloride, zinc dust, 1,2-dibromoethane, potassium carbonate, acetone, triethylamine, and other reagents were all purchased from Aldrich and used as received.

$^1$H and $^{13}$C NMR spectra were measured on a Bruker ARX 300 spectrometer with tetramethylsilane (TMS; δ=0) as the internal standard. Mass spectra were recorded on a Finnigan TSQ 7000 triple quadrupole spectrometer operating in a MALDI-TOF mode. UV spectra were measured on a Milton Roy Spectronic 3000 Array spectrophotometer and FL spectra were recorded on a Perkin-Elmer LS 55 spectrofluorometer with a Xenon discharge lamp excitation. Time-dependent FL signals were measured using a FluostarOptima multifunctional microplate reader (BMG Labtechnologies) with excitation/emission wavelengths set at 350/470 nm. CD spectra were recorded on a Jasco J-810 spectropolarimeter in 1 mm quartz cuvette using a step resolution of 0.2 nm, a scan speed of 100 nm/min, a sensitivity of 0.1°, and a response time of 0.5 s. Each spectrum was the average of three scans.

The synthetic route to TTAPE is shown in FIG. 49. McMurry coupling of BBEBP yields TBEPE, quaternization of which by triethylamine generates TTAPE. Detailed experimental procedures for the dye synthesis are given below.

To a mixture of DHBP (3.0 g, 14.0 mmol) and potassium carbonate (5.0 g, 36.2 mmol) in acetone (50 mL) was added 1,2-dibromoethane (4 mL, 46.4 mmol). The mixture was refluxed under stirring for 24 h. After filtration and solvent evaporation, the crude product was purified by a silica gel column using chloroform as eluent. BBEBP was obtained as white powder in 70% yield (4.20 g). $R_f$=0.6 (chloroform); $^1$H NMR (300 MHz, CDCl$_3$, 25° C., TMS): δ=3.68 (t, 4H; BrCH$_2$), 4.38 (t, 4H; OCH$_2$), 6.97 (d, 4H, J☐9.0 Hz; Ar), 7.78 ppm (d, 4H, J=9.0 Hz; Ar); $^{13}$C NMR (75 MHz, CDCl$_3$, 25° C., TMS): δ=29.3, 68.6, 114.8, 115.8, 131.9, 133.0, 162.0 ppm.

In a suspension of BBEBP (1.0 g, 2.3 mmol) in 50 mL of THF were added TiCl$_4$ (0.26 mL, 2.3 mmol) and Zn dust (0.31 g, 4.6 mmol). After refluxing for 20 h, the reaction mixture was cooled to room temperature and filtered. The solvent was evaporated under vacuum and the crude product was purified by a silica gel column using a chloroform/hexane (1:4 v/v) mixture as eluent. TBEPE was obtained as white solid in 63% yield (6.606 g). $R_f$=0.7 (chloroform/hexane=1:4); $^1$H NMR (300 MHz, CDCl$_3$, 25° C., TMS): δ=3.63 (t, 8H; BrCH$_2$), 4.23 (t, 8H; OCH$_2$), 6.66 (d, 8H, J=8.7 Hz; Ar), 6.93 ppm (d, 4H, J=8.7 Hz; Ar); $^{13}$C NMR (75 MHz, CDCl$_3$, 25° C., TMS): δ=29.8, 68.3, 114.5, 133.3, 138.0, 139.1, 157.0 ppm; MALDI-TOF-MS m/z: calcd for $C_{34}H_{32}Br_4O_4^+$: 823.8993; found 823.8688 ([M]$^+$).

In a 250 mL flask with a magnetic stirrer was dissolved TBEPE (100 mg, 0.12 mmol) in THF (100 mL). After adding an excess amount of triethylamine (5 mL, 35.6 mmol), the solution was refluxed for 3 days. During the period, 10 mL of water was added at several intervals. The organic solvents were evaporated under reduced pressure and the aqueous solution was washed with chloroform three times. After solvent evaporation and drying overnight in vacuo at 50° C., TTAPE was isolated as yellow viscous liquid in 56% yield (0.089 g). $^1$H NMR (400 MHz, D$_2$O, 25° C., TMS): δ=1.13-1.20 (m, 36H; NCH$_2$CH$_3$), 3.25-3.30 (m, 24H; NCH$_2$CH$_3$), 3.45-3.54 (m, 8H; OCH$_2$CH$_2$N), 4.23-4.24 (m, 8H; OCH$_2$CH$_2$N), 6.65-6.67 (m, 8H; Ar), 6.89-6.94 ppm (m, 8H; Ar); $^{13}$C NMR (75 MHz, D$_2$O, 25° C., TMS): δ=7.4, 47.2, 54.2, 61.8, 114.5, 133.0, 138.0, 139.5, 156.2 ppm; MALDI-TOF-MS m/z: calcd for $C_{58}H_{92}Br_4N_4O_4^+$ [M–2Br]$^+$: 1066.5485; found 1066.5359 ([M–2Br]$^+$).

Example 17

Preparation of Fluorescent Polymer Particles

Into a 50 ml dropping funnel was dissolved 0.1 wt % TPE-COOH in a monomer mixture of methyl methacrylate, butyl acrylate and 2-hydroxyethyl methacrylate, with the volume ratio of 4:5:1. The solution was purged with nitrogen for 20 min and then added dropwise into the deionized water containing the emulsifier sodium dodecyl sulfate (0.2 wt %). The emulsion copolymerization proceeds at 75° C. under 400 rpm agitation for 6-10 h then stops by cooling.

Figure 15:
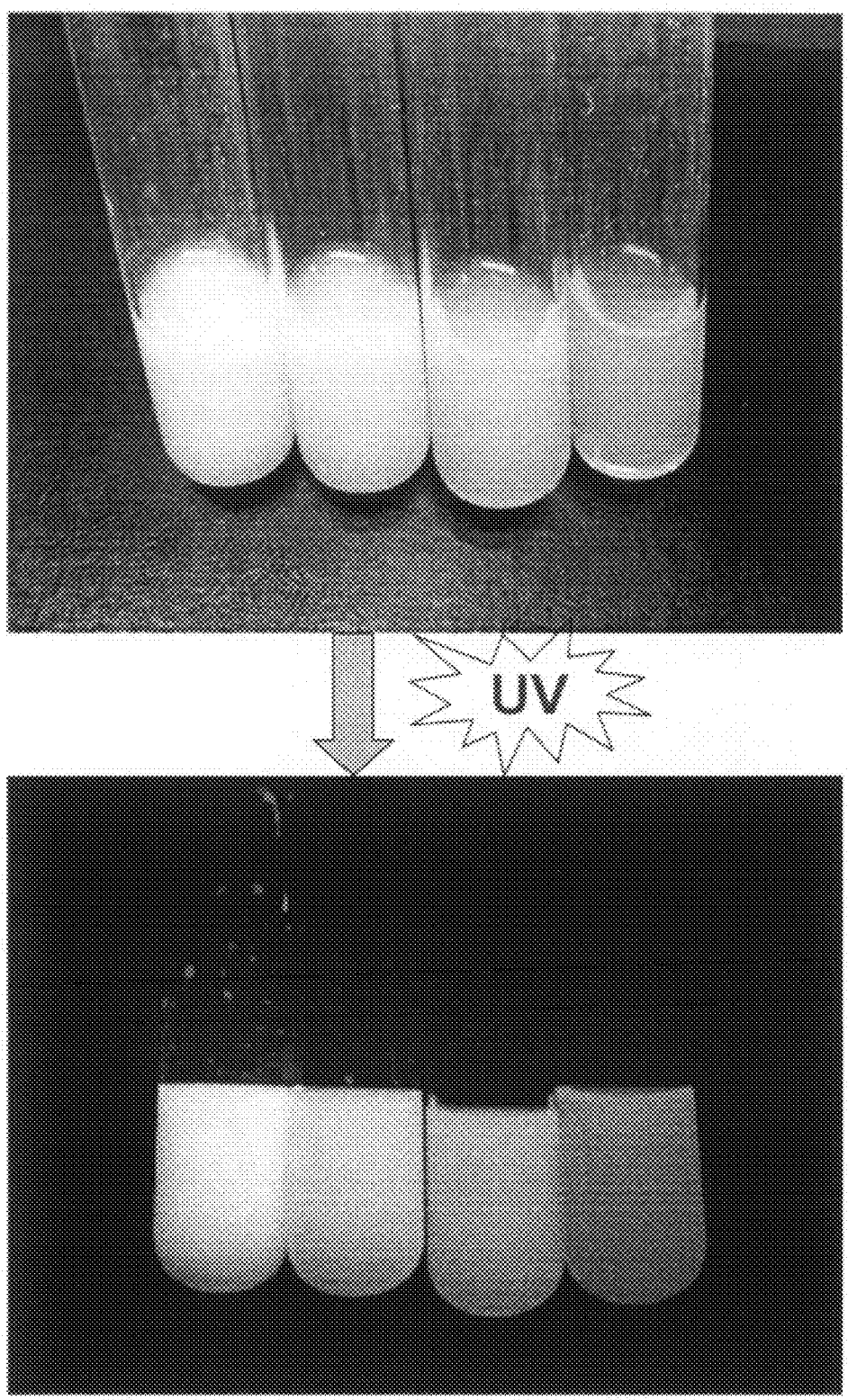
FIG. 15 illustrates the light emission of the fluorescent polymer particle dispersion of Example 17 with various dilutions: 100%, 20%, 5%, 1% (from left to right).

The polymer particle dispersion prepared is quite uniform and stable. The particle dispersion is highly emissive under UV irradiation, even in very dilute state (FIG. 15). It is worthy of noting that the emission of emulsion does not fade even when it is stored for several months under ambient temperature without any protection from light and air. This is due to the high stability of TPE molecules, which is distinctly different from other dye molecules that are prone to be bleached under room illumination.

Example 18

Preparation of Fluorescent Polymer Particles

The procedures are just the same as that in Example 17, except that the ratio of TPE-COOH decreases to 0.05 wt % relative to the monomer mixture of methyl methacrylate, butyl acrylate and 2-hydroxyethyl methacrylate (4:5:1 in volume).

Figure 16:
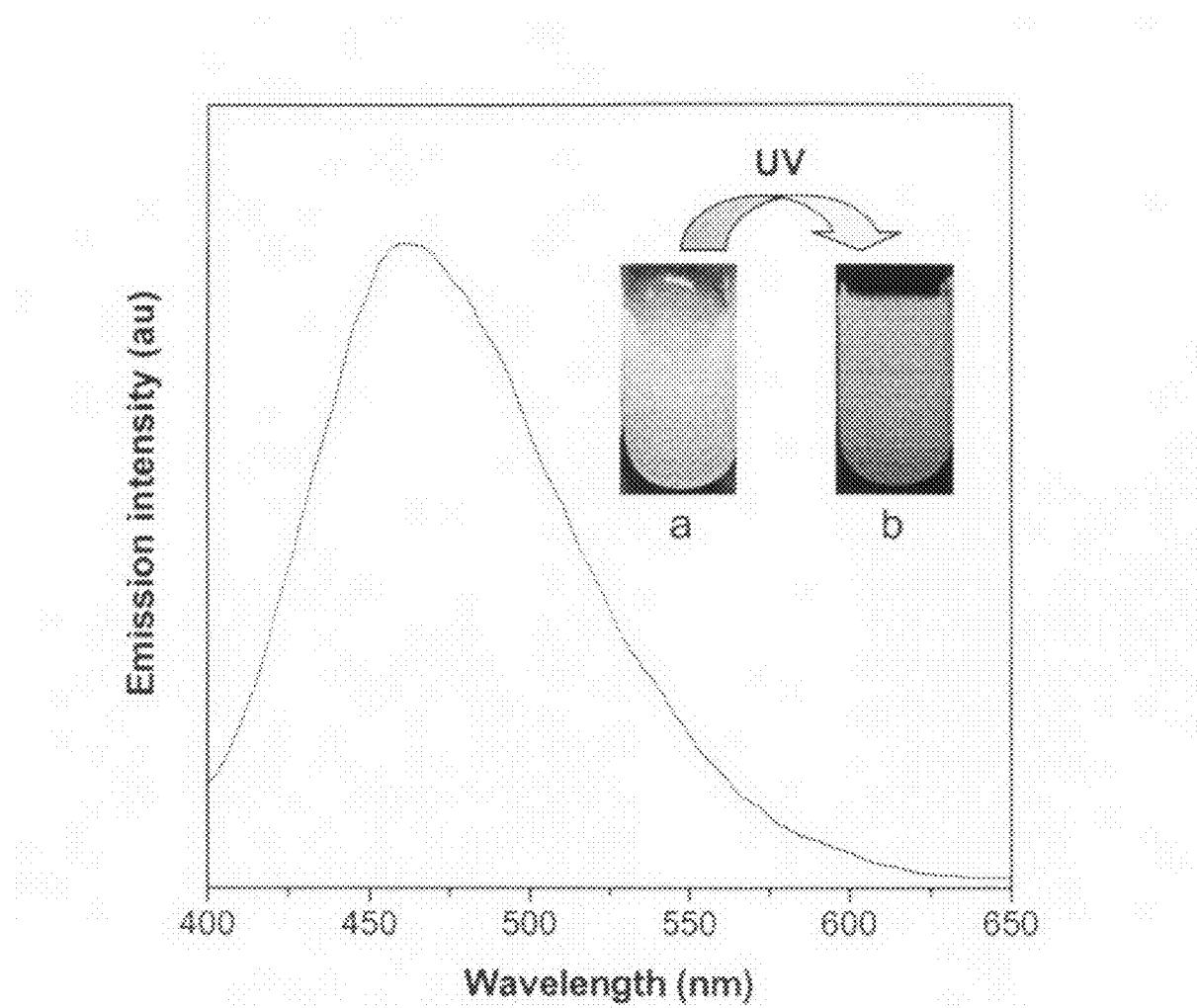
FIG. 16A illustrates the photoluminescence spectrum of the polymer particle dispersion of Example 18 containing TPE-COOH fluorophores. Concentration of the polymer in emulsion: 0.5 wt %; ratio of TPE-COOH to polymer: 0.1%; excitation wavelength: 346 nm.
FIG. 16B illustrates photographs of the polymer nanoparticle emulsion of Example 18 under normal room illumination (a) and 365 nm irradiation from a UV lamp (b).
Figure 17:
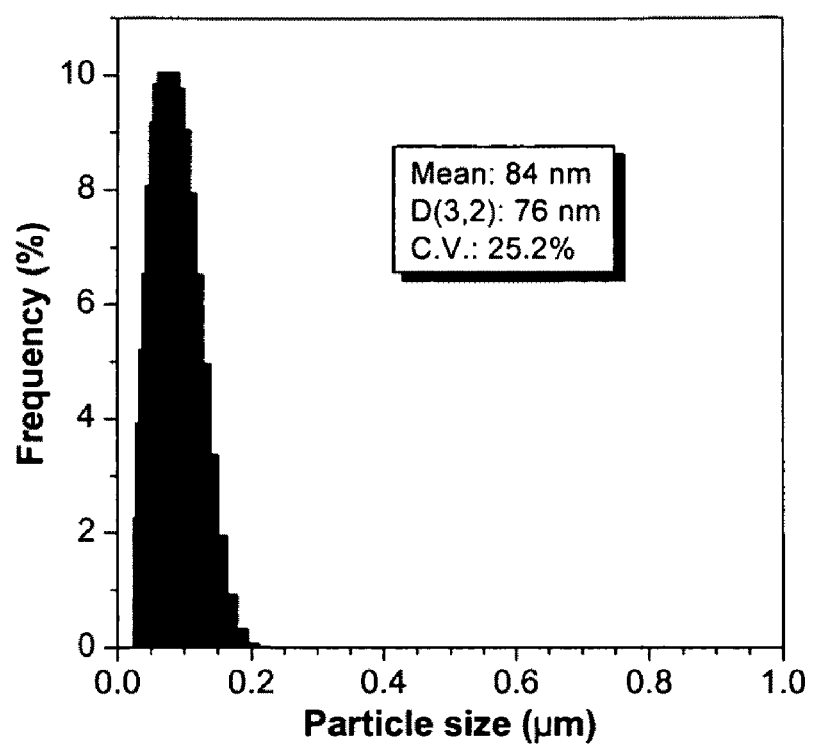
FIG. 17 illustrates the particle size and size distribution of the fluorescent polymer particles of Example 19. The inset shows the number-average diameter (Mean), weight-average diameter (D(3,2)), and coefficient of variation (C.V.) for the particles.

The polymer particle dispersion prepared is quite uniform and stable. The particle dispersion is highly emissive under UV irradiation, even in very dilute state. The photoluminescence spectrum of the dispersion is shown in FIG. 16. The emission peak is found at 458 nm, which is somewhat blue shifted compared to the pure TPE-COOH.

Example 19

Preparation of Fluorescent Polymer Particles

The procedures are just the same as that in Example 18, except that the ratio of methyl methacrylate, butyl acrylate and 2-hydroxyethyl methacrylate changes to 5:4:1 in volume.

The polymer particle dispersion prepared is quite uniform and stable. The particle dispersion is highly emissive under UV irradiation, even in very dilute state. The particle size distribution of the polymer nanoparticles in the emulsion was shown in FIG. 18. The diameter of the polymer nanoparticles is on the average of 80 nm, and the size distribution is narrow.

Example 20

Preparation of Fluorescent Polymer Particle

The procedures are just the same as that in Example 18, except that the emulsifier concentration decreases to 0, that is, the emulsion polymerization proceeds in the absence of emulsifier.

Figure 18A:
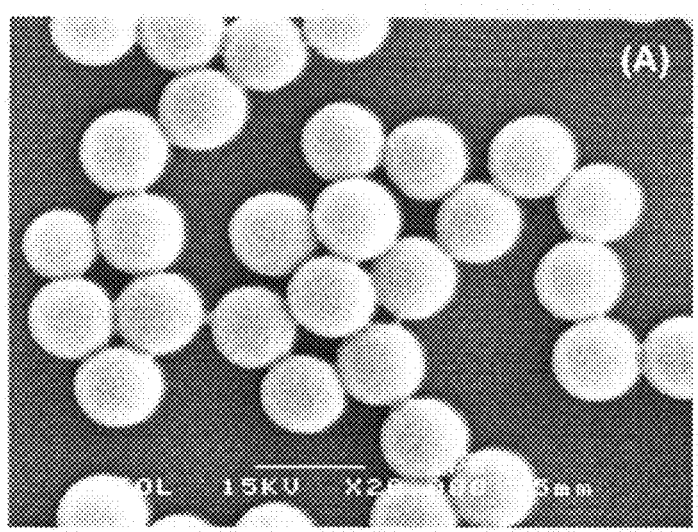
FIG. 18A is a scanning electron micrograph image of the fluorescent polymer particles of Example 20 prepared at a surfactant concentration of 0.

The polymer particle dispersion prepared is quite uniform. The particles tend to precipitate, however, they are readily be redispersed upon agitation. The particle dispersion is highly emissive under UV irradiation, even in very dilute state. The SEM image of the fluorescent polymer particles are shown in FIG. 18A, indicating a 760 nm particle size.

Example 21

Preparation of Fluorescent Polymer Particles

The procedures are just the same as that in Example 18, except that the emulsifier concentration decreases to 0.02 wt %.

Figure 18B:
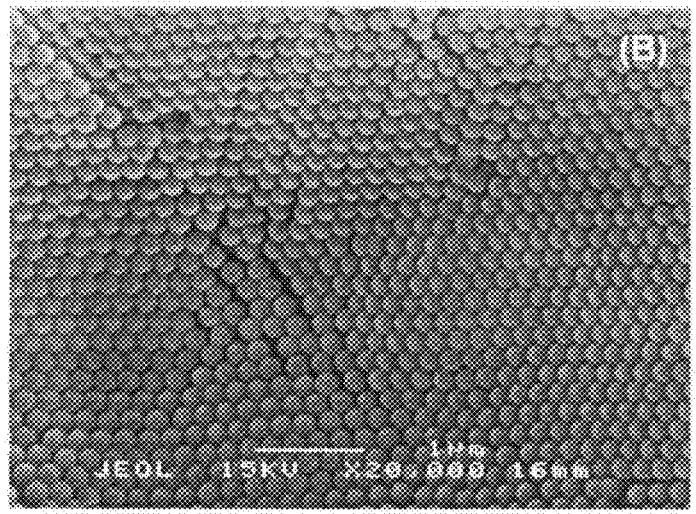
FIG. 18B is a scanning electron micrograph image of the fluorescent polymer particles of Example 21 prepared at a surfactant concentration of 0.02 wt %.

The polymer particle dispersion prepared is quite uniform and stable. The particle dispersion is highly emissive under UV irradiation, even in very dilute state. The SEM image of the fluorescent polymer particles are shown in FIG. 18B, indicating a 250 nm particle size.

Example 22

Preparation of Fluorescent Polymer Particles

The procedures are just the same as that in Example 18, except that the emulsifier concentration decreases to 0.04 wt %.

Figure 18C:
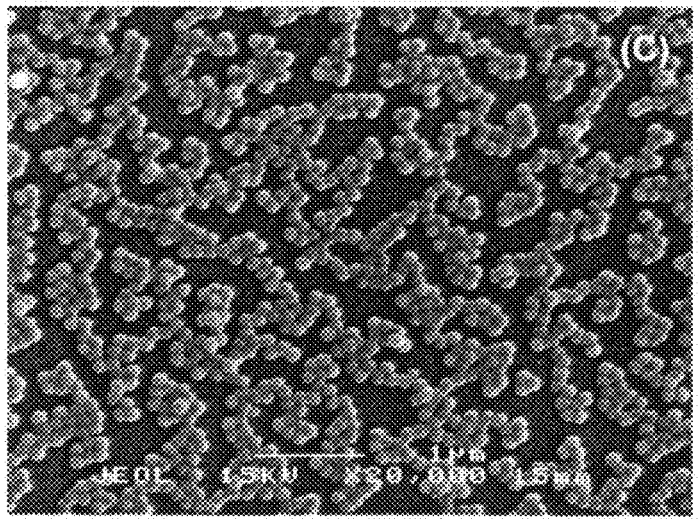
FIG. 18C is a scanning electron micrograph image of the fluorescent polymer particles of Example 22 prepared at a surfactant concentration of 0.04 wt %.

The polymer particle dispersion prepared is quite uniform and stable. The particle dispersion is highly emissive under UV irradiation, even in very dilute state. The SEM image of the fluorescent polymer particles are shown in FIG. 18C, indicating a 120 nm particle size.

Example 23

Preparation of Fluorescent Polymer Particles

The procedures are just the same as that in Example 18, except that 2-hydroxyethyl methacrylate is replace by acrylic acid.

The polymer particle dispersion prepared is quite uniform and stable. The particle dispersion is highly emissive under UV irradiation, even in very dilute state. The fluorescent particles have carboxyl functional groups on the surface, which is favorable to the bioconjugation.

Example 24

Preparation of Fluorescent Polymer Particles

The procedures are just the same as that in Example 19, except that 2-hydroxyethyl methacrylate is replace by acrylamide.

The polymer particle dispersion prepared is quite uniform and stable. The particle dispersion is highly emissive under UV irradiation, even in very dilute state. The fluorescent particles have amine functional groups on the surface, which is favorable to the bioconjugation.

Example 25

Preparation of Fluorescent Polymer Coating

The procedures for preparation of fluorescent dispersion are just the same as that in Example 17. The particle dispersion is highly emissive under UV irradiation, even in very dilute state. The size of the fluorescent particle is less than 100 nm and the glass transition temperature is below room temperature. The dispersion prepared is suitable for film formation, and the fluorescent coating film is shown in FIG. 19A. The coating film formed by control dispersion is nonluminescent while that formed by the fluorescent particle dispersion is highly emissive under UV irradiation.

Example 26

Preparation of Fluorescent, Free-Standing, Flexible Polymer Film

The procedures for preparation of fluorescent dispersion are just the same as that in Example 17. The particle dispersion is highly emissive under UV irradiation, even in very dilute state. The size of the fluorescent particle is less than 100 nm and the glass transition temperature is below room temperature. The dispersion prepared is suitable for film formation. With a PTFE mold, a free-standing flexible film can be facilely fabricated, and the fluorescent film is shown in FIG. 19B. The coating film formed by control dispersion is nonluminescent while that formed by the fluorescent particle dispersion is highly emissive under UV irradiation. Such fluorescent free-standing flexible polymer film can be used as flexible organic optoelectronic devices.

Example 27

The fluorescent polymer nanoparticles with amino groups were prepared with the method demonstrated in Example 23. The nanoparticle suspension was diluted 10 times by minimum essential media. Then 10 mg of transferrin (Tf) was added into this mixture and gently stirred at room temperature for 2 hours to allow the protein to covalently bond to the particle surface. The human cancer cell lines HeLa was cultured in Dulbecco minimum essential media with 10% fetal bovine serum (FBS), 1% penicillin, and 1% amphotericin B. The day before treatment, cells were seeded in 35 mm culture dishes at a confluency of 70-80%. On the treatment day, the cells in serum-supplemented media were treated with the Tf-conjugated nanoparticles for 2 hours at 37° C. Afterwards, the cells were washed three times with PBS and directly imaged using a fluorescent microscope.

Figure 20A:
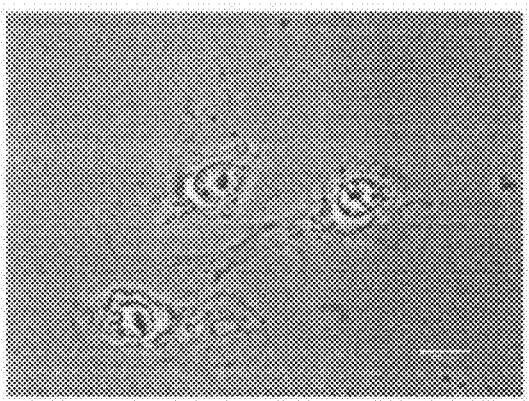
FIG. 20A is a transmission electron micrograph image of HeLa cell treated with the fluorescent polymer nanoparticles of Example 27.
Figure 20B:
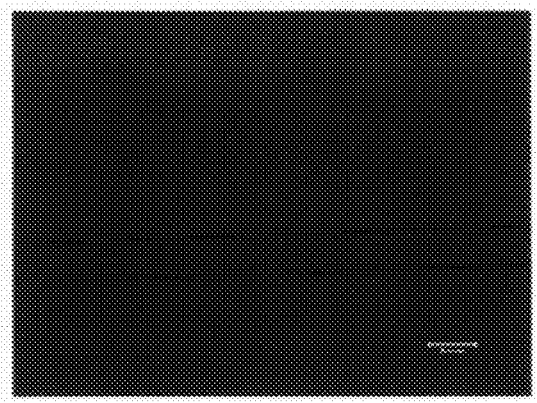
FIG. 20B is a transmission electron micrograph image of HeLa cells treated with the fluorescent polymer nanoparticles of Example 27 upon excitation of 365 nm UV light.

The results are shown in FIG. 20. From the microscopic fluorescence images, it can be seen that the whole cells are bright, indicating that the fluorescent nanoparticles have migrated into the cells. In other words, they are labeled.

Results on cell labeling using the fluorescent polymer nanoparticles have been obtained. As shown below, 48 nm fluorescent polymer nanoparticles were first prepared with amino groups on the surface, and then bioconjugation of transferring, a known protein that tends to target HeLa cells, was carried out. Subsequently, the HeLa cells in serum-supplemented media were treated with the particle-transferrin conjugates. As a result, transferring-conjugated nanoparticles were transported into the cells through the transferrin receptor mediated endocytosis pathway. Since transferrin receptors are minimally distributed in normal cells, transferrin serves as an excellent ligand for preferentially targeting cancerous cells in vitro and in vivo. From the microscopic fluorescence image (FIG. 20), it can be seen that the whole cells are bright, indicating that the fluorescent nanoparticles have migrated into the cells. In other words, they are labeled.

Example 28

Figure 21:
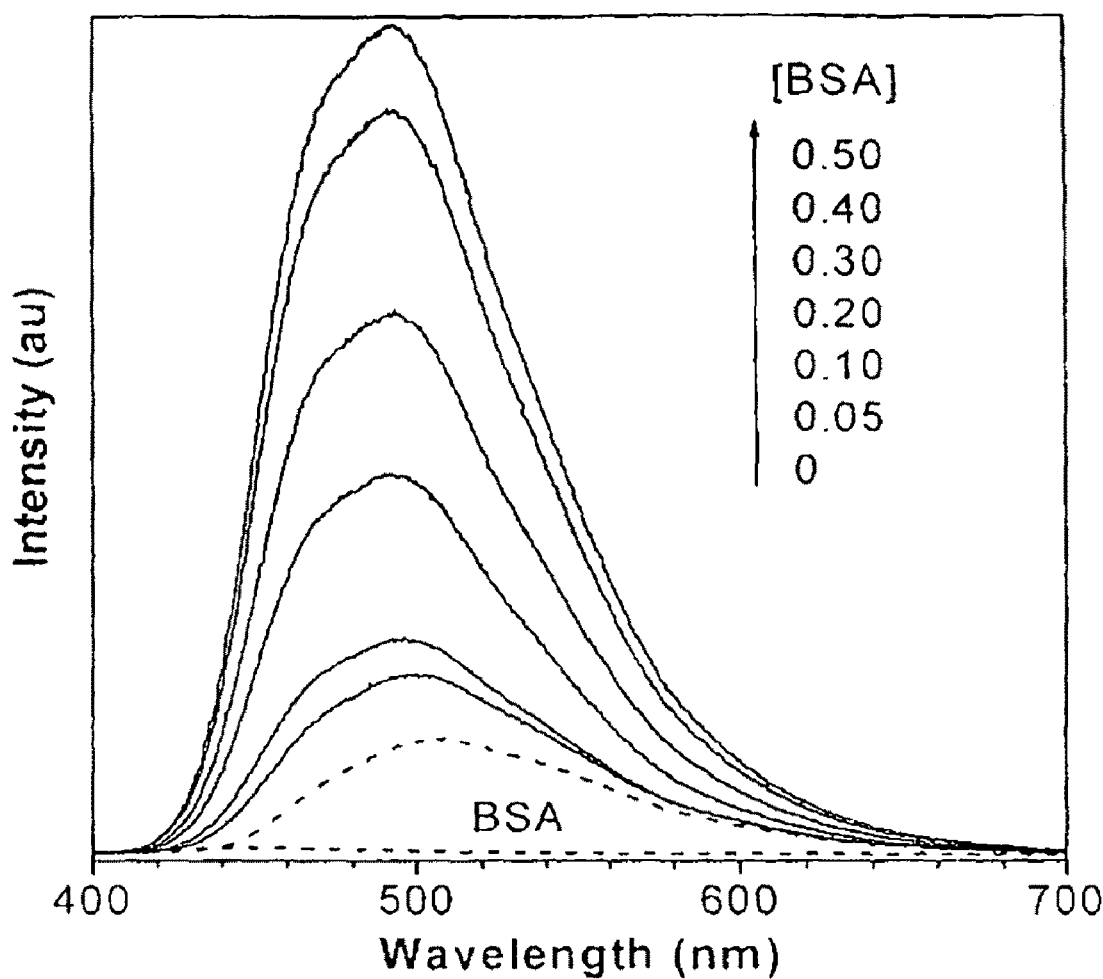
FIG. 21 is PL spectra of the water/methanol (6:4) solutions of a PPS-OH ($5.7 \times 10^{-5}$ M) in the presence of KOH ($8.4 \times 10^{-4}$ M) and BSA (at concentrations given in the figure), as described in Example 28.
Figure 22:
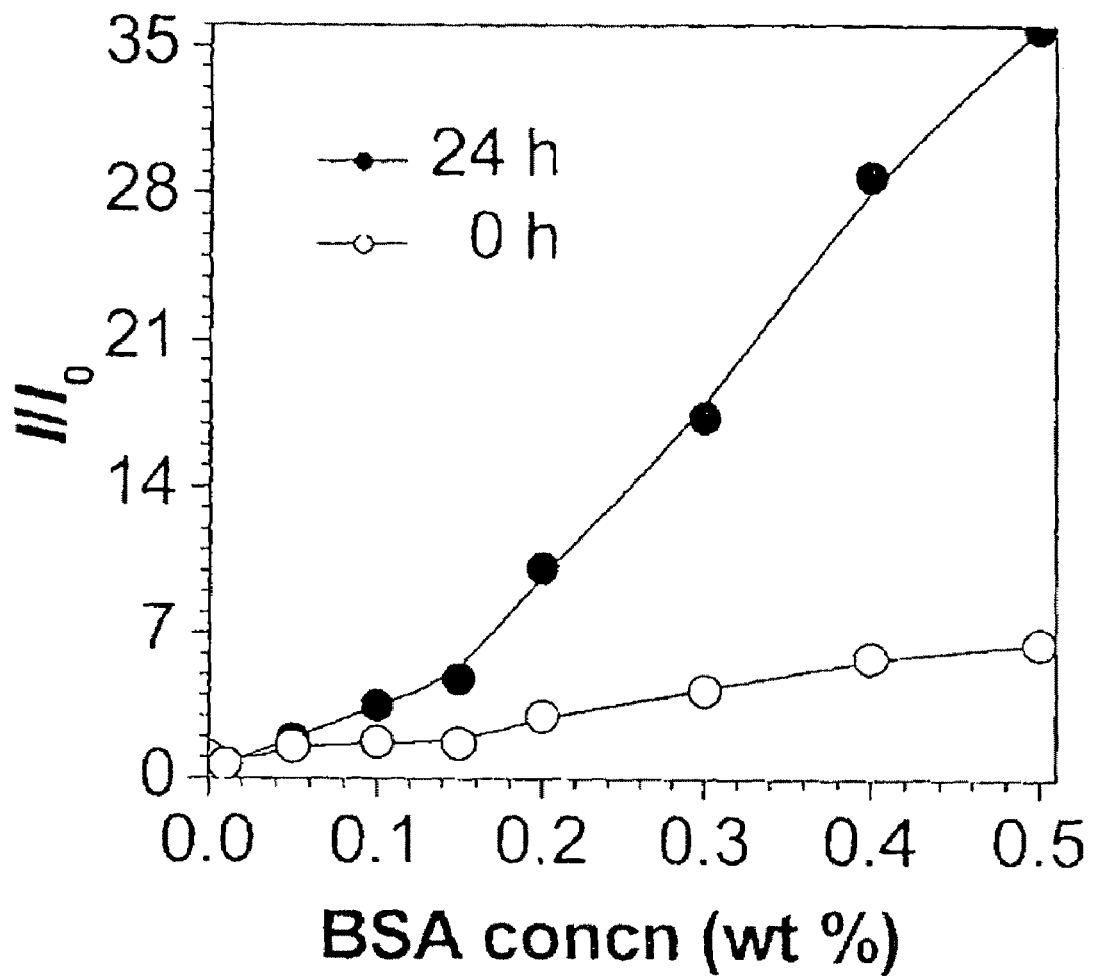
FIG. 22 shows the dependency of fluorescence intensity of PPS-OH on BSA concentration as described in Example 28.

In order to utilize the dye molecules as biosensors in aqueous solutions, we prepared PPS-OH and tested its ability to detect bovine serum albumin (BSA). FIG. 21 depicts the PL spectra of the water/methanol (6:4) solutions of a PPS-OH in the presence of KOH and BSA at different concentrations. Clearly, with increasing amounts of BSA the PL intensity increases significantly. Upon prolonged standing the PL intensity enhances further, probably due to the more complete interaction of PPS-OH with BSA (FIG. 22).

Example 29

Quadruplex Recognition

A complex of ssDNA and TTAPE was prepared by mixing 10 µL G1 (0.1 mM) and 50 µL TTAPE (0.01 mM) in 5 mM Tris-HCl buffer in a 1.5 mL Eppendorf cup. The solution was incubated at 4° C. for 30 min. G-quadruplex formation was induced by adding 10 µL of a 1.0 M KCl solution into the Eppendorf cup. The final concentrations of TTAPE and G1 were kept at 4.5 and 9.0 µM, respectively. For other cationic species, the same amounts of corresponding salts were used. Kinetic experiment was conducted immediately after the injection of the cationic solution, while other spectral measurements were performed after an incubation period of 30 mm.

Figure 30:
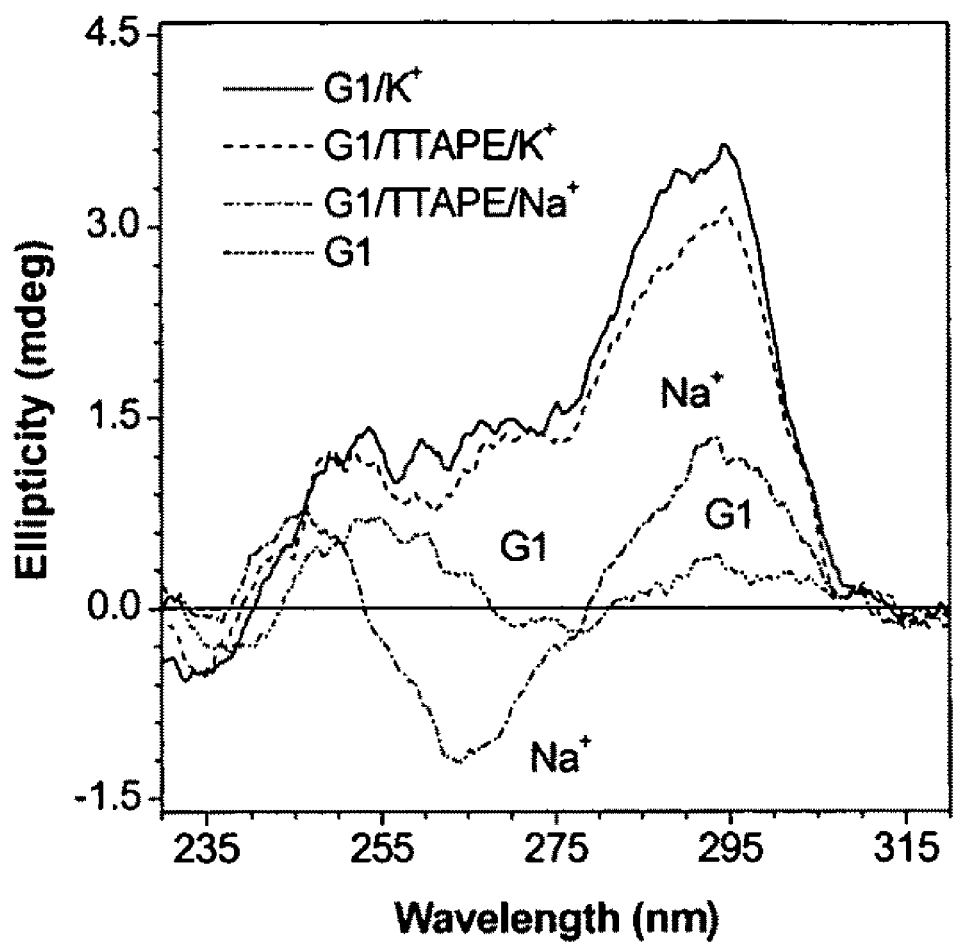
FIG. 30 is a CD spectra of G1 in a Tris-HCl buffer in the presence or absence of a metal ion and/or TTAPE at 20° C. [G1]=9 μM, [ion]=0.5 M, [TTAPE]=4.5 μM.

In the aqueous buffer solution, G1 takes a random coil conformation and shows a weak circular dichroism (CD) curve (FIG. 30). Adding $K^+$ into the G1 solution (G1/$K^+$) promotes G-quadruplex formation,[24] which brings about a change in the CD spectral profile as well as an increase in the ellipticity. The G1/TTAPE/$K^+$ system shows a CD curve with a similar profile and ellipticity, implying that the dye does not affect the quadruplex conformation. The quadruplex formation induces ~20 nm red-shift in both excitation and emission spectra of TTAPE (FIG. 31). A serial titration experiment using $K^+$ as titrate reveals that the spectral red-shift starts from [$K^+$]≈10 mM and completes at [$K^+$]≈100 mM (FIG. 32). The FL intensity at 470 nm, on the other hand, is monotonically decreased with increasing the $K^+$ concentration. Closer inspection of the data finds that the spectrum at high [$K^+$] contains a shoulder band at ~400 nm. This shoulder is probably associated with the emission of the TTAPE molecules that are still bound to the quadruplex but via only one or two of its four ammonium arms. These partially bound dye molecules may undergo partial intramolecular rotations and thus emit weak light in the blue spectral region.

Figures 33A, 33B:
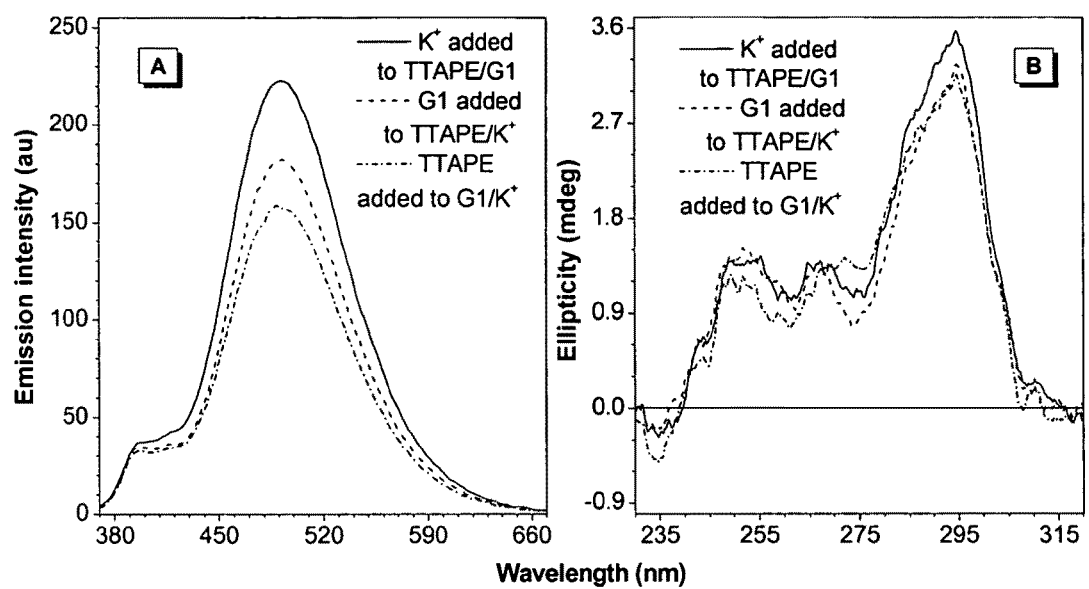
FIG. 33A shows the effects of addition sequence on FL spectra of $K^+$/TTAPE/G1 complex in 5 mM Tris-HCl buffer solutions. [$K^+$]=0.5 M, [TTAPE]=4.5 μM, [G1]=9 μM; $\lambda_{ex}$=350 mm.
FIG. 33B shows the effects of addition sequence on CD spectra of $K^+$/TTAPE/G1 complex in 5 mM Tris-HCl buffer solutions. [$K^+$]=0.5 M, [TTAPE]=4.5 μM, [G1]=9 μM; $\lambda_{ex}$=350 nm.

The addition sequence is systematically investigated to see how it affects the FL and CD spectra of the TTAPE/quadruplex structure. As can be seen from the data summarized in Table 2 and FIGS. 33A and 33B, the FL/CD intensities vary in the order of following addition sequence: $K^+$→TTAPE/G1>G1→TTAPE/$K^+$>TTAPE→G1/$K^+$. Comparison of the data in entries 1 and 2 (Table 2) suggests that some TTAPE molecules pre-bound to the G1 strands have been incorporated into the G-quadruplex structure during the $K^+$-induced structural transformation. When TTAPE is added after the G-quadruplex has been formed (entry 3), the dye molecules are difficult to bind to the quadruplex surrounded by numerous $K^+$ ions, hence the observed lowest FL and CD intensities. The profiles of the CD spectra for all the G-quadruplexes formed in the three entries are almost identical (FIG. 33B), confirming that TTAPE does not appreciably distort the G-quadruplex structure.

TABLE 2

Effect of addition sequence on FL and CD intensities of TTAPE/quadruplex complexes at room temperature[a]

| Entry | Mixture[b] | Additive | FL intensity[c] | CD intensity[d] |
|---|---|---|---|---|
| 1[e] | TTAPE/G1 | $K^+$ | 1.00 | 1.00 |
| 2 | TTAPE/$K^+$ | G1 | 0.82 | 0.92 |
| 3 | G1/$K^+$ | TTAPE | 0.70 | 0.88 |

[a]For comparison final concentrations of the three components in all the mixtures were adjusted to be the same.
[b]Incubated at 4° C. for 30 min.
[c]Relative intensity at 492 nm.
[d]Relative intensity at 295 nm.
[e]Data corresponding to those given in FIGS. s 30 and 31.

Example 30

Figure 34A:
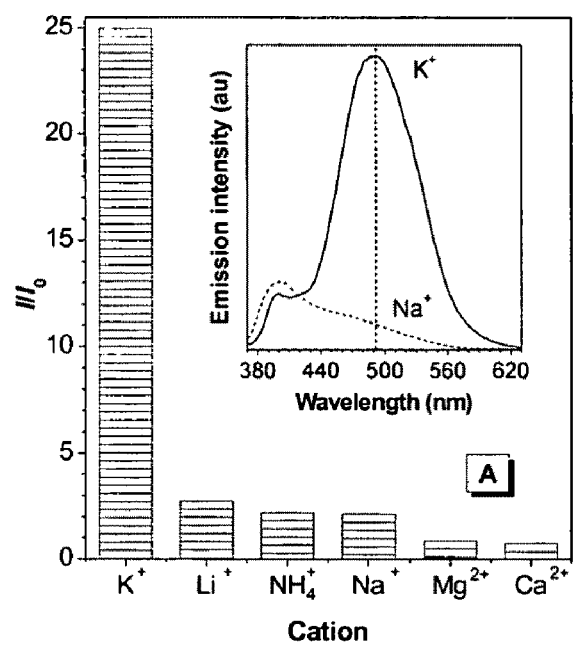
FIG. 34A shows the dependence of FL intensity of TTAPE at 492 nm on cationic species ([ion]=500 mM). FL spectra of TTAPE in the buffer solutions containing G1 and $K^+$ or $Na^+$ ion.
Figure 34B:
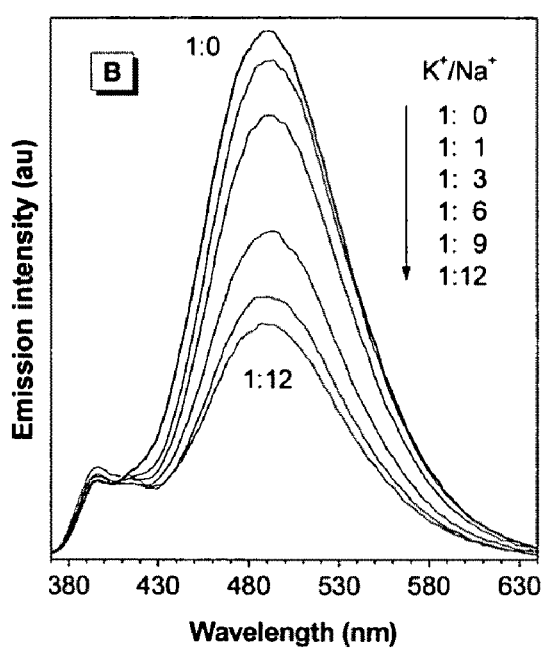
FIG. 34B shows the variation in the FL spectrum of TTAPE/G1/$K^+$ solution with addition of $Na^+$ ion. [TTAPE]= 4.5 μM, [G1]=9 μM, [$K^+$]=100 mM; $\lambda_{ex}$=350 nm.
Figures 35A, 35B:
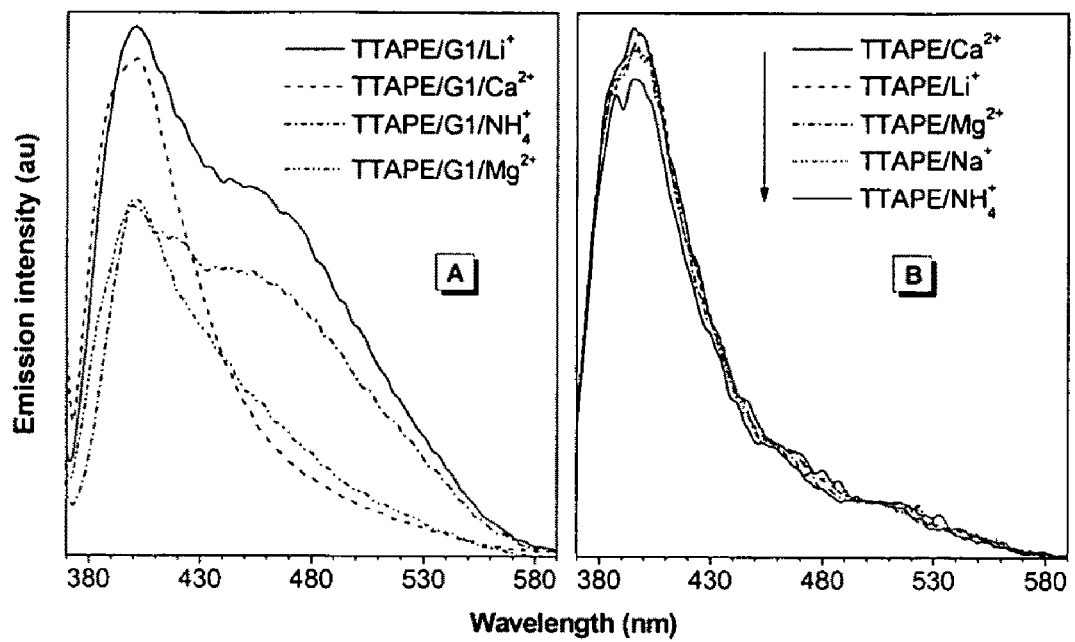
FIG. 35A shows the FL spectra of TTAPE/G1 in a Tris-HCl buffer in the presence of cationic species. [TTAPE]=4.5 μM, [G1]=9 μM, [ion]=0.5 M; $\lambda_{ex}$=350 nm.
FIG. 35B shows the FL spectra of TTAPE in a Tris-HCl buffer in the presence of cationic species. [TTAPE]=4.5 μM, [G1]=9 μM, [ion]=0.5 M; $\lambda_{ex}$=350 nm.

As stated above, addition of $K^+$ into TTAPE/G1 results in a quadruplex-specific emission peak at 492 nm. Addition of $Na^+$ into TTAPE/G1, however, quenches this band (FIG. 34A). Similarly, other cationic species including $Li^+$, $NH_4^+$, $Mg^{2+}$ and $Ca^{2+}$ all attenuate this emission band (FIGS. 35A and 35B). After adding into TTAPE/G1, these cation species competes with TTAPE for binding with G1. The externally added cation species prevails because its amount is >$10^4$-fold higher than that of TTAPE. Once the dye molecules are stripped from the DNA strand, their intramolecular rotations are no longer restricted and the AIE band is thus turned off. The FL spectrum of TTAPE/G1 in the presence of $K^+$ is clearly different from, and its peak intensity is outstandingly higher than, those in the presence of other cations, suggesting the potential utility of TTAPE/G1 as a $K^+$ biosensor.

Example 31

Effects of DNA Strands

DNA samples of G1, C1 and C2 were obtained from Operon in desalt purity and used without further purification. G1 was chosen as a model ssDNA mimicking the human telomeric repeat sequence $d(T_2AG_3)$, which is capable of forming intramolecular G-quadruplex. Concentrations of the DNA strands were determined by measuring their absorptivity (ε) values at 260 nm in a 100 µL quartz cuvette [ε(×$10^5$ $M^{-1}$ $cm^{-1}$): 2.14 (G1), 1.85 (C1), 1.85 (C2)]. Water was purified by a Millipore filtration system. Buffer solution was prepared by titrating 5 mM Tris with HCl until its pH value reached 7.50. All experiments were performed at room temperature unless otherwise specified.

If a DNA contains no G unit, its TTAPE complex ceases to show the quadruplex-specific response to $K^+$. C1 is also a 21-mer ssDNA, but unlike G1, it possesses no G-rich repeat sequence. When C1 is admixed with TTAPE, a blue emission at 474 nm is resulted (FIG. 38A). This emission is, however, quenched upon addition of other cations including $K^+$. Different from G1, C1 cannot fold into G-quadruplex structure in the presence of K$^+$. The K$^+$ ions here just compete with the TTAPE molecules for DNA binding, thus resulting in the expulsion of the dye molecules from the C1 strand and the quenching of the light emission.

Figure 39:
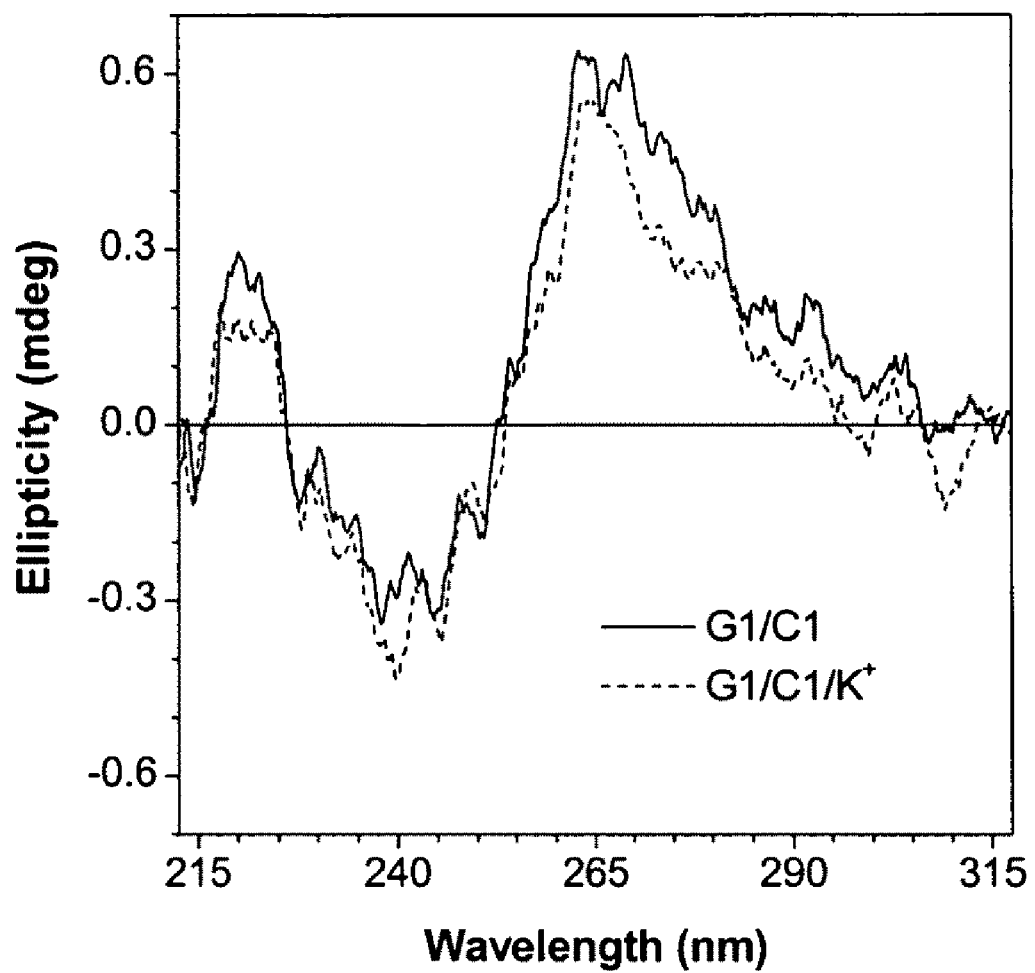
FIG. 39 shows the CD spectra of G1/C1 in the absence or presence of $K^+$ after hybridization in a Tris-HCl buffer (pH=7.50). [G1]=[C1]=4.5 μM, [$K^+$]=0.5 M; $\lambda_{ex}$=350 nm.
Figure 40:
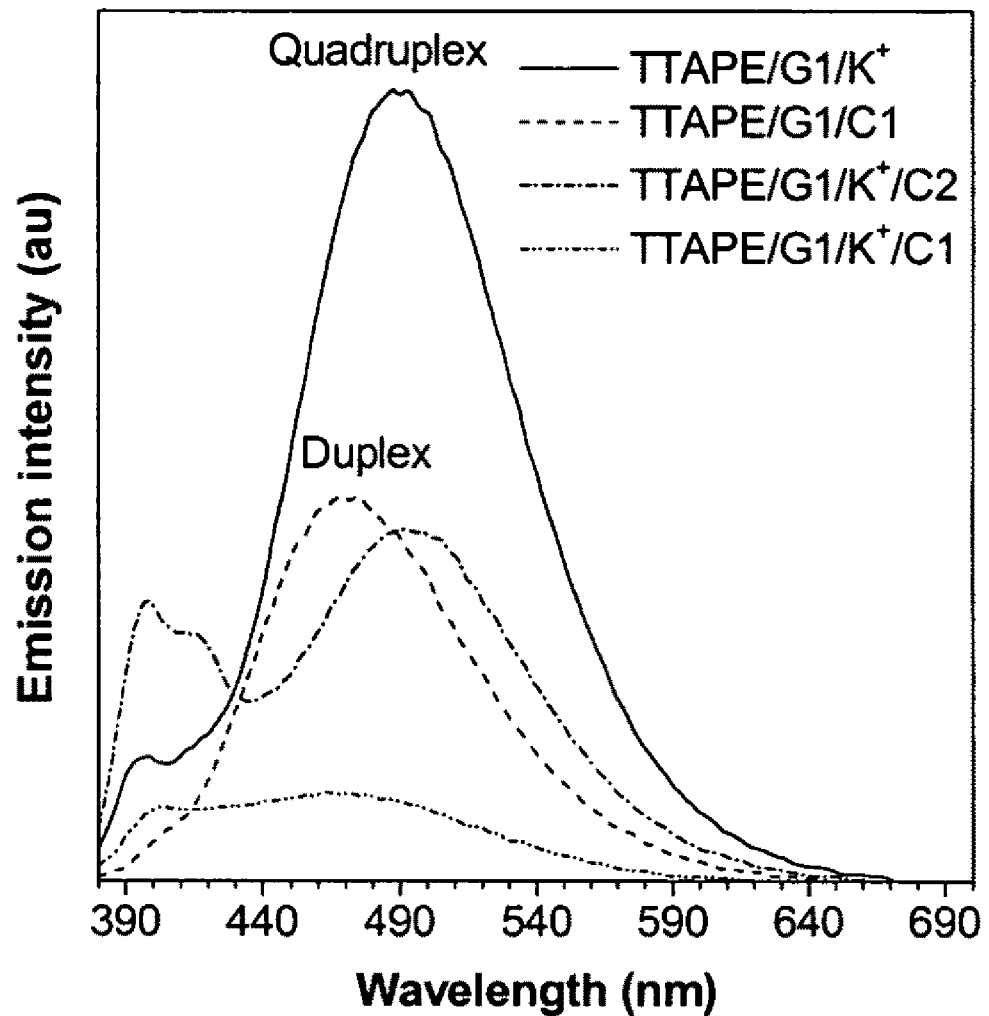
FIG. 40 shows the emission spectra of TTAPE/G1 in a Tris-HCl buffer in the presence of $K^+$ and/or C1 or C2. [TTAPE]=4.5 μM, [$K^+$]=0.5 M; $\lambda_{ex}$=350 nm; [G1]=9 μM (in the absence of Ci), [G1]=[Ci]=4.5 μM (in the presence of Ci)
Figure 41:
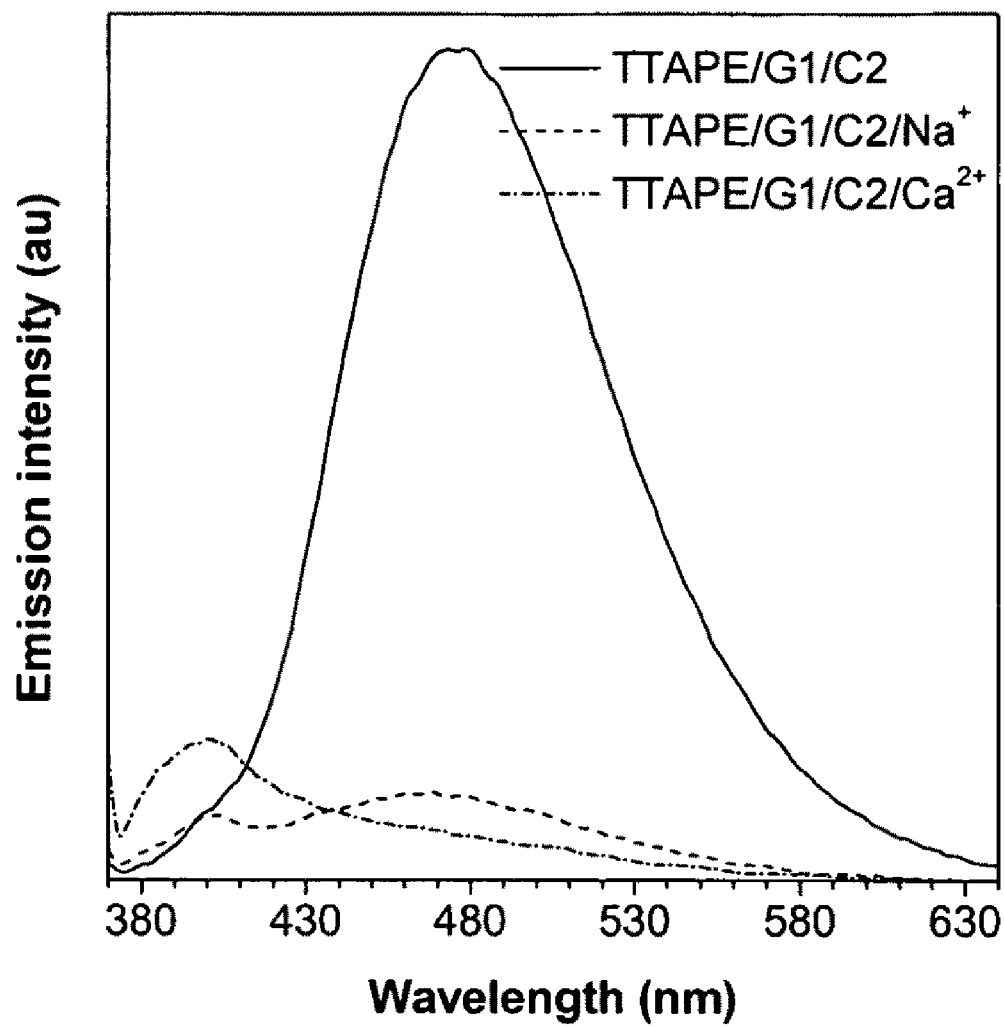
FIG. 41 shows the emission spectra of buffer solutions of TTAPE/C2 in the absence and presence of metal ions. [TTAPE]=4.5 μM, [G1]=[C2]=4.5 μM, [ion]=0.5 M; $\lambda_{ex}$=350 nm

To be qualified as a specific probe for G-quadruplex recognition, the dye must be able to distinguish the quadruplex from other DNA conformations, especially the double-stranded (ds) one, which is the most ubiquitous conformation for DNAs in living organisms. C1 is a complimentary strand of G1: the two DNA strands hybridize to form a duplex (FIG. 39). The dsDNA induces TTAPE to emit at 470 nm, which is different from the dye emission in the presence of the G-quadruplex ($\lambda_{em}$=492 nm; FIG. 40). The interaction of TTAPE with dsDNA is again electrostatic in nature: when large amounts of other cations are added into G1/C1 solutions, the bound dye molecules are replaced by the externally added cations and the AIE emission band is accordingly attenuated (FIG. 41).

For comparison, the quadruplex/TTAPE complex is mixed with equal molar amounts of its complementary and non-complementary strands C1 and C2, respectively. The resultant TTAPE/G1/K$^+$/Ci mixtures are annealed at ~58° C., a temperature ~2° C. below the melting points of the DNAs (~60° C.) for 15 min, followed by a slow cooling to 25° C. to allow double-helix formation. The hybridization of G1 with C1 unfolds the G-quadruplex structure and yields a duplex (dsDNA). As a result, the quadruplex-specific emission at 492 nm is quenched (FIG. 40). The duplex is saturated by the prevailingly large amount of K$^+$ ions and leaves little room for TTAPE molecules to bind, hence making the solution non-emissive. Similar results are obtained for other cationic species (FIG. 38B).

Since C2 is noncomplementary to G1, the G-quadruplex remains unperturbed and the emission at 492 nm is preserved. Intriguingly, however, the emission in the bluer region (at ~400 nm) is increased upon admixing with C2. Although the whole strand of C2 is non-complementary to G1, partial hybridization of some base units of C2 with those of the G-quadruplex of G1, especially those on its surface, via GC and/or AT base pairing is possible. Such pairing replaces some, although not all, of the ammonium groups of a TTAPE bound to the G-quadruplex. The dye molecules hanging on the quadruplex via one or two ammonium arms can undergo partial intramolecular rotations and thus emit in the bluer spectral region. Addition of large amounts of other cationic species into the TTAPE/G1/C2 solutions drives all the dye molecules out of touch with the DNA strands. As a result, the solutions become nonemissive (FIG. 41).

Example 32

Time-Dependent FL

Time-dependent FL was measured on a FluostarOptima multifunctional microplate reader (BMG Labtechnologies) with $\lambda_{ex}/\lambda_{em}$ set at 350/470 nm. To gain insight into dynamics of the folding process of G1, time-dependent FL measurements are performed. Solutions containing TTAPE and G1 are first incubated for 30 min to ensure complete dye/DNA complexation and transferred to a 96-well microtiter plate after incubation. Appropriate amounts of metal ions were added by an automatic injection mode. Kinetic measurements were performed at 20° C. and the FL data were recorded in every 4 s. The change in the emission intensity (I) of the solution after the addition of K$^+$ can be fitted by a second-order exponential curve:[30]

$$I = A_1 e^{-t/\tau_1} + A_2 e^{-t/\tau_2} + c \quad (1)$$

where t is the time, $\tau_1$ and $\tau_2$ are the time constants of FL recovery, $A_1$ and $A_2$ are the respective amplitudes (the folding process is characterized by negative A values), and c is the FL intensity at t=∞. Mean time constant (<τ>) was calculated according to eq. 2:

$$<\tau> = \frac{A_1 \tau_1 + A_2 \tau_2}{A_1 + A_2}. \quad (2)$$

Figure 42:
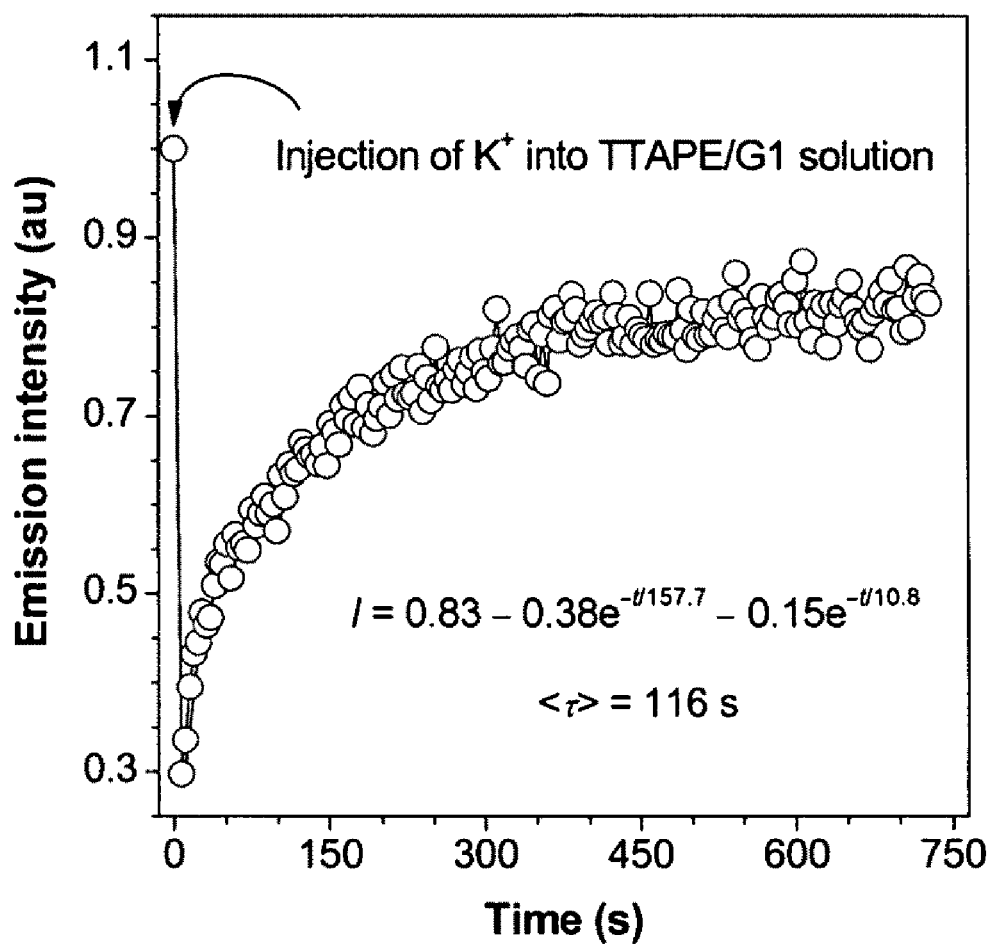
FIG. 42 is the time course of evolution of emission intensity at 470 nm of TTAPE/G1 in a Tris-HCl buffer after injection of a $K^+$ solution. [TTAPE]=4.5 μM, [G1]=9 μM, [$K^+$]=.5 M; $\lambda_{ex}$=350 m

In one embodiment, a solution of potassium chloride is then injected at time t=0 (automatic injection mode) and the emission intensity at 470 nm is monitored. The emission drops abruptly to ~30% of its original intensity at the beginning but starts to recover after ~8 s and finally reaches a plateau at ~320 s (FIG. 42). This suggests a very fast ion-exchange process between K$^+$ and TTAPE with G1 at the beginning. Because of its smaller size and higher concentration, K$^+$ outperforms TTAPE in the DNA binding, leading to the initial quick drop in the FL intensity. The G1 strand then starts to fold into quadruplex with the aid of K$^+$, during which the TTAPE molecules are attracted to bind with the quadruplex, as manifested by the recovery of the FL signal after ~8 s. The complete folding of G1 into the quadruplex conformation takes only ~5 min. This result is consistent with the observations in the previous studies on the DNA folding processes using the surface plasmon resonance and electrospray mass spectrometry techniques.

Figures 43A, 43B:
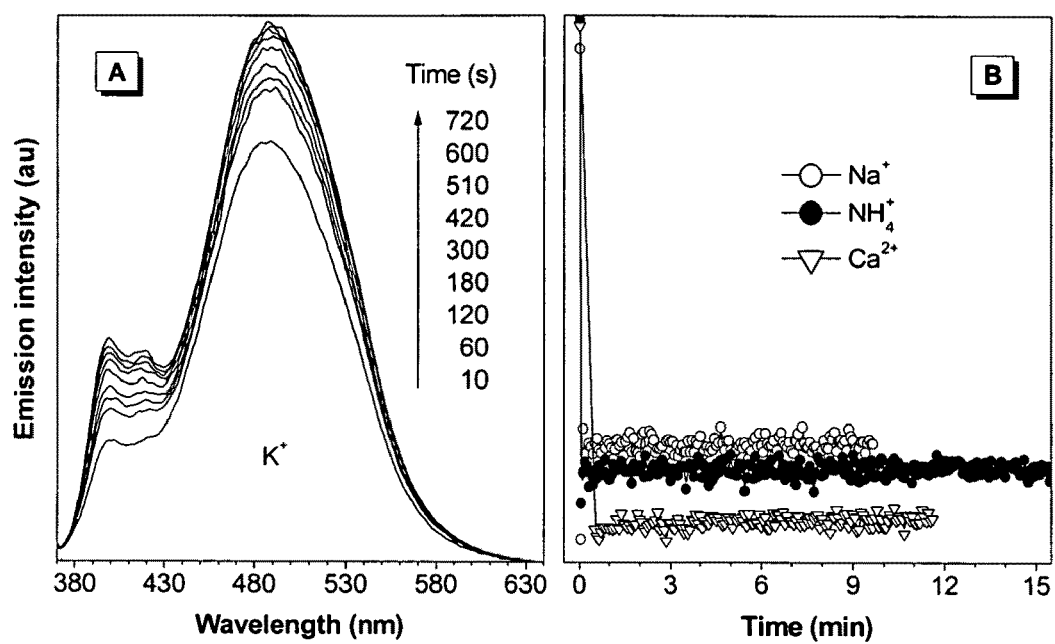
FIG. 43A is the time courses of evolution of emission intensities of buffer solutions of TTAPE/G1 after addition of cationic species. [TTAPE]=4.5 μM, [G1]=9 μM; $\lambda_{ex}$=350 nm; [$K^+$]=0.5 M.
FIG. 43B is the time courses of evolution of emission intensities of buffer solutions of TTAPE/G1 after addition of cationic species. [TTAPE]=4.5 μM, [G1]=9 μM; $\lambda_{ex}$=350 nm; [$Na^+$]=[$NH_4^+$]=0.5 M, [$Ca^{2+}$]=0.25 M.
Figures 44A, 44B:
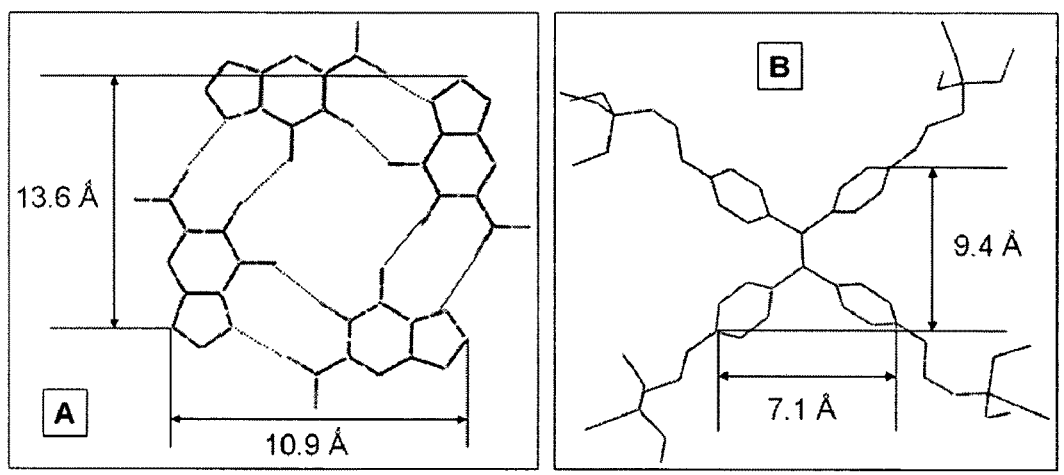
FIG. 44A shows the selected crystal structure of G-quadruplex of a human telomeric DNA (data taken from RSCB Protein Data Bank; ID No. 1KF1)
FIG. 44B shows the molecular structure of TTAPE with minimized energy, simulated by molecular mechanics MM2 program installed in Chem3D Ultra 8.0.

The FL recovery process can be fitted by a double-exponential curve, giving a weighted mean time constant (<τ>) of 116 s. The inverse of <τ> can be viewed as a rate constant, allowing one to have a kinetic picture of the folding process of the DNA. Control experiments using other cationic species such as Na$^+$, NH$_4^+$ and Ca$^{2+}$ reveal similar FL decreases (FIG. 43), suggesting that the same ion-exchange mechanism is involved in the dye detachment processes. The emission intensities, however, fail to recover from the low values even after a time period as long as 1000 s. For Na$^+$ and NH$_4^+$, it is probably due to the geometric unfitness of TTAPE with the G-quadruplexes formed in the presence of these two cationic species. For Ca$^{2+}$ it is simply because this ion cannot induce the formation of a G-quadruplex structure.

Example 33

Urinary Protein Detection

Urine is an easily accessible body fluid and contains a complex mixture of proteins and peptides, which makes it a reliable source of biomarkers for diagnostics and clinical studies. Determination of urinary protein composition is of major clinical importance because it readily reflects serum composition and kidney functionality. The synthesis route of TPE-SO3 is described in Example 2 above.

Figure 46A:
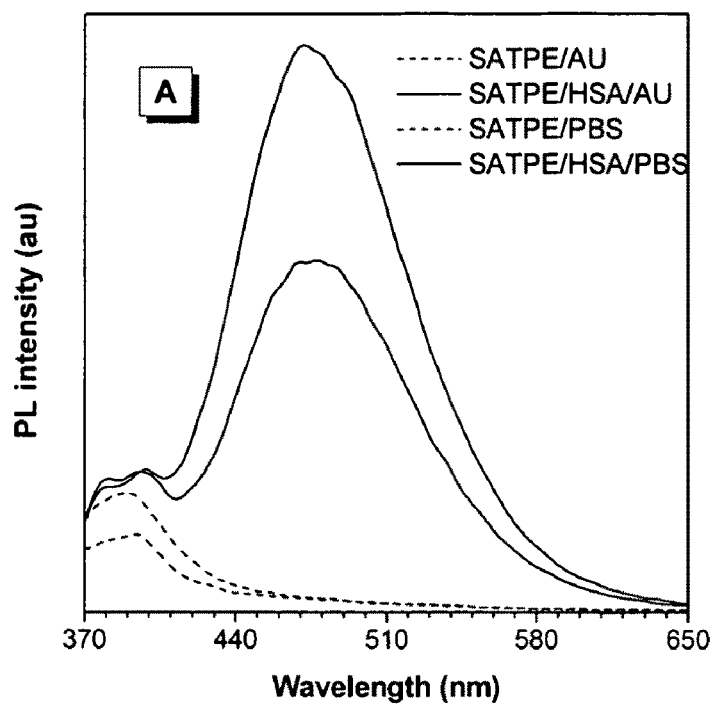
FIG. 46A shows the PL spectra of SATPE with/without HSA in the medium of artificial urine (AU) (pH=6.0)/PBS (pH=7.0). [SATPE]=5 μM; [HSA]=10 μg/mL
Figure 46B:
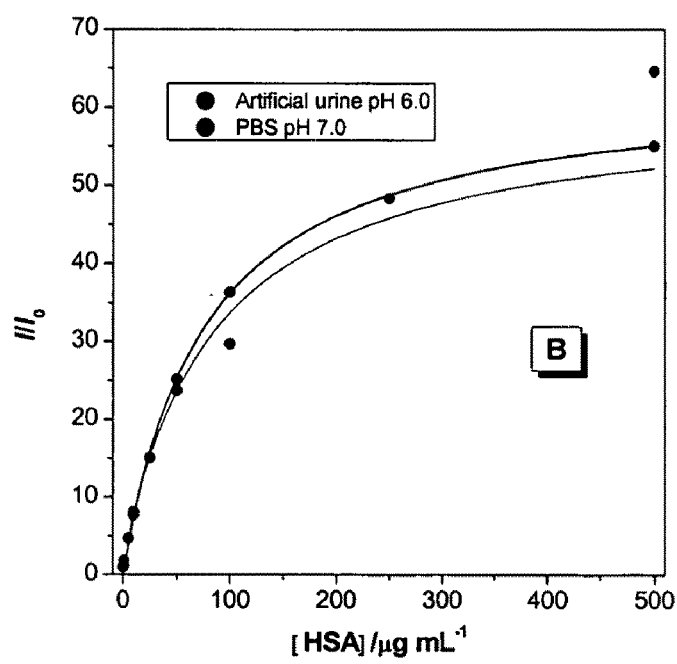
FIG. 46B shows the binding isotherm of HSA to SATPE in artificial urine pH=6.0 (black) (plot of FL intensity at 470 nm). The one in PBS pH=7.0 (red) is for comparison. [SATPE]=5 μM; excitation wavelength: 350 nm.

The water-soluble salt TPE-SO3 is expected to be suitable for protein detection and quantification as an FL bioprobe. A stock solution of TPE-SO3 (0.5 mM) was prepared by directly dissolving it in a ph 7.0 phosphate buffer. The dye solution in the absence of HSA, a model protein, is almost nonemissive (FIG. 46A). Its emission is switched on instantly by the addition of HSA. Its intensity increase (up to ~55-fold, FIG. 46B) and linear range (0-100 ug/mL. In order to determine whether TPE-SO3 can be used in the medium of urine or not, we perform experiments in artificial urine solution (pH 6.0). An artificial urine solution was prepared according to the recipe provided by Brooks and Keevil (T. Brooks, C. W.

Keevil, *Lett. Appl. Microbiol.* 1997, 24, 203997, The artificial urine solution was 1.1 mm lactic acid, 2.0 mm citric acid, 25 mm sodium bicarbonate, 170 mm urea, 2.5 mm calcium chloride, 90 mm sodium chloride, 2.0 mm magnesium sulfate, 10 mm sodium sulfate, 7.0 mm potassium dihydrogen phosphate, 7.0 mm dipotassium hydrogen phosphate, and 25 mm ammonium chloride all mixed in Millipore water. The pH of the solution was adjusted to 6.0 through the addition of 1.0m hydrochloric acid.

Figures 47A, 47B:
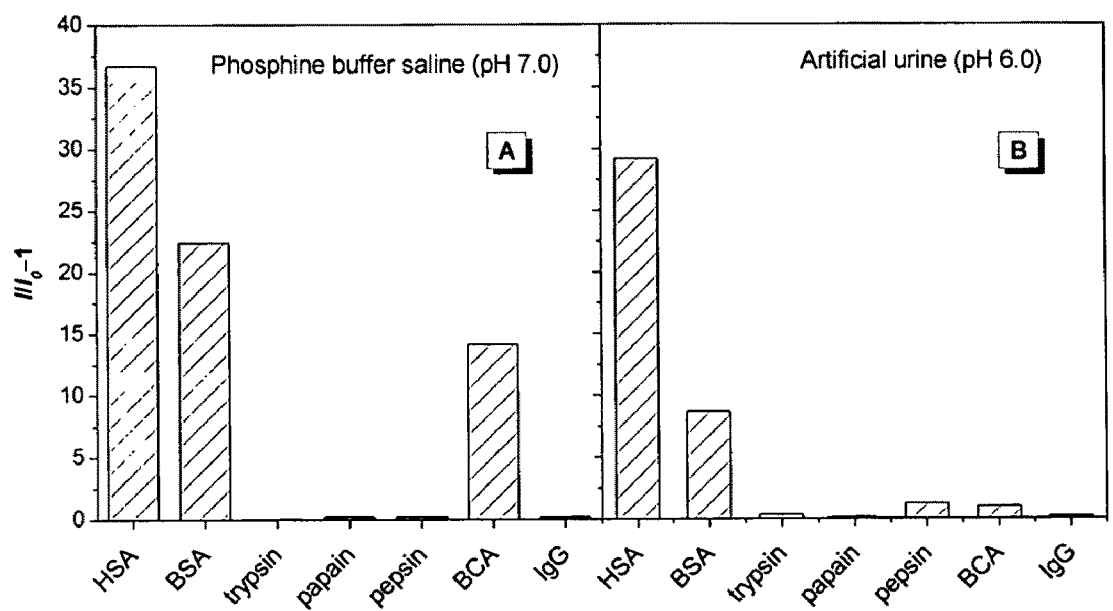
FIG. 47A shows the dependence of FL intensity of SATPE at 476 nm on different proteins in phosphate buffer solution. [SATPE]=5 μM, [protein]=100 μg/mL. Excitation wavelength: 350 nm.
FIG. 47B shows the dependence of FL intensity of SATPE at 476 nm on different proteins in artificial urine. [SATPE]=5 μM, [protein]=100 μg/mL. Excitation wavelength: 350 nm.
Figure 48:
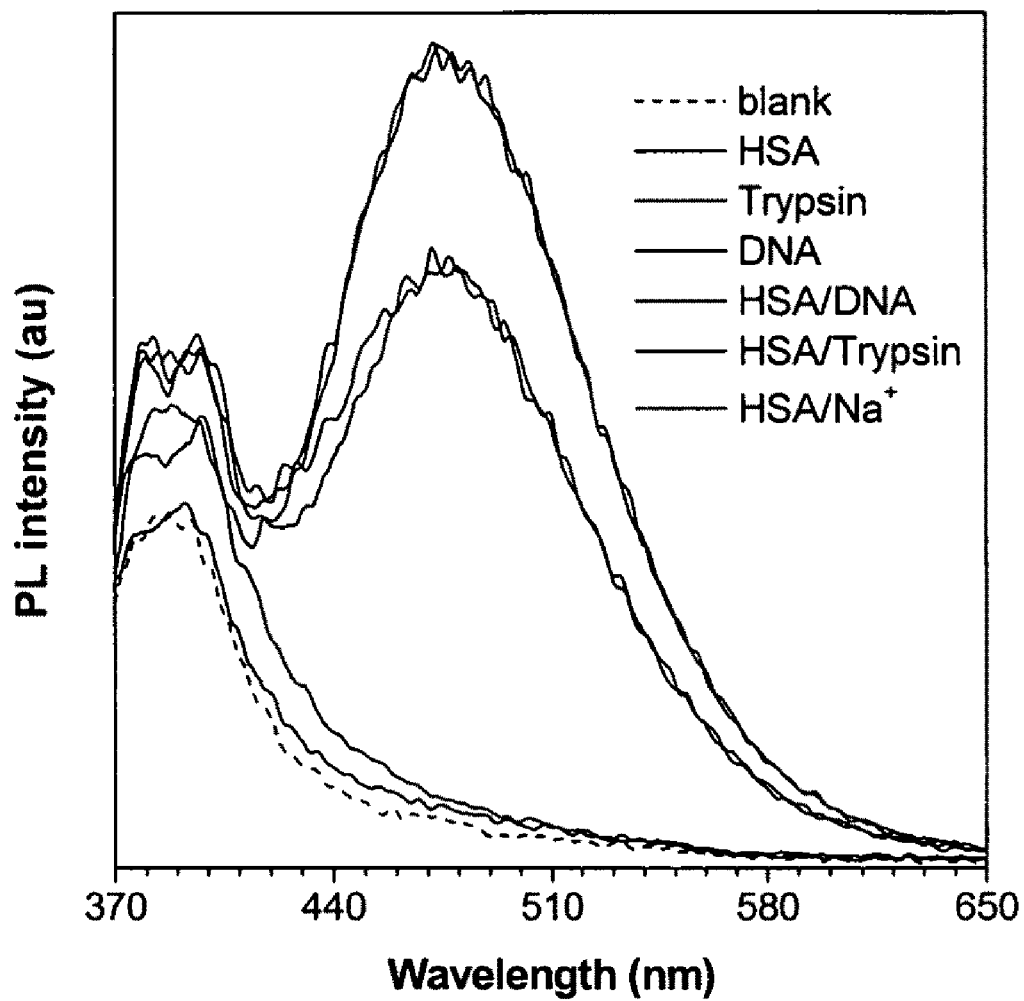
FIG. 48 shows the FL spectrum of SATPE with addition of different proteins in artificial urine (pH=6.0). [SATPE]=5 μM, [protein]=50 μg/mL. Excitation wavelength: 350 nm.

The results show that the presence of high concentration of urea and salts do not interfere with the function of TPE-SO3. The detection limit and linear range can be tuned by adjusting the dye concentration. Intriguingly, TPE-SO3 displays high affinity to albumin over any other proteins (FIGS. 47A and 47B). Albumin proteins, such as HSA, may have a large hydrophobic cavity which may attract the dyes to stay in it, leading to strong binding interaction. On the other hand, other kinds of protein, such as trypsin, papain, pepsin, and IgG can only adsorb the dyes on the surface of the protein by electrostatic interaction. Thus, in the medium with high ionic strength may mitigate their interaction, resulting in weak or no FL signals. Cross-contaminant experiments were also performed (FIG. 48). The results show that the interaction of TPE-SO3 with HSA can hardly be affected in the presence of other species.

Figure 25:
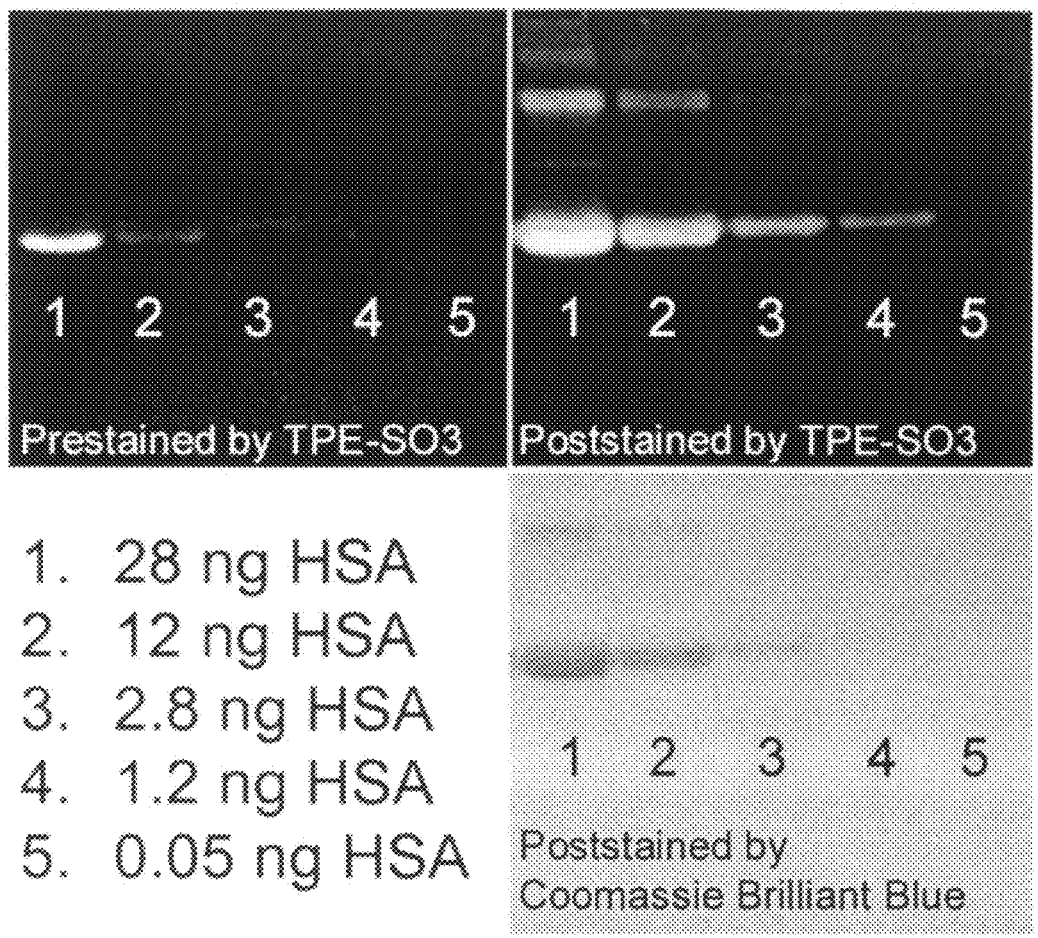
FIG. 25 shows the 12% Native-PAGE of HSA pre/post-stained by TPE-SO3. The gel is poststained by Coomassie Brilliant Blue for comparison.

Similar to TTAPE, TPE-SO3 can also be used in PAGE assays for detecting proteins in biological samples. In a prestaining process samples are mixed with TPE-SO3 prior to being loaded into the gel. The results of the prestaining process with TPE-SO3 can be seen in top left portion of FIG. 25. In addition, a poststaining process was performed where after electrophoresis, the gel was immersed into TPE-SO3 solution for 5 mins before taking an images. The results of the poststaining process with TPE-SO3 can be seen in the top right portion of FIG. 25.

Coomassie Brilliant Blue is a blue dye that can bind to the proteins of a within the PAGE assay and allow you to directly visualize them. After Coomassie staining and destaining, the proteins will appear as blue bands as shown in the lower right portion of FIG. 25. Coomassie Brilliant Blue staining requires long reaction time (normally soaked more than 6 hours), destaining step (immersed in acid solution to dissolve the unbound dyes), and low sensitivity (colorimetric-based method) (see U.S. Pat. No. 5,922,186). In contrast, TPE-SO3 offers an easy and sensitive way to do this same job. Gels only need to be exposed to TPE-SO3 for 3-5 minutes to make the protein bands visible. The use of TPE-SO3 requires no destaining step. The sensitivity of TPE-SO3 is much higher than that of Coomassie Brilliant Blue. It is clear that the use of TPE-SO3 as a stain for PAGE assays is a faster method with fewer steps that provides greater sensitivity than conventional staining methods for protein detection.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

---

We claim:

1. A method of detecting G-quadruplex formation, DNA, or protein and protein levels in a biological sample comprising contacting the biological sample with a water-soluble conjugated polyene compound and detecting luminescence.

2. The method of claim 1 wherein the water-soluble conjugated polyene compound comprises a backbone structure of a formula selected from the group consisting of:

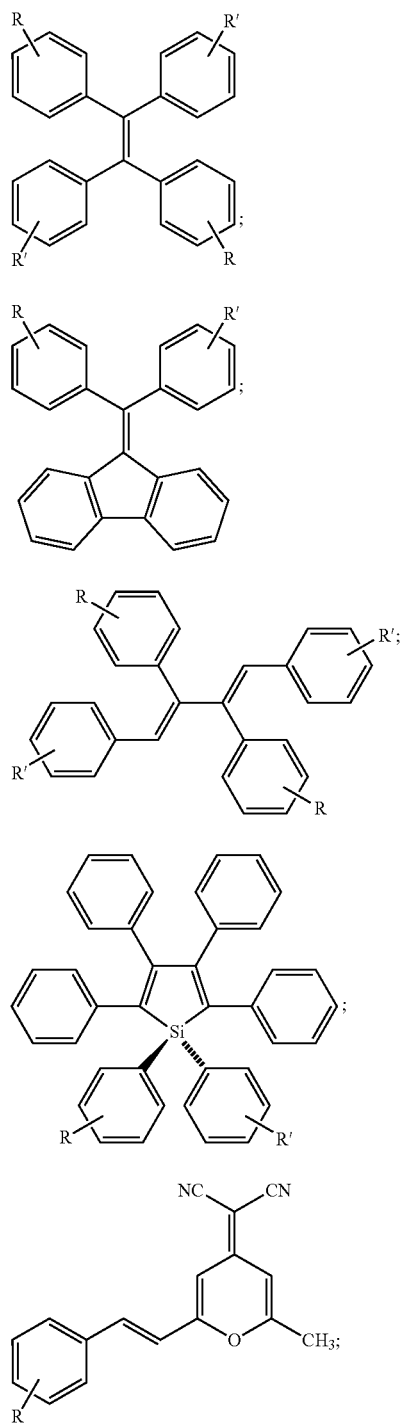

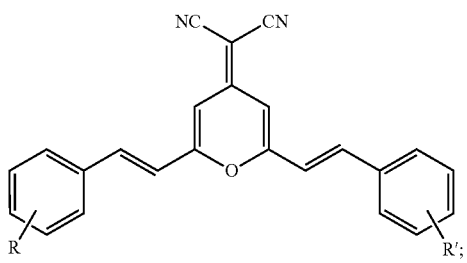

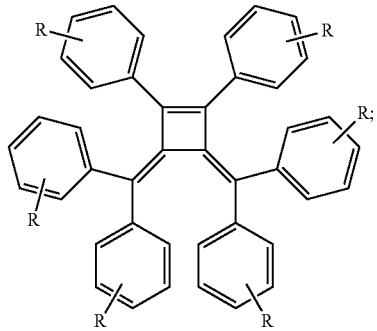

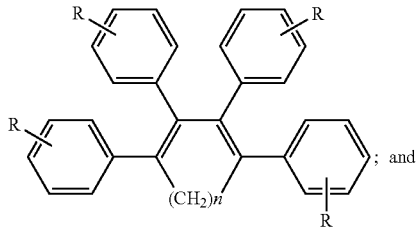

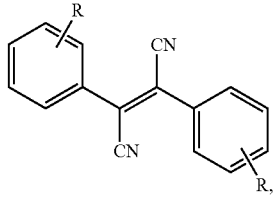

wherein R and R' are independently selected from the group consisting of H, X, B(OH)$_2$, (X)$_n$COOR", (X)$_n$COOH, (X)$_n$NH$_2$, (X)$_n$NHR", (X)$_n$NR"$_2$, (X)$_n$N+R"$_3$Br$^-$, (X)$_n$OH, (X)$_n$SH, (X)$_n$SO$_3^-$Na$^+$,

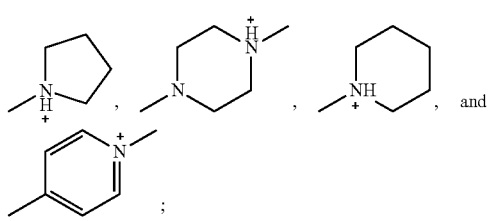

X is selected from (CH$_2$)$_n$, O(CH$_2$)$_n$, NH(CH$_2$)$_n$, N[(CH$_2$)]$_2$, and (OCH$_2$CH$_2$)$_n$; and R" is selected from R, R', (CH$_2$)$_n$CH$_3$, CONH—X—, COO—X—, C$_6$H$_5$—R, —CH$_2$—C$_6$H$_5$, and C$_6$H$_5$; and wherein n=0 to 20, and the compound is water-soluble and exhibits aggregation induced emission.

3. The method of claim 1 wherein the conjugated polyene compound forms a complex with a G-rich strand sequences of the biological sample which activates the fluorescence of the polyene.

4. The method of claim 1 wherein a cation is added to the biological sample and polyene mixture.

5. The method of claim 4 wherein the cation is selected from the group consisting of $K^+$, $Li^+$, $Na^+$, $NH_4^+$, $Mg^{2+}$, $Ca^{2+}$, and mixtures thereof.

6. The method of claim 5 wherein the cation is $K^+$.

7. The method of claim 4 wherein fluorescence emission intensity is monitored for any spectral shifts signaling the presence of a G-quadruplex conformation in the folded oligonucleotide.

8. The method of claim 1 wherein the water-soluble conjugated polyene compound is a tetraphenylethylene ("TPE").

9. The method of claim 8 wherein the TPE is selected from the group consisting of 1,2-diphenyl-1,2-bis(4,4'-(3-sulfonato)propoxyl)phenylethylene (TPE-SO3) and 1,1,2,2-tetrakis[4-(2-triethylammonioethoxy)-phenyl]ethene tetrabromide (TTAPE).

10. The method of claim 9 wherein the TPE is 1,1,2,2-tetrakis[4-(2-triethylammonioethoxy)-phenyl]ethene tetrabromide (TTAPE).

11. The method of claim 10 wherein the biological sample is selected from the group consisting of a tissue sample, cell sample, blood, saliva, spinal fluid, lymph fluid, vaginal fluid, seminal fluid, and urine.

12. The method of claim 11 wherein the biological sample is urine.

13. The method of claim 1 wherein the protein being detected in the biological sample is human serum albumin.

* * * * *

UNITED STATES PATENT AND TRADEMARK OFFICE
CERTIFICATE OF CORRECTION

PATENT NO.         : 8,129,111 B2
APPLICATION NO.    : 12/453892
DATED              : March 6, 2012
INVENTOR(S)        : Benzhong Tang et al.

Page 1 of 1

It is certified that error appears in the above-identified patent and that said Letters Patent is hereby corrected as shown below:

Column 66, lines 62 to 63, after "NH(CH2)N," and before ", and (OCH2CH2)N;" please replace "N[(CH2)]2" with --N[(CH2)n]2--.

Signed and Sealed this
Sixth Day of November, 2012

David J. Kappos
*Director of the United States Patent and Trademark Office*

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide G1 mimicking human telomeric
      repeat sequence

<400> SEQUENCE: 1
gggttagggt tagggttagg g                                             21

<210> SEQ ID NO 2
<211> LENGTH: 21
<212> TYPE: DNA
<213> ORGANISM: Artificial Sequence
<220> FEATURE:
<223> OTHER INFORMATION: Complimentary ssDNA of G1 (C1)

<400> SEQUENCE: 2
ccctaaccct aaccctaacc c                                             21

<210> SEQ ID NO 3
<211> LENGTH: 21
<212> TYPE: DNA
<213> ORGANISM: Artificial Sequence
<220> FEATURE:
<223> OTHER INFORMATION: Non-complimentary ssDNA of G1 (C2)

<400> SEQUENCE: 3
cccaatccca atcccaatcc c                                             21
```